United States Patent
Suthanthiran et al.

(10) Patent No.: US 10,472,679 B2
(45) Date of Patent: Nov. 12, 2019

(54) NON-INVASIVE METHOD OF DIAGNOSING RENAL FIBROSIS

(71) Applicant: Cornell University, Ithaca, NY (US)

(72) Inventors: Manikkam Suthanthiran, Scarsdale, NY (US); Joseph E. Schwartz, East Setauket, NY (US); Ruchuang Ding, Beechurst, NY (US); Thangamani Muthukumar, New York, NY (US)

(73) Assignee: Cornell University, Ithica, NY (US)

( * ) Notice: Subject to any disclaimer, the term of this patent is extended or adjusted under 35 U.S.C. 154(b) by 526 days.

(21) Appl. No.: 14/400,873

(22) PCT Filed: May 15, 2013

(86) PCT No.: PCT/US2013/041206
§ 371 (c)(1),
(2) Date: Nov. 13, 2014

(87) PCT Pub. No.: WO2013/173493
PCT Pub. Date: Nov. 21, 2013

(65) Prior Publication Data
US 2015/0240305 A1  Aug. 27, 2015

Related U.S. Application Data

(60) Provisional application No. 61/647,347, filed on May 15, 2012.

(51) Int. Cl.
*C12Q 1/6883* (2018.01)
*G16H 50/20* (2018.01)

(52) U.S. Cl.
CPC ........... *C12Q 1/6883* (2013.01); *G16H 50/20* (2018.01); *C12Q 2600/118* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 2003/0113744 A1* | 6/2003 | O' Toole et al. ..... | C12Q 1/6883 435/6.14 |
| 2003/0148286 A1* | 8/2003 | Larose ................. | C12Q 1/6809 435/6.14 |
| 2006/0078900 A1* | 4/2006 | Mendrick ............ | C12Q 1/6883 435/6.11 |
| 2011/0288134 A1 | 11/2011 | Maksumova et al. | |

FOREIGN PATENT DOCUMENTS

| WO | WO-2011054893 A2 | 5/2011 |
|---|---|---|
| WO | WO-2013173493 A1 | 11/2013 |

OTHER PUBLICATIONS

McDonald, J. H. Handbook of Biological Statistics. (2008). Excerpt of pp. 148-152.*
Multiple sequence alignment of SEQ ID No. 2, SEQ ID No. 4, and ALQ33846.1. 1 page.*
Sequence alignment of SEQ ID No. 6 and AIC59269.1. 1 page.*
Multiple sequence alignment of SEQ ID No. 8, SEQ ID No. 10, and ALS87660.1. 2 pages.*
Sequence alignment of SEQ ID No. 11 and K03432.1. 3 pages.*
John, R. & Herzenberg, A. M. Renal toxicity of therapeutic drugs. Journal of Clinical Pathology 62, 505-515 (2009).*
Fassett, R. G. et al. Biomarkers in chronic kidney disease: A review. Kidney International 80, 806-821 (2011).*
Fliser, D. et al. Advances in Urinary Proteome Analysis and Biomarker Discovery. Journal of the American Society of Nephrology 18, 1057-1071 (2007).*
Hewitt, S. M., Dear, J. & Star, R. A. Discovery of protein biomarkers for renal diseases. Journal of the American Society of Nephrology 15, 1677-1689 (2004).*
Molitoris, B. A., Melnikov, V. Y., Okusa, M. D. & Himmelfarb, J. Technology Insight: biomarker development in acute kidney injury—what can we anticipate? Nature Clinical Practice Nephrology 4, 154-165 (2008).*
Pisitkun, T., Johnstone, R. & Knepper, M. A. Discovery of Urinary Biomarkers. Molecular & Cellular Proteomics 5, 1760-1771 (2006).*
Siwy, J., Mullen, W., Golovko, I., Franke, J. & Zürbig, P. Human urinary peptide database for multiple disease biomarker discovery. Proteomics—Clinical Applications 5, 367-374 (2011).*
Thongboonkerd, V. & Malasit, P. Renal and urinary proteomics: Current applications and challenges. Proteomics 5, 1033-1042 (2005).*
Vaidya, V. S., Ferguson, M. A. & Bonventre, J. V. Biomarkers of Acute Kidney Injury. Annual Review of Pharmacology and Toxicology 48, 463-493 (2008).*
Boor, P., Šebeková, K., Ostendorf, T. & Floege, J. Treatment targets in renal fibrosis. Nephrology Dialysis Transplantation 22, 3391-3407 (2007).*
Boor, P., Ostendorf, T. & Floege, J. Renal fibrosis: Novel insights into mechanisms and therapeutic targets. Nature Reviews Nephrology 6, 643-656 (2010).*
Liu, Y. Renal fibrosis: New insights into the pathogenesis and therapeutics. Kidney International 69, 213-217 (2006).*

(Continued)

*Primary Examiner* — Soren Harward
(74) *Attorney, Agent, or Firm* — Schwegman Lundberg & Woessner, P.A.

(57) ABSTRACT

Measurement of mRNAs in urinary cells offers a noninvasive means of diagnosing fibrosis in kidneys. One aspect of the invention is a method that includes: (a) measuring quantities of vimentin mRNA, NKCC2 mRNA, and E-cadherin mRNA in a test sample of cells obtained from urine; and (b) determining whether the vimentin mRNA quantity is higher, the NKCC2 mRNA quantity is lower, or the E-cadherin mRNA is higher than in healthy urinary cells; and thereby detecting that the sample is a fibrotic kidney sample. Step (a) can also include measuring the quantity of RNA expressed by a housekeeping gene (e.g., 18S rRNA). The quantities of vimentin mRNA, NKCC2 mRNA, and E-cadherin mRNA can be normalized against the quantity of housekeeping gene RNA.

5 Claims, 22 Drawing Sheets

Specification includes a Sequence Listing.

(56) References Cited

OTHER PUBLICATIONS

"International Application Serial No. PCT/US2013/041206, International Search Report dated Oct. 11, 2013", 5 pgs.

"International Application Serial No. PCT/US2013/041206, Written Opinion dated Oct. 11, 2013", 6 pgs.

Anglicheau, et al., "Discovery and Validation of a Molecular Signature for the Noninvasive Diagnosis of Human Renal Allograft Fibrosis", Transplantation. 93(11), (Jun. 15, 2012), 1136-1146.

Anglicheau, et al., "Epithelial-Mesenchymal Transition (EMT) and Fibrosis Are Rapidly Induced during Acute Rejection (AR) of Human Renal Allografts", Poster presentation (F-PO2089). J AM Soc Nephrol 20, (2009).

Cheng et al., "Connective Tissue Growth Factor is a Biomarker and Mediator of Kidney Allograft Fibrosis", AM J Transplant, (Aug. 4, 2006), 2292-22306.

Kaneyama, et al., "Tranilast modulates fibrosis, epithelial-mesenchymal transition and peritubular capillary injury in unilateral ureteral obstruction rats", Pathology 42(6), (Oct. 2010), 564-573.

"International Application Serial No. PCT/US2013/041206, International Preliminary Report on Patentability dated Nov. 27, 2014", 8 pgs.

Anglicheau, D., et al., "Noninvasive Prediction of Organ Graft Rejection and Outcome Using Gene Expression Patterns", Transplantation, 86(2), (2008), 192-199.

Beckingham, I. J., et al., "Analysis of factors associated with complications following renal transplant needle core biopsy", Br J Urol, 73(1), (1994), 13-15.

Bielesz, B., et al., "Epithelial Notch signaling regulates interstitial fibrosis development in the kidneys of mice and humans", The Journal of Clinical Investigations, 120(11), (2010), 4040-4054.

Boor, P., et al., "Renal fibrosis: novel insights into mechanisms and therapeutic targets", Nat Rev Nephrol, 6(11), (2010), 643-656.

Hertig, A., et al., "Early Epithelial Phenotypic Changes Predict Graft Fibrosis", J Am Soc Nephrol, 19(8), (2008), 1584-1591.

Hotchkiss, H., et al., "Differential Expression of Profibrotic and Growth Factors in Chronic Allograft Nephropathy", Transplantation, 81(3), (2006), 342-349.

Ivaska, J., et al., "Novel functions of vimentin in cell adhesion, migration, and signaling.", Exp Cell Res, 313(10), (2007), 2050-2062.

Koesters, R., et al., "Tubular Overexpression of Transforming Growth Factor-B1 Induces Autophagy and Fibrosis but Not Mesenchymal Transition of Renal Epithelial Cells", The American Journal of Pathology, 177(2), (2010), 632-643.

Li, B., et al., "Noninvasive Diagnosis of Renal-Allograft Rejection by Measurement of Messenger RNA for Perforin and Granzyme B in Urine", The New England Journal of Medicine, 344(13), (2001), 947-954.

Liu, Y., et al., "Endogenous hepatocyte growth factor ameliorates chronic renal injury by activating matrix degradation pathways", Kidney International, 58(5), (2000), 2028-2043.

Liu, Y., et al., "Up-regulation of hepatocyte growth factor receptor: An amplification and targeting mechanism for hepatocyte growth factor action in acute renal failute", Kidney International, 55(2), (1999), 442-453.

Lohr, J. W., "Increased levels of serum hepatocyte growth factor in patients with end-stage renal disease", (Abstract), J Med, 31(3-4), 131-141, (2000), 1 pg.

Maluf, D. G., et al., "Molecular Pathways involved in Loss of Kidney Graft Function with Tubular Atrophy and Interstitial Fibrosis", Mol Med, 14(5-6), (2008), 276-285.

Mas, V., "Establishing the Molecular Pathways Involved in Chronic Allograft Nephropathy for Testing New Noninvasive Diagnostic Markers", Transplantation, 83(4), (2007), 448-457.

Mizuno, S., et al., "HGF as a renotrophic and anti-fibrotic regulator in chronic renal disease", [online]. Front Biosci, 13, 7072-7086, May 1, 2008. Retrieved from the Internet: <URL: https://www.bioscience.org/2008/v13/af/3211/fulltext.htm>, (2008), 22 pgs.

Mizuno, S., et al., "Reciprocal balance of hepatocyte growth factor and transforming growth factor-β1 in renal fibrosis in mice", Kidney International, 57(3), (2000), 937-948.

Muthukumar, T., et al., "Messenger RNA for FOXP3 in the Urine of Renal-Allograft Receipients", New England Journal of Medicine, 353(22), (2005), 2342-2351.

Nakatsuji, S., et al., "Relationship between vimentin expressing renal tubules and interstitial fibrosis in chronic progressive nephropathy in aged rates", Virchows Arch, 433(4), (1998), 359-367.

Park, W., et al., "Molecular Evidence of Injury and Inflammation in Normal and Fibrotic Renal Allografts One Year Posttransplant", Transplantation, 83(11), 2007, 1466-1476.

Scherer, A., et al., "Transcriptome changes in renal allograft protocol biopsies at 3 months precede the onset of interstitial fibrosis/tubular atrophy (IF/TA) at 6 months", Nephrol Dial Transplant, 24, (2009), 2567-2575.

Sharma, V. K., et al., "Intragraft TGF-B1 mRNA: A correlate of interstitial fibrosis and chronic allograft nephropathy", Kidney International, 49(5), (1996), 1297-1303.

Solez, K., et al., "Banff 07 Classification of Renal Allograft Pathology: Updates and Future Directions", American Journal of Transplantation, 8, (2008), 753-760.

Sorof, J. M., et al., "Histopathological Concordance of Paired Renal Allograft Biopsy Cores—Effect on the Diagnosis and Management of Acute Rejection", Transplantation, 60(11), (1995), 1215-1219.

Strutz, F., "Pathogenesis of tubulointerstitial fibrosis in chronic allograft dysfunction", Clinical Transplantation, 23(Suppl. 21), (2009), 26-32.

Suthanthiran, M., et al., "Urinary Cell Messenger RNA Expression Signatures Anticipate Acute Cellular Rejection: A Report from CTOT-04", (Abstract #1), American Transplant Congress 2011 Abstracts, Am J Transplant, 11(Suppl 2), (2011), p. 29.

Wynn, T. A., "Cellular and molecular mechanisms of fibrosis", Journal of Pathology, 214, (2008), 199-210.

Xu. G.-P., et al., "Intragraft expression of IL-10 messenger RNA: A novel correlate of renal allograft rejectiion", Kidney International, 48, (1995), 1504-1507.

Yang, J., et al., "Blockage of Tubular Epithelial to Myofibroblast Transistion by Hepatocyte Growth Factor Prevents Renal Interstitial Fibrosis", J Am Soc Nephrol, 13, (2002), 96-107.

Yang, J., et al., "Hepatocyte Growth Factor Gene Theraphy and Angiotensin II Blockage Synergistically Attenuate Renal Interstitial Fibrosis in Mice", J Am Soc Nephrol, 13, (2002), 2464-2477.

Yilmaz, S., et al., "Evaluating the accuracy of functional biomarkers for detecting histological changes in chronic allograft nephropathy", Transplant International, 20, (2007), 608-615.

Zeisberg, M., et al., "16. Animal models of renal fibrosis", Methods Mol Med, 117, (2005), 261-272.

Zeisberg, M., et al., "Mechanisms of Tubulointerstitial Fibrosis", J Am Soc Nephrol, 21, (2010), 1819-1834.

Anglicheau, D., et al., "MicroRNA expression profiles predictive of human renal allograft status", Proc Natl Acad. Sci USA, 106(13), (2009), 5330-5335.

\* cited by examiner

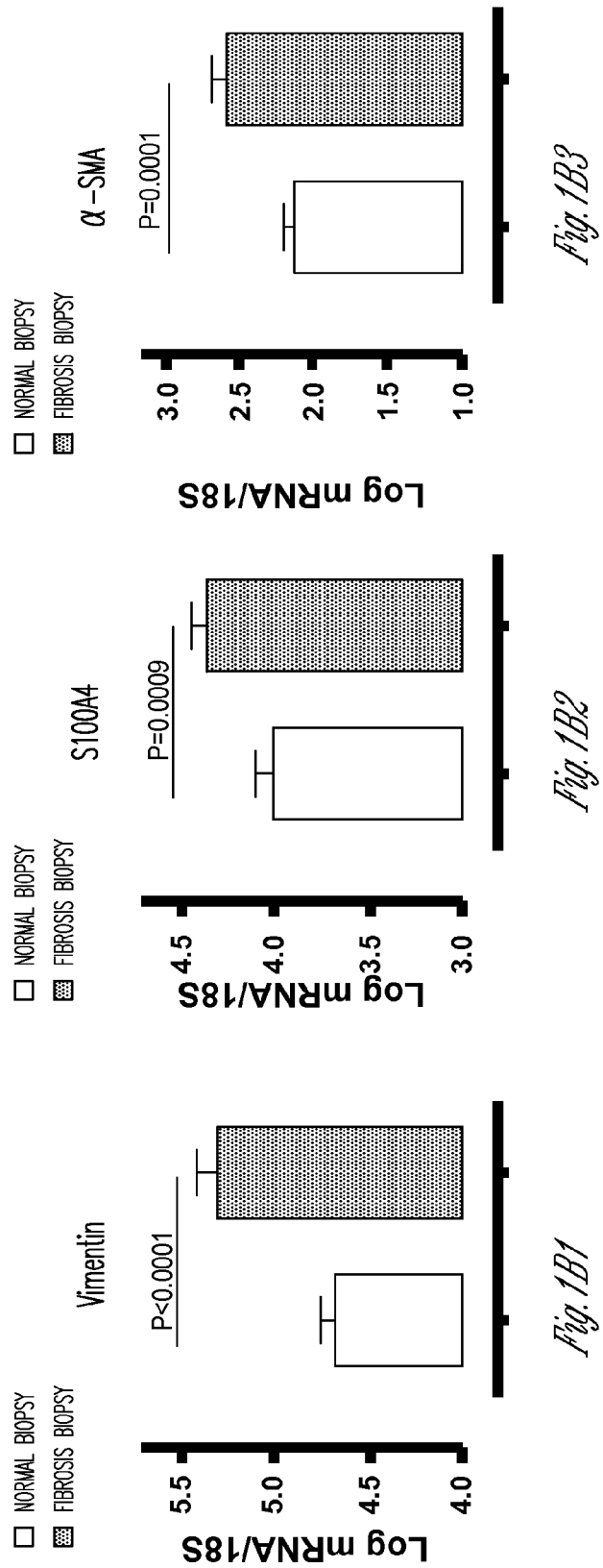

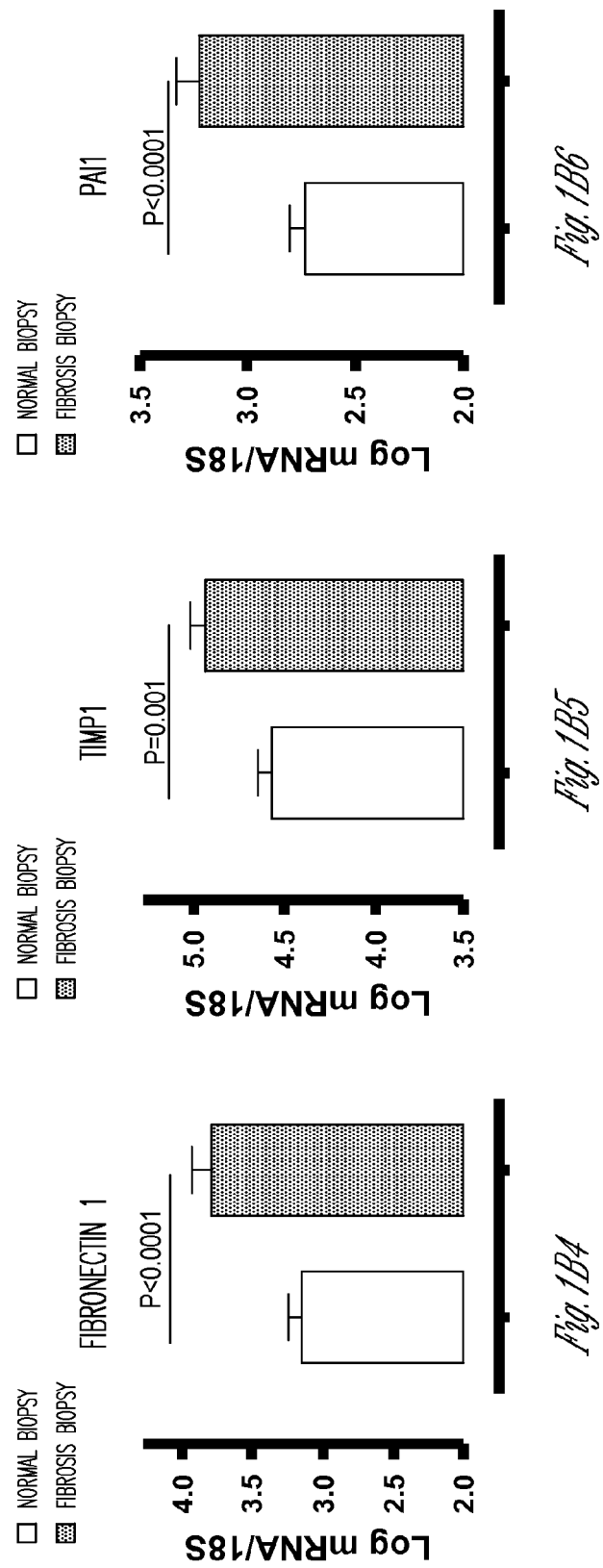
Fig. 1B4  Fig. 1B5  Fig. 1B6

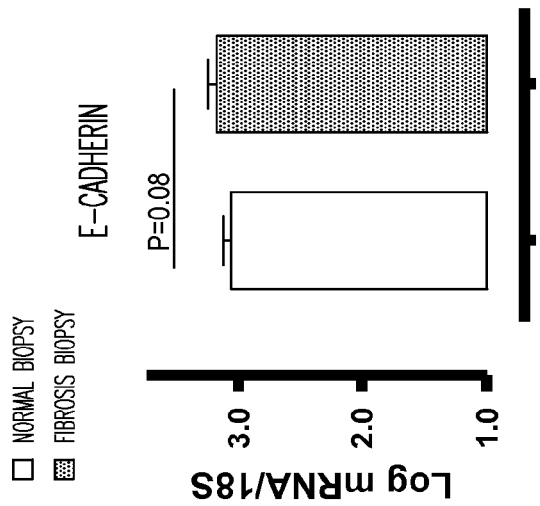
Fig. 1B9
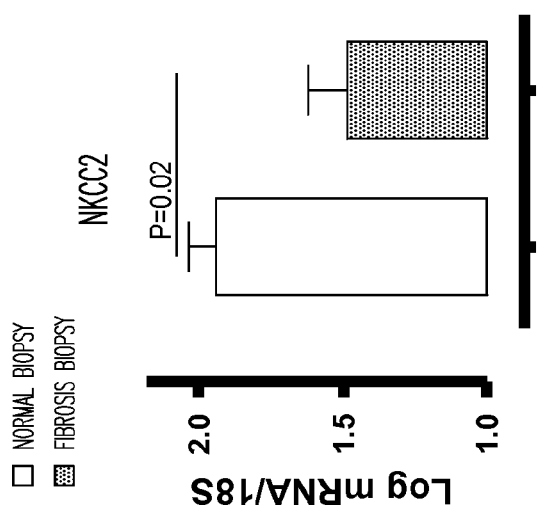
Fig. 1B8
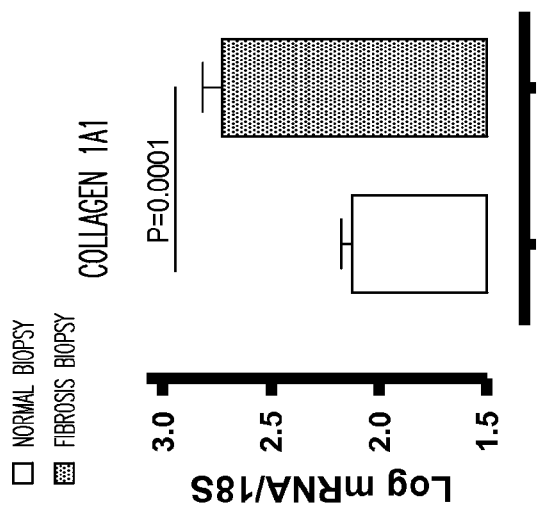
Fig. 1B7

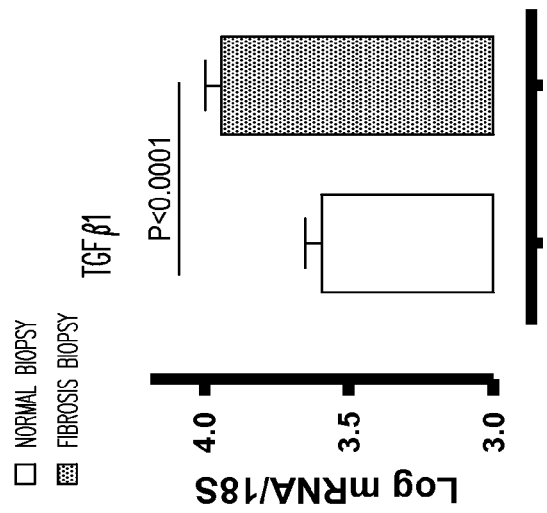
Fig. 1B12
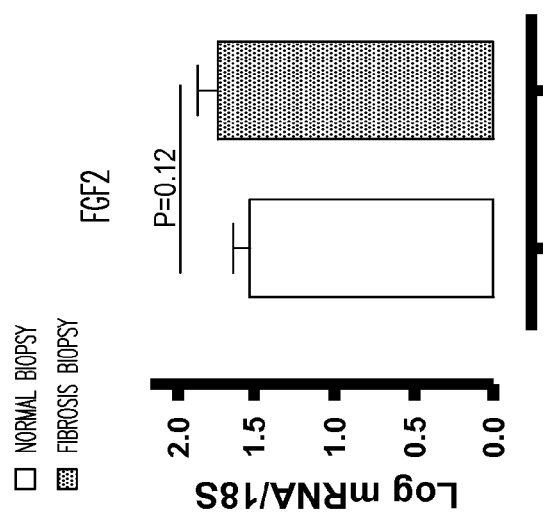
Fig. 1B11
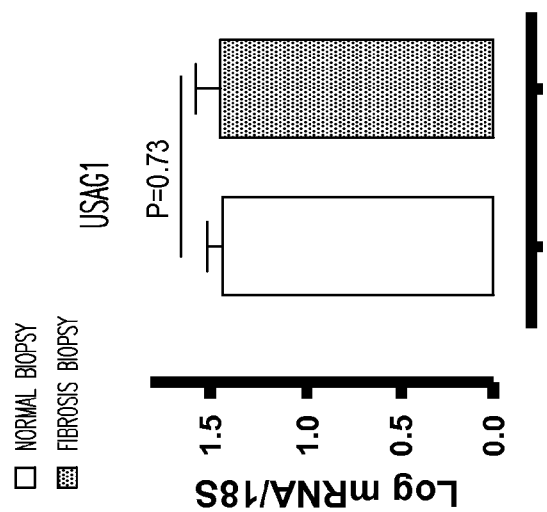
Fig. 1B10

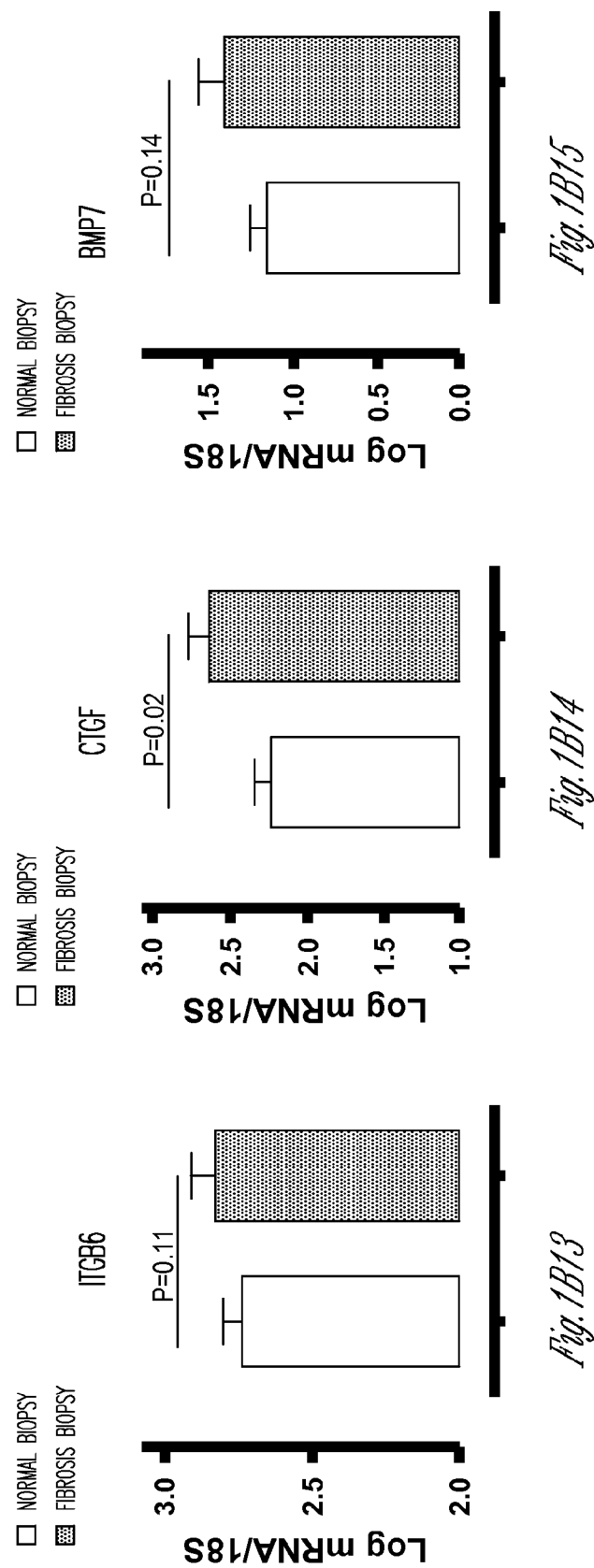
Fig.1B13  Fig.1B14  Fig.1B15

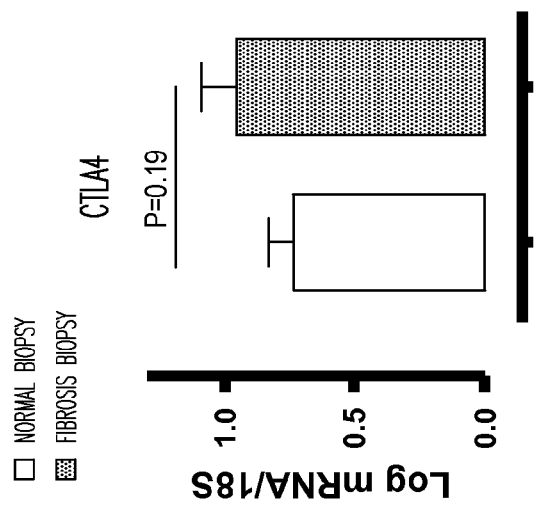
*Fig. 1B18*
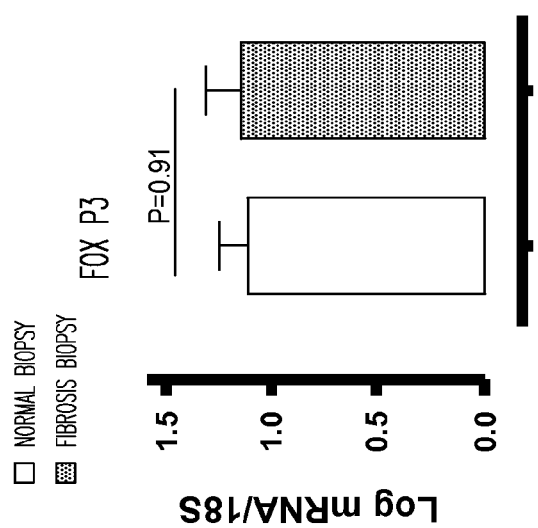
*Fig. 1B17*
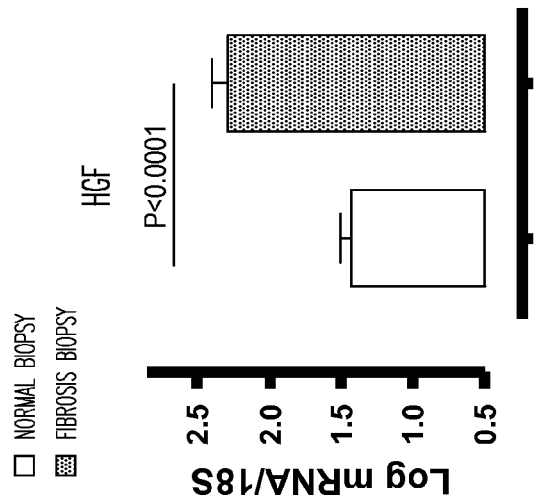
*Fig. 1B16*

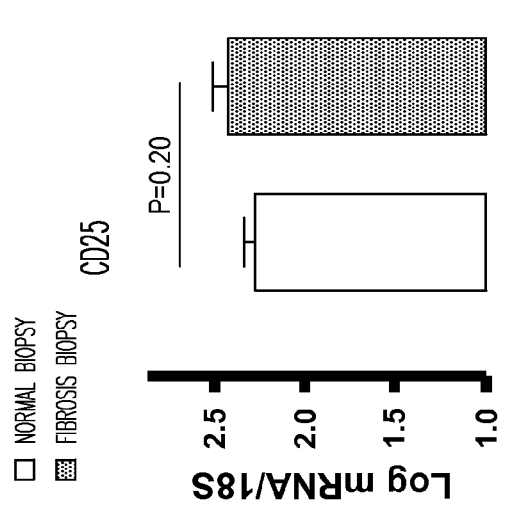
Fig. 1B21
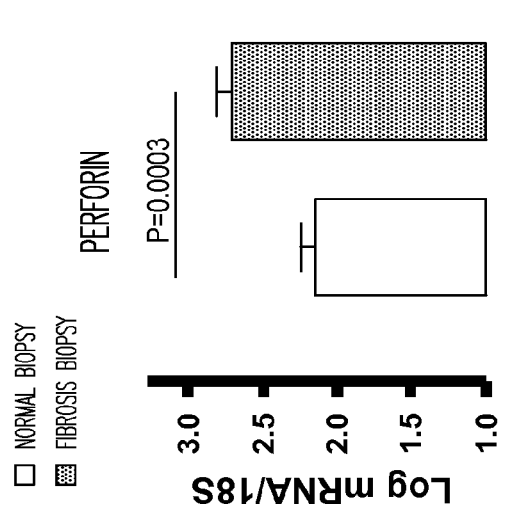
Fig. 1B20
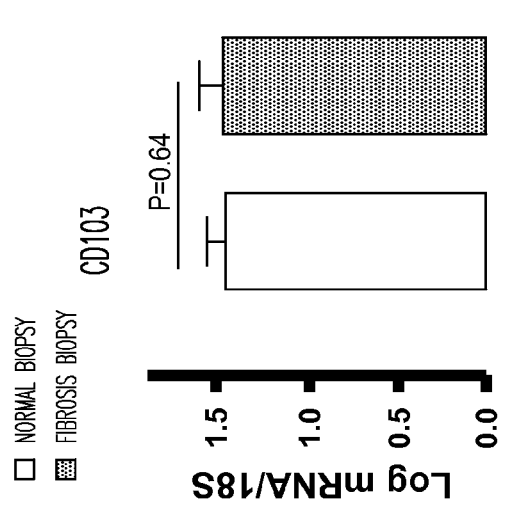
Fig. 1B19

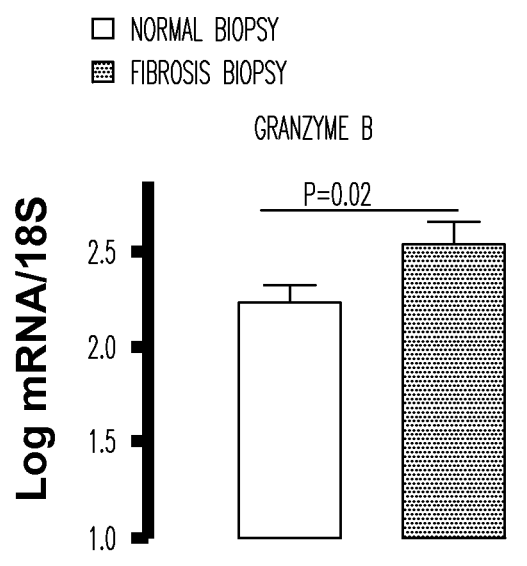
Fig. 1B22

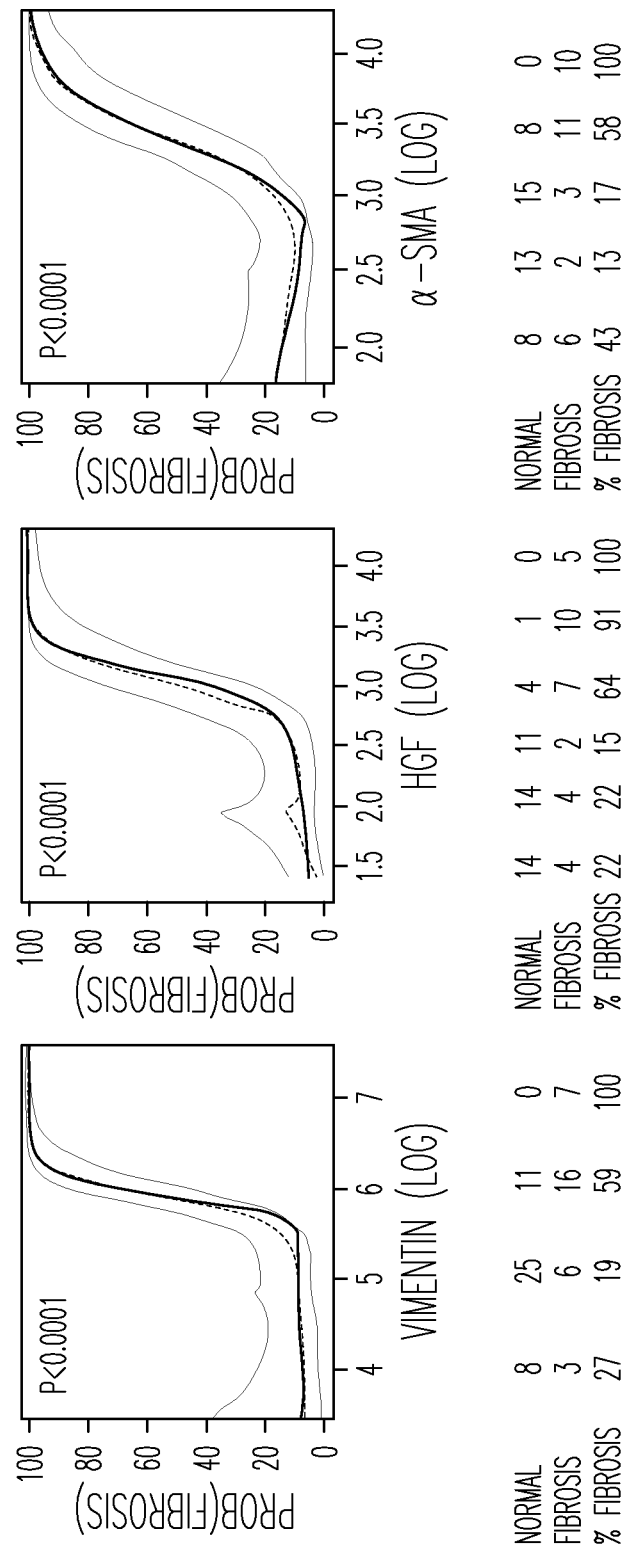

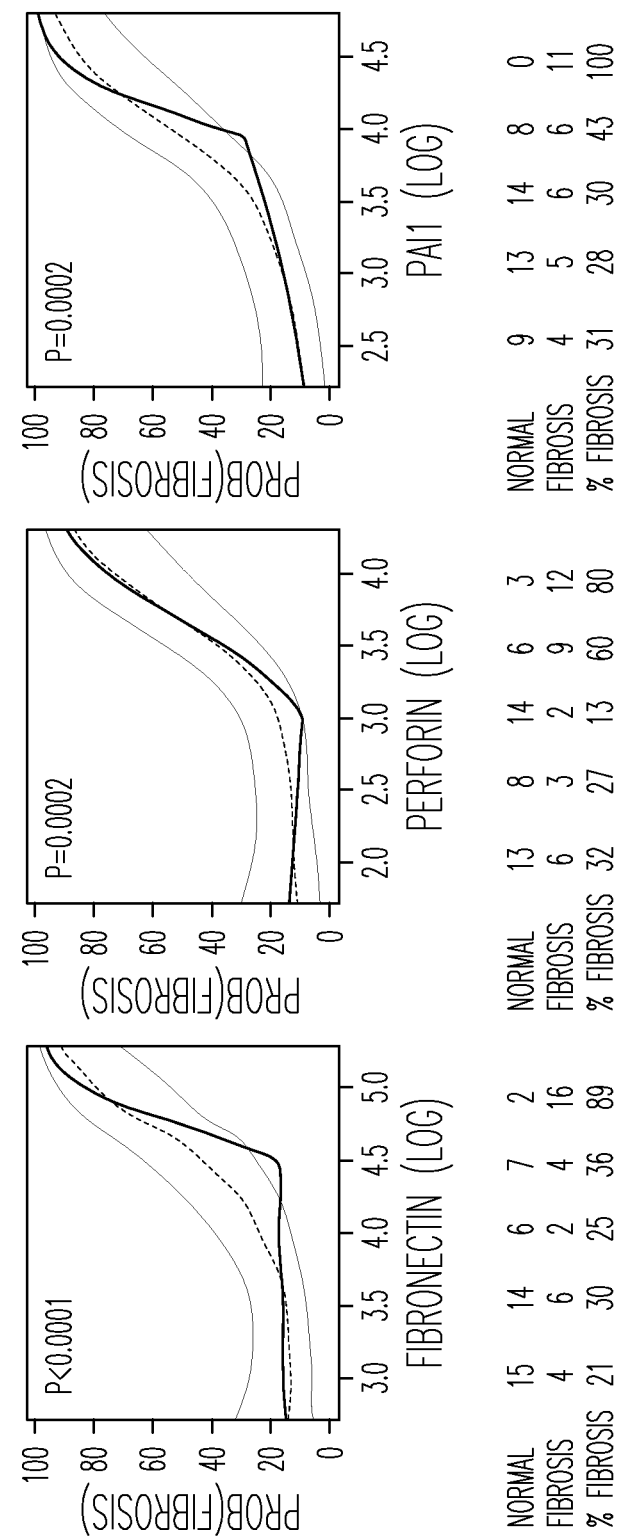
Fig. 2A4   Fig. 2A5   Fig. 2A6

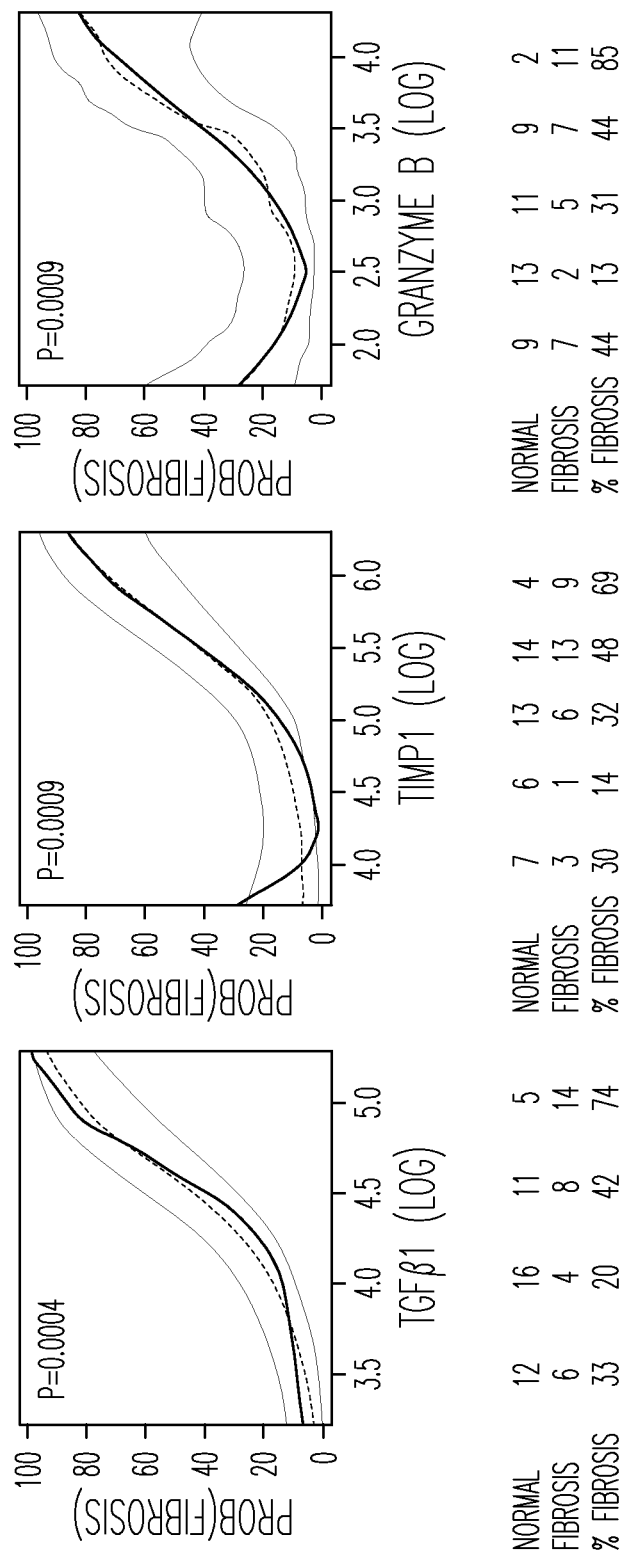
Fig. 2A7, Fig. 2A8, Fig. 2A9

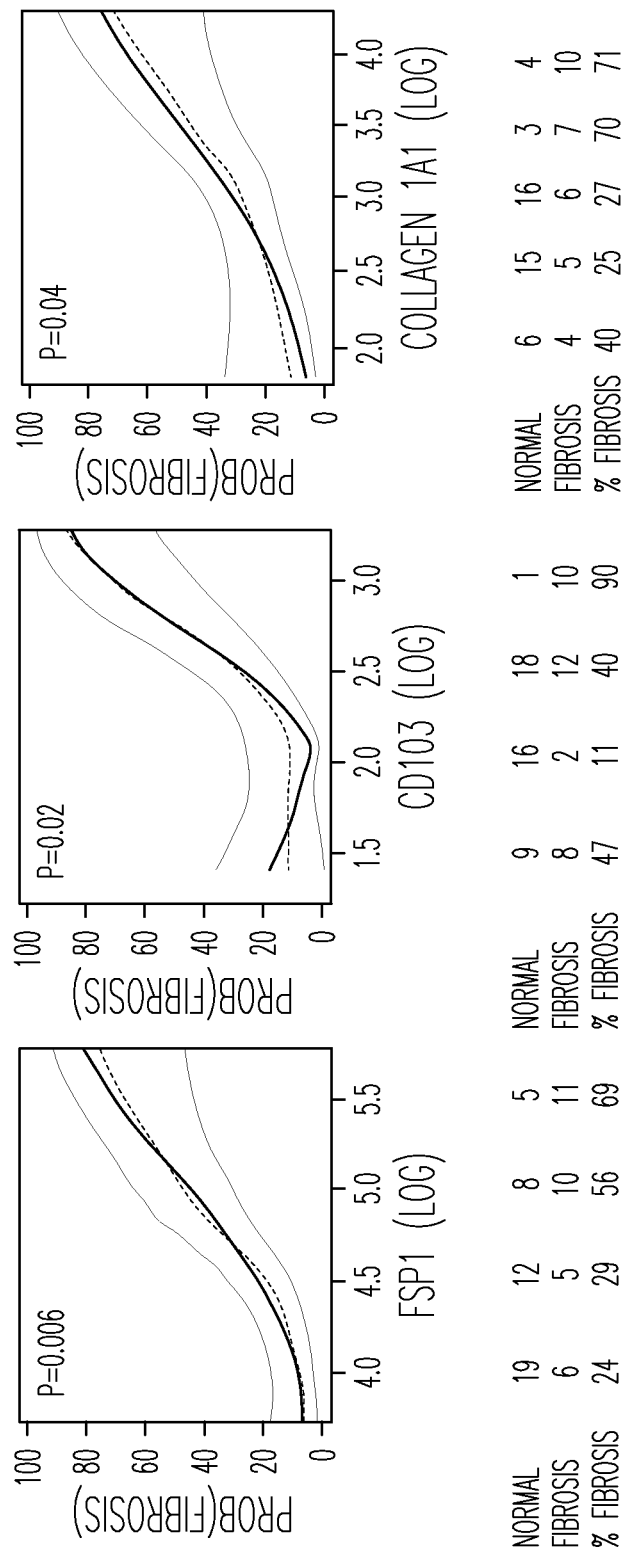
Fig. 2A10    Fig. 2A11    Fig. 2A12

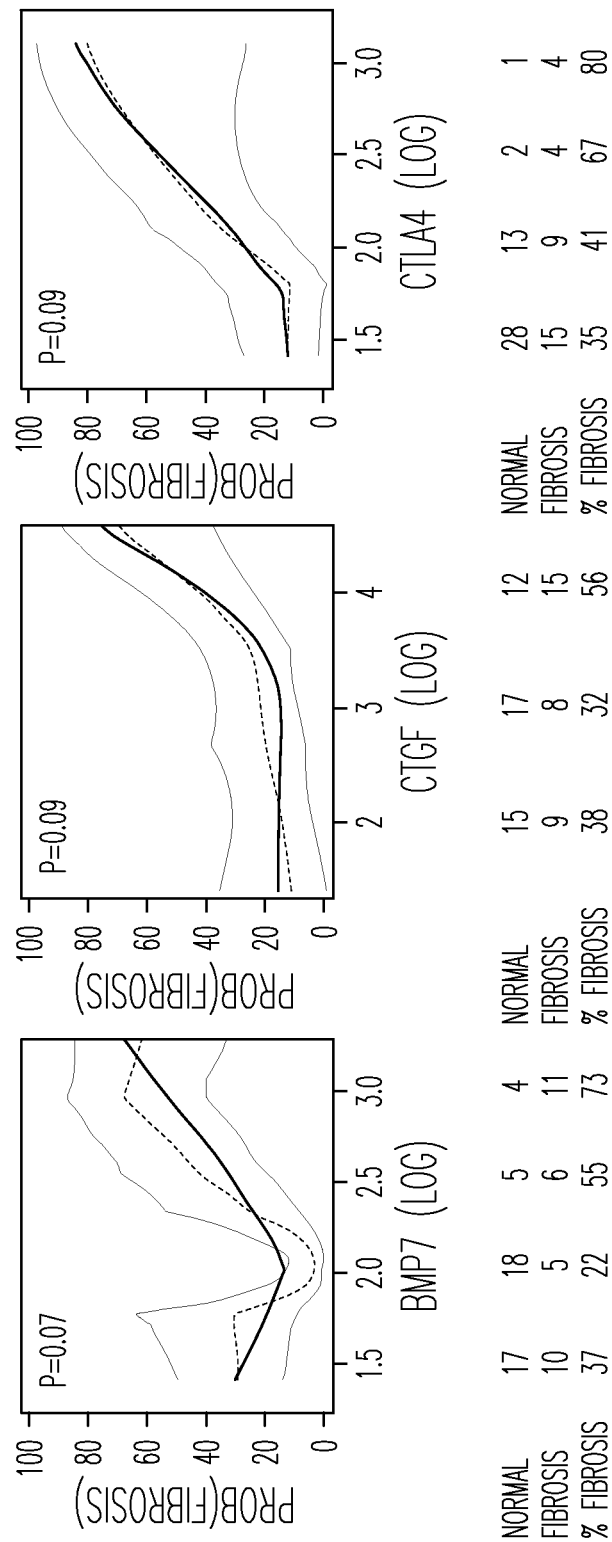
Fig. 2B1   Fig. 2B2   Fig. 2B3

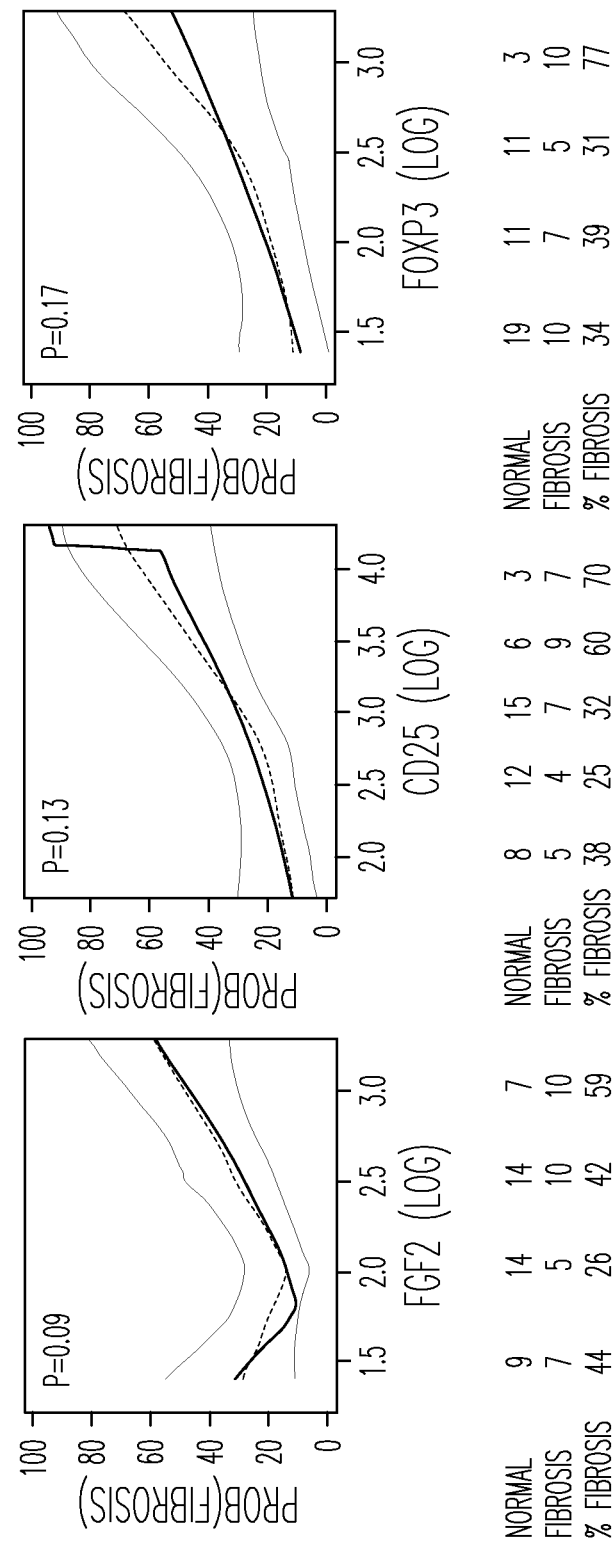
Fig. 2B6
Fig. 2B5
Fig. 2B4

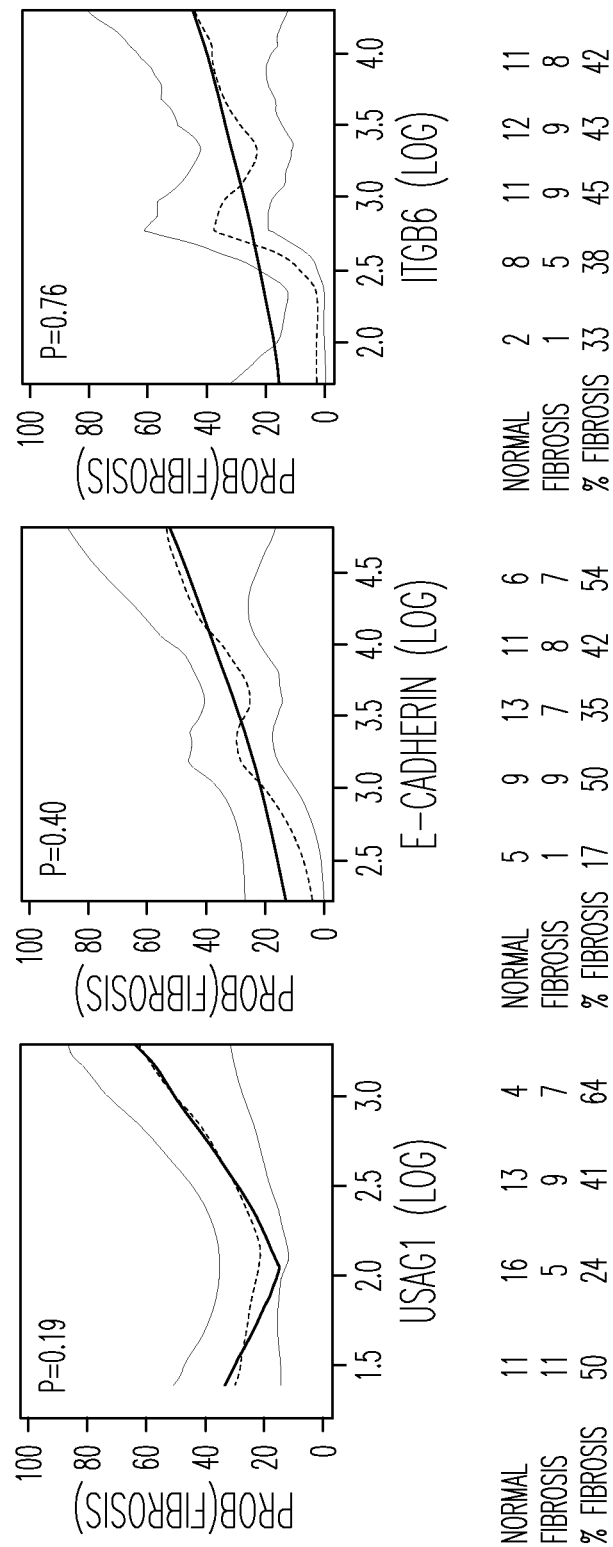
Fig.2B7    Fig.2B8    Fig.2B9

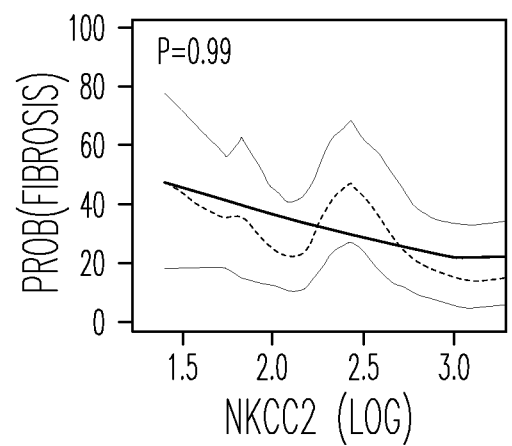
Fig.2B10

| VARIABLE | B | SE | 95%CI | P |
|---|---|---|---|---|
| LOG$_{10}$(18S rRNA) | -15.84 | 7.41 | -30.37 TO -1.31 | 0.03 |
| LOG$_{10}$(18S rRNA)$^2$ | 1.57 | 0.81 | -0.02 TO 3.16 | 0.05 |
| MAX (0, LOG$_{10}$(VIMENTIN)-5.6) | 5.12 | 1.31 | 2.55 TO 7.68 | 0.0001 |
| LOG$_{10}$(NKCC2) | -1.44 | 0.51 | -2.44 TO -0.44 | 0.005 |
| MIN (3.1 LOG$_{10}$(E-CADHERIN)) | 3.31 | 1.44 | 0.49 TO 6.14 | 0.02 |
| CONSTANT | 36.10 | | | |

Fig. 3D

SEQUENCE LISTING

```
<160> NUMBER OF SEQ ID NOS: 80

<210> SEQ ID NO 1
<211> LENGTH: 1847
<212> TYPE: DNA
<213> ORGANISM: Homo sapiens

<400> SEQUENCE: 1
gtccccgcgc cagagacgca gccgcgctcc caccacccac acccaccgcg ccctcgttcg      60
cctcttctcc gggagccagt ccgcgccacc gccgccgccc aggccatcgc caccctccgc     120
agccatgtcc accaggtccg tgtcctcgtc ctcctaccgc aggatgttcg gcggcccggg     180
caccgcgagc cggccgagct ccagccggag ctacgtgact acgtccaccc gcacctacag     240
cctgggcagc gcgctgcgcc ccagcaccag ccgcagcctc tacgcctcgt ccccgggcgg     300
cgtgtatgcc acgcgctcct ctgccgtgcg cctgcggagc agcgtgcccg gggtgcggct     360
cctgcaggac tcggtggact tctcgctggc cgacgccatc aacaccgagt tcaagaacac     420
ccgcaccaac gagaaggtgg agctgcagga gctgaatgac cgcttcgcca actacatcga     480
caaggtgcgc ttcctggagc agcagaataa gatcctgctg gccgagctcg agcagctcaa     540
gggccaaggc aagtcgcgcc tgggggacct ctacgaggag gagatgcggg agctgcgccg     600
gcaggtggac cagctaacca acgacaaagc ccgcgtcgag gtggagcgcg acaacctggc     660
cgaggacatc atgcgcctcc gggagaaatt gcaggaggag atgcttcaga gagaggaagc     720
cgaaaacacc ctgcaatctt tcagacagga tgttgacaat gcgtctctgg cacgtcttga     780
ccttgaacgc aaagtggaat ctttgcaaga agagattgcc ttttgaaga aactccacga     840 agaggaaatc caggagctgc aggctcagat tcaggaacag catgtccaaa tcgatgtgga     900
tgtttccaag cctgacctca cggctgccct gcgtgacgta cgtcagcaat atgaaagtgt     960
ggctgccaag aacctgcagg aggcagaaga atggtacaaa tccaagtttg ctgacctctc    1020
```

```
tgaggctgcc aaccggaaca atgacgccct gcgccaggca aagcaggagt ccactgagta   1080
ccggagacag gtgcagtccc tcacctgtga agtggatgcc cttaaaggaa ccaatgagtc   1140
cctggaacgc cagatgcgtg aaatggaaga gaactttgcc gttgaagctg ctaactacca   1200
agacactatt ggccgcctgc aggatgagat tcagaatatg aaggaggaaa tggctcgtca   1260
ccttcgtgaa taccaagacc tgctcaatgt taagatggcc cttgacattg agattgccac   1320
ctacaggaag ctgctggaag gcgaggagag caggatttct ctgcctcttc caaactttt c  1380 ctccctgaac ctgagggaaa ctaatctgga ttcactccct ctggttgata cccactcaaa   1440
aaggacactt ctgattaaga cggttgaaac tagagatgga caggttatca acgaaacttc   1500
tcagcatcac gatgaccttg aataaaaatt gcacacactc agtgcagcaa tatattacca   1560
gcaagaataa aaagaaatc catatcttaa agaaacagct ttcaagtgcc tttctgcagt   1620
ttttcaggag cgcaagatag atttggaata ggaataagct ctagttctta acaaccgaca   1680
ctcctacaag atttagaaaa aagtttacaa cataatctag tttacagaaa atcttgtgc    1740 tagaatactt tttaaaaggt attttgaata ccattaaaac tgcttttttt tttccagcaa   1800
gtatccaacc aacttggttc tgcttcaata aatctttgga aaaactc                 1847
```

<210> SEQ ID NO 2
<211> LENGTH: 466
<212> TYPE: PRT
<213> ORGANISM: Homo sapiens

<400> SEQUENCE: 2

```
Met Ser Thr Arg Ser Val Ser Ser Ser Tyr Arg Arg Met Phe Gly
1               5                   10                  15

Gly Pro Gly Thr Ala Ser Arg Pro Ser Ser Ser Arg Ser Tyr Val Thr
            20                  25                  30

Thr Ser Thr Arg Thr Tyr Ser Leu Gly Ser Ala Leu Arg Pro Ser Thr
        35                  40                  45

Ser Arg Ser Leu Tyr Ala Ser Ser Pro Gly Gly Val Tyr Ala Thr Arg
    50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
    130                 135                 140

Arg Leu Gly Asp Leu Tyr Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
        195                 200                 205

Asp Val Asp Asn Ala Ser Leu Ala Arg Leu Asp Leu Glu Arg Lys Val
    210                 215                 220
```

Glu Ser Leu Gln Glu Glu Ile Ala Phe Leu Lys Lys Leu His Glu
225                 230                 235                 240

Glu Ile Gln Glu Leu Gln Ala Gln Ile Gln Glu Gln His Val Gln Ile
            245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
            275                 280                 285

Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
            325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
            355                 360                 365

Ile Gln Asn Met Lys Glu Glu Met Ala Arg His Leu Arg Glu Tyr Gln
370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
            405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
            435                 440                 445

Thr Arg Asp Gly Gln Val Ile Asn Glu Thr Ser Gln His His Asp Asp
            450                 455                 460

Leu Glu
465

<210> SEQ ID NO 3
<211> LENGTH: 2151
<212> TYPE: DNA
<213> ORGANISM: Homo sapiens

<400> SEQUENCE: 3
gcctctccaa aggctgcaga agtttcttgc taacaaaaag tccgcacatt cgagcaaaga      60
caggctttag cgagttatta aaaacttagg ggcgctcttg tccccacag ggcccgaccg      120 cacacagcaa ggcgatggcc cagctgtaag ttggtagcac tgagaactag cagcgcgcgc      180
ggagcccgct gagacttgaa tcaatctggt ctaacggttt ccccctaaacc gctaggagcc    240 ctcaatcggc gggacagcag ggcgcgtcct ctgccactct cgctccgagg tcccgcgcc     300 agagacgcag ccgcgctccc accacccaca cccaccgcgc cctcgttcgc ctcttctccg     360
ggagccagtc cgcgccaccg ccgccgccca ggccatcgcc accctccgca gccatgtcca     420
ccaggtccgt gtcctcgtcc tctaccgca ggatgttcgg cggccggggc accgcgagcc      480
ggccgagctc cagccggagc tacgtgacta cgtccacccg cacctacagc ctgggcagcg     540
cgctgcgccc cagcaccagc cgcagcctct acgcctcgtc cccgggcggc gtgtatgcca     600
cgcgctcctc tgccgtgcgc ctgcggagca gcgtgcccgg ggtgcggctc ctgcaggact     660
cggtggactt ctcgctggcc gacgccatca acaccgagtt caagaacacc cgcaccaacg     720

```
agaaggtgga gctgcaggag ctgaatgacc gcttcgccaa ctacatcgac aaggtgcgct    780
tcctggagca gcagaataag atcctgctgg ccgagctcga gcagctcaag ggccaaggca    840
agtcgcgcct gggggacctc tacgaggagg agatgcggga gctgcgccgg caggtggacc    900
agctaaccaa cgacaaagcc cgcgtcgagg tggagcgcga caacctggcc gaggacatca    960
tgcgcctccg ggagaaattg caggaggaga tgcttcagag agaggaagcc gaaaacaccc   1020
tgcaatcttt cagacaggat gttgacaatg cgtctctggc acgtcttgac cttgaacgca   1080
aagtggaatc tttgcaagaa gagattgcct ttttgaagaa actccacgaa gaggaaatcc   1140
aggagctgca ggctcagatt caggaacagc atgtccaaat cgatgtggat gtttccaagc   1200
ctgacctcac ggctgccctg cgtgacgtac gtcagcaata tgaaagtgtg gctgccaaga   1260
acctgcagga ggcagaagaa tggtacaaat ccaagtttgc tgacctctct gaggctgcca   1320
accggaacaa tgacgccctg cgccaggcaa agcaggagtc cactgagtac cggagacagg   1380
tgcagtccct cacctgtgaa gtggatgccc ttaaaggaac caatgagtcc ctggaacgcc   1440
agatgcgtga atggaagag aactttgccg ttgaagctgc taactaccaa gacactattg    1500
gccgcctgca ggatgagatt cagaatatga aggaggaaat ggctcgtcac cttcgtgaat   1560
accaagacct gctcaatgtt aagatggccc ttgacattga gattgccacc tacaggaagc   1620
tgctggaagg cgaggagagc aggatttctc tgcctcttcc aaactttttcc tccctgaacc   1680 tgagggaaac taatctggat tcactccctc tggttgatac ccactcaaaa aggacacttc   1740
tgattaagac ggttgaaact agagatggac aggttatcaa cgaaacttct cagcatcacg   1800
atgaccttga ataaaaattg cacacactca gtgcagcaat atattaccag caagaataaa   1860
aaagaaatcc atatcttaaa gaaacagctt tcaagtgcct ttctgcagtt tttcaggagc   1920
gcaagataga tttggaatag gaataagctc tagttcttaa caaccgacac tcctacaaga   1980
tttagaaaaa agtttacaac ataatctagt ttacagaaaa atcttgtgct agaatacttt   2040
ttaaaaggta ttttgaatac cattaaaact gctttttttt ttccagcaag tatccaacca   2100
acttggttct gcttcaataa atctttggaa aaactcaaaa aaaaaaaaa a              2151
```

<210> SEQ ID NO 4
<211> LENGTH: 464
<212> TYPE: PRT
<213> ORGANISM: Homo sapiens

<400> SEQUENCE: 4

```
Met Ser Thr Arg Ser Val Ser Ser Ser Tyr Arg Arg Met Phe Gly
1               5                   10                  15

Gly Pro Gly Thr Ala Ser Arg Pro Ser Ser Arg Ser Tyr Val Thr
                20                  25                  30

Thr Ser Thr Arg Thr Tyr Ser Leu Gly Ser Ala Leu Arg Pro Ser Thr
        35                  40                  45

Ser Arg Ser Leu Tyr Ala Ser Ser Pro Gly Gly Val Tyr Ala Thr Arg
    50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
```

115                 120                 125
Lys Ile Leu Leu Ala Glu Leu Glu Gln Leu Lys Gly Gln Gly Lys Ser
            130                 135                 140

Arg Leu Gly Asp Leu Tyr Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
            195                 200                 205

Asp Val Asp Asn Ala Ser Leu Ala Arg Leu Asp Leu Glu Arg Lys Val
            210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
            275                 280                 285

Glu Trp Tyr Lys Ser Lys Phe Ala Asp Leu Ser Glu Ala Ala Asn Arg
290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
            355                 360                 365

Ile Gln Asn Met Lys Glu Glu Met Ala Arg His Leu Arg Glu Tyr Gln
370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
            420                 425                 430

Leu Val Asp Thr His Ser Lys Arg Leu Ile Lys Thr Val Glu Thr Arg
            435                 440                 445

Asp Gly Gln Val Ile Asn Glu Thr Ser Gln His His Asp Asp Leu Glu
450                 455                 460

<210> SEQ ID NO 5
<211> LENGTH: 1795
<212> TYPE: DNA
<213> ORGANISM: Homo sapiens

<400> SEQUENCE: 5
ctttgaagaa catcctgaag attatatcgg agacaatata tcaagaatct atttattgaa        60
tcatctagaa caaagccag gagctccta atggaagcac attagtgttt attttgatga        120
agaaatatat agattttta aaacaaccac aaagtagata gctcagtaaa aaatcaattt        180

-continued

```
tggaagatgt cactgaacaa ctcttccaat gtatttctgg attcagtgcc cagtaatacc    240
aatcgctttc aagttagtgt cataaatgag aaccatgaga gcagtgcagc tgcagatgac    300
aatactgacc caccacatta tgaagaaacc tcttttgggg atgaagctca gaaaagactc    360
agaatcagct ttaggcctgg gaatcaggag tgctatgaca atttcctcca agtggagaa     420
actgctaaaa cagatgccag ttttcacgct tatgattctc acacaaacac atactatcta    480
caaacttttg ccacaacac catggatgcc gttcccaaga tagagtacta tcgtaacacc     540
ggcagcatca gtgggcccaa ggtcaaccga cccagcctgc ttgagattca cgagcaactc    600
gcaaagaatg tggcagtcac cccaagttca gctgacagag ttgctaacgg tgatgggata    660
cctggagatg aacaagctga aaataaggaa gatgatcaag ctggtgttgt gaagtttgga    720
tgggtgaaag tgtgctggt aagatgcatg ctgaacatct ggggagtcat gctcttcatt     780
cgcctctcct ggattgttgg agaagctgga attggtcttg gagttctcat aattcttctt    840
tccaccatgg taacttctat tactgggttg tcaacttctg cgatagcaac taacgggttt    900
gttcgtggag gtggggccta ctatcttatt tccagaagtt tagggcccga gttcggtggg    960
tcaataggcc tgatctttgc tttttgctaat gcagtggctg ttgctatgta tgtggtggga   1020
tttgctgaga ctgtagtaga tcttcttaag gagagtgatt cgatgatggt ggatccaacc   1080
aatgacatcc ggattatagg ctccatcaca gtggtgattc ttctaggaat ttcagtagct   1140
ggaatggaat gggaggcaaa ggcccaagtc attcttctgg tcattcttct aattgctatt   1200
gcaaacttct tcattggaac tgtcattcca tccaacaatg agaaaaagtc cagaggtttc   1260
tttaattacc aagcatcaat atttgcagaa aactttgggc cacgcttcac aaagggtgaa   1320
ggcttcttct ctgtctttgc cattttttc ccagcagcta ctgggattct tgctggtgcc    1380
aatatctcag agagtttgga ggcactgagg aaacaaggag cttcacctct ccctcaagga   1440
gctcagagtc gaaggaggag acagacttcc cttatatgaa ttagaacaag caagagtaga   1500
atcaagtgca aaggaaagag gaagcagaaa ttgcctgtcc cctcaaaaag taaggaaga    1560
ctttcagaag aggggacact caatccaggt tttgagggat gaacaggagt ttgccgacag   1620
gacaaagaag agacggacat ttgaaacaga aggaatggga tgtaagaagg caccaagaaa   1680
gatgctgcta atgagaatta ttttatgtgc agagtagtgt atgtaatcct tcattaatat   1740
attaataaac atatttataa ataaaaaaaa aaaaaaaaaa aaaaaaaaaa aaaaa         1795
```

<210> SEQ ID NO 6
<211> LENGTH: 430
<212> TYPE: PRT
<213> ORGANISM: Homo sapiens

<400> SEQUENCE: 6

```
Met Ser Leu Asn Asn Ser Ser Asn Val Phe Leu Asp Ser Val Pro Ser
1               5                   10                  15

Asn Thr Asn Arg Phe Gln Val Ser Val Ile Asn Glu Asn His Glu Ser
            20                  25                  30

Ser Ala Ala Ala Asp Asp Asn Thr Asp Pro Pro His Tyr Glu Glu Thr
        35                  40                  45

Ser Phe Gly Asp Glu Ala Gln Lys Arg Leu Arg Ile Ser Phe Arg Pro
    50                  55                  60

Gly Asn Gln Glu Cys Tyr Asp Asn Phe Leu Gln Ser Gly Glu Thr Ala
65                  70                  75                  80

Lys Thr Asp Ala Ser Phe His Ala Tyr Asp Ser His Thr Asn Thr Tyr
                85                  90                  95
```

Tyr Leu Gln Thr Phe Gly His Asn Thr Met Asp Ala Val Pro Lys Ile
            100                 105                 110

Glu Tyr Tyr Arg Asn Thr Gly Ser Ile Ser Gly Pro Lys Val Asn Arg
        115                 120                 125

Pro Ser Leu Leu Glu Ile His Glu Gln Leu Ala Lys Asn Val Ala Val
    130                 135                 140

Thr Pro Ser Ser Ala Asp Arg Val Ala Asn Gly Asp Gly Ile Pro Gly
145                 150                 155                 160

Asp Glu Gln Ala Glu Asn Lys Glu Asp Gln Ala Gly Val Val Lys
                165                 170                 175

Phe Gly Trp Val Lys Gly Val Leu Val Arg Cys Met Leu Asn Ile Trp
            180                 185                 190

Gly Val Met Leu Phe Ile Arg Leu Ser Trp Ile Val Gly Glu Ala Gly
        195                 200                 205

Ile Gly Leu Gly Val Leu Ile Ile Leu Leu Ser Thr Met Val Thr Ser
    210                 215                 220

Ile Thr Gly Leu Ser Thr Ser Ala Ile Ala Thr Asn Gly Phe Val Arg
225                 230                 235                 240

Gly Gly Gly Ala Tyr Tyr Leu Ile Ser Arg Ser Leu Gly Pro Glu Phe
                245                 250                 255

Gly Gly Ser Ile Gly Leu Ile Phe Ala Phe Ala Asn Ala Val Ala Val
            260                 265                 270

Ala Met Tyr Val Val Gly Phe Ala Glu Thr Val Val Asp Leu Leu Lys
        275                 280                 285

Glu Ser Asp Ser Met Met Val Asp Pro Thr Asn Asp Ile Arg Ile Ile
    290                 295                 300

Gly Ser Ile Thr Val Val Ile Leu Leu Gly Ile Ser Val Ala Gly Met
305                 310                 315                 320

Glu Trp Glu Ala Lys Ala Gln Val Ile Leu Leu Val Ile Leu Leu Ile
                325                 330                 335

Ala Ile Ala Asn Phe Phe Ile Gly Thr Val Ile Pro Ser Asn Asn Glu
            340                 345                 350

Lys Lys Ser Arg Gly Phe Phe Asn Tyr Gln Ala Ser Ile Phe Ala Glu
        355                 360                 365

Asn Phe Gly Pro Arg Phe Thr Lys Gly Glu Gly Phe Phe Ser Val Phe
    370                 375                 380

Ala Ile Phe Phe Pro Ala Ala Thr Gly Ile Leu Ala Gly Ala Asn Ile
385                 390                 395                 400

Ser Gly Asp Leu Glu Ala Leu Arg Lys Gln Gly Ala Ser Pro Leu Pro
                405                 410                 415

Gln Gly Ala Gln Ser Arg Arg Arg Gln Thr Ser Leu Ile
            420                 425                 430

<210> SEQ ID NO 7
<211> LENGTH: 2557
<212> TYPE: DNA
<213> ORGANISM: Homo sapiens

<400> SEQUENCE: 7
agtgaatttt gaagattgca ccggtcgaca aggacagcc tatttttccc tcgacacccg      60
attcaaagtg ggcacagatg gtgtgattac agtcaaaagg cctctacggt ttcataaccc     120
acagatccat ttcttggtct acgcctggga ctccacctac agaaagtttt ccaccaaagt     180
cacgctgaat acagtggggc accaccaccg cccccgccc catcaggcct ccgtttctgg     240

-continued

```
aatccaagca gaattgctca catttcccaa ctcctctcct ggcctcagaa gacagaagag    300
agactgggtt attcctccca tcagctgccc agaaaatgaa aaaggcccat ttcctaaaaa    360
cctggttcag atcaaatcca acaaagacaa agaaggcaag gttttctaca gcatcactgg    420
ccaaggagct gacacacccc ctgttggtgt ctttattatt gaaagagaaa caggatggct    480
gaaggtgaca gagcctctgg atagagaacg cattgccaca tacactctct tctctcacgc    540
tgtgtcatcc aacgggaatg cagttgagga tccaatggag attttgatca cggtaaccga    600
tcagaatgac aacaagcccg aattcaccca ggaggtcttt aaggggtctg tcatggaagg    660
tgctcttcca ggaaccctg tgatggaggt cacagccaca gacgcggacg atgatgtgaa    720
cacctacaat gccgccatcg cttacaccat cctcagccaa gatcctgagc tccctgacaa    780
aaatatgttc accattaaca ggaacacagg agtcatcagt gtggtcacca ctgggctgga    840
ccgagagagt ttccctacgt atacctggt ggttcaagct gctgaccttc aaggtgaggg    900
gttaagcaca acagcaacag ctgtgatcac agtcactgac accaacgata atcctccgat    960
cttcaatccc accacgtaca agggtcaggt gcctgagaac gaggctaacg tcgtaatcac   1020
cacactgaaa gtgactgatg ctgatgcccc caataccca gcgtgggagg ctgtatacac   1080
catattgaat gatgatggtg acaatttgt cgtcaccaca aatccagtga caacgatgg   1140 cattttgaaa acagcaaagg gcttggattt tgaggccaag cagcagtaca ttctacacgt   1200
agcagtgacg aatgtggtac cttttgaggt ctctctcacc acctccacag ccaccgtcac   1260
cgtggatgtg ctggatgtga atgaagcccc catctttgtg cctcctgaaa agagagtgga   1320
agtgtccgag gactttggcg tgggccagga aatcacatcc tacactgccc aggagccaga   1380
cacatttatg gaacagaaaa taacatatcg gatttggaga gacactgcca actggctgga   1440
gattaatccg gacactggtg ccatttccac tcgggctgag ctggacaggg aggattttga   1500
gcacgtgaag aacagcacgt acacagccct aatcatagct acagacaatg ttctccagt   1560 tgctactgga acagggacac ttctgctgat cctgtctgat gtgaatgaca acgcccccat   1620
accagaacct cgaactatat tcttctgtga gaggaatcca aagcctcagg tcataaacat   1680
cattgatgca gaccttcctc ccaatacatc tcccttcaca gcagaactaa cacacggggc   1740
gagtgccaac tggaccattc agtacaacga cccaacccaa gaatctatca ttttgaagcc   1800
aaagatggcc ttagaggtgg gtgactacaa aatcaatctc aagctcatgg ataaccagaa   1860
taaagaccaa gtgaccaccct tagaggtcag cgtgtgtgac tgtgaagggg ccgctggcgt   1920
ctgtaggaag gcacagcctg tcgaagcagg attgcaaatt cctgccattc tggggattct   1980
tggaggaatt cttgctttgc taattctgat tctgctgctc ttgctgtttc ttcggaggag   2040
agcggtggtc aaagagccct tactgccccc agaggatgac acccgggaca acgtttatta   2100
ctatgatgaa gaggaggcg gagaagagga ccaggacttt gacttgagcc agctgcacag   2160
gggcctggac gctcggcctg aagtgactcg taacgacgtt gcaccaaccc tcatgagtgt   2220
cccccggtat cttccccgcc ctgccaatcc cgatgaaatt ggaaatttta ttgatgaaaa   2280
tctgaaagcg gctgatactg accccacagc cccgccttat gattctctgc tcgtgtttga   2340
ctatgaagga agcggttccg aagctgctag tctgagctcc ctgaactcct cagagtcaga   2400
caaagaccag gactatgact acttgaacga atggggcaat cgcttcaaga agctggctga   2460
catgtacggc ggcggcgagg acgactaggg gactcgagag aggcgggccc cagacccatg   2520
tgctgggaaa tgcagaaatc acgttgctgg tggtttt                            2557
```

<210> SEQ ID NO 8
<211> LENGTH: 637
<212> TYPE: PRT
<213> ORGANISM: Homo sapiens

<400> SEQUENCE: 8

```
Met Glu Ile Leu Ile Thr Val Thr Asp Gln Asn Asp Asn Lys Pro Glu
1               5                   10                  15

Phe Thr Gln Glu Val Phe Lys Gly Ser Val Met Glu Gly Ala Leu Pro
            20                  25                  30

Gly Thr Ser Val Met Glu Val Thr Ala Thr Asp Ala Asp Asp Asp Val
        35                  40                  45

Asn Thr Tyr Asn Ala Ala Ile Ala Tyr Thr Ile Leu Ser Gln Asp Pro
    50                  55                  60

Glu Leu Pro Asp Lys Asn Met Phe Thr Ile Asn Arg Asn Thr Gly Val
65                  70                  75                  80

Ile Ser Val Val Thr Thr Gly Leu Asp Arg Glu Ser Phe Pro Thr Tyr
                85                  90                  95

Thr Leu Val Val Gln Ala Ala Asp Leu Gln Gly Glu Gly Leu Ser Thr
            100                 105                 110

Thr Ala Thr Ala Val Ile Thr Val Thr Asp Thr Asn Asp Asn Pro Pro
        115                 120                 125

Ile Phe Asn Pro Thr Thr Tyr Lys Gly Gln Val Pro Glu Asn Glu Ala
    130                 135                 140

Asn Val Val Ile Thr Thr Leu Lys Val Thr Asp Ala Asp Ala Pro Asn
145                 150                 155                 160

Thr Pro Ala Trp Glu Ala Val Tyr Thr Ile Leu Asn Asp Asp Gly Gly
                165                 170                 175

Gln Phe Val Val Thr Thr Asn Pro Val Asn Asn Asp Gly Ile Leu Lys
            180                 185                 190

Thr Ala Lys Gly Leu Asp Phe Glu Ala Lys Gln Gln Tyr Ile Leu His
        195                 200                 205

Val Ala Val Thr Asn Val Val Pro Phe Glu Val Ser Leu Thr Thr Ser
    210                 215                 220

Thr Ala Thr Val Thr Val Asp Val Leu Asp Val Asn Glu Ala Pro Ile
225                 230                 235                 240

Phe Val Pro Pro Glu Lys Arg Val Glu Val Ser Glu Asp Phe Gly Val
                245                 250                 255

Gly Gln Glu Ile Thr Ser Tyr Thr Ala Gln Glu Pro Asp Thr Phe Met
            260                 265                 270

Glu Gln Lys Ile Thr Tyr Arg Ile Trp Arg Asp Thr Ala Asn Trp Leu
        275                 280                 285

Glu Ile Asn Pro Asp Thr Gly Ala Ile Ser Thr Arg Ala Glu Leu Asp
    290                 295                 300

Arg Glu Asp Phe Glu His Val Lys Asn Ser Thr Tyr Thr Ala Leu Ile
305                 310                 315                 320

Ile Ala Thr Asp Asn Gly Ser Pro Val Ala Thr Gly Thr Gly Thr Leu
                325                 330                 335

Leu Leu Ile Leu Ser Asp Val Asn Asp Asn Ala Pro Ile Pro Glu Pro
            340                 345                 350

Arg Thr Ile Phe Phe Cys Glu Arg Asn Pro Lys Pro Gln Val Ile Asn
        355                 360                 365

Ile Ile Asp Ala Asp Leu Pro Pro Asn Thr Ser Pro Phe Thr Ala Glu
    370                 375                 380
```

Leu Thr His Gly Ala Ser Ala Asn Trp Thr Ile Gln Tyr Asn Asp Pro
385                 390                 395                 400

Thr Gln Glu Ser Ile Ile Leu Lys Pro Lys Met Ala Leu Glu Val Gly
            405                 410                 415

Asp Tyr Lys Ile Asn Leu Lys Leu Met Asp Asn Gln Asn Lys Asp Gln
            420                 425                 430

Val Thr Thr Leu Glu Val Ser Val Cys Asp Cys Glu Gly Ala Ala Gly
        435                 440                 445

Val Cys Arg Lys Ala Gln Pro Val Glu Ala Gly Leu Gln Ile Pro Ala
    450                 455                 460

Ile Leu Gly Ile Leu Gly Gly Ile Leu Ala Leu Ile Leu Ile Leu Leu
465                 470                 475                 480

Leu Leu Leu Leu Phe Leu Arg Arg Arg Ala Val Val Lys Glu Pro Leu
                485                 490                 495

Leu Pro Pro Glu Asp Asp Thr Arg Asp Asn Val Tyr Tyr Tyr Asp Glu
            500                 505                 510

Glu Gly Gly Gly Glu Glu Asp Gln Asp Phe Asp Leu Ser Gln Leu His
        515                 520                 525

Arg Gly Leu Asp Ala Arg Pro Glu Val Thr Arg Asn Asp Val Ala Pro
    530                 535                 540

Thr Leu Met Ser Val Pro Arg Tyr Leu Pro Arg Pro Ala Asn Pro Asp
545                 550                 555                 560

Glu Ile Gly Asn Phe Ile Asp Glu Asn Leu Lys Ala Ala Asp Thr Asp
                565                 570                 575

Pro Thr Ala Pro Pro Tyr Asp Ser Leu Leu Val Phe Asp Tyr Glu Gly
            580                 585                 590

Ser Gly Ser Glu Ala Ala Ser Leu Ser Ser Leu Asn Ser Ser Glu Ser
        595                 600                 605

Asp Lys Asp Gln Asp Tyr Asp Tyr Leu Asn Glu Trp Gly Asn Arg Phe
    610                 615                 620

Lys Lys Leu Ala Asp Met Tyr Gly Gly Gly Glu Asp Asp
625                 630                 635

<210> SEQ ID NO 9
<211> LENGTH: 4815
<212> TYPE: DNA
<213> ORGANISM: Homo sapiens

<400> SEQUENCE: 9
agtggcgtcg gaactgcaaa gcacctgtga gcttgcggaa gtcagttcag actccagccc    60
gctccagccc ggcccgaccc gaccgcaccc ggcgcctgcc ctcgctcggc gtccccggcc   120
agccatgggc ccttggagcc gcagcctctc ggcgctgctg ctgctgctgc aggtctcctc   180
ttggctctgc caggagccgg agccctgcca ccctggcttt gacgccgaga gctacacgtt   240
cacggtgccc cggcgccacc tggagagagg ccgcgtcctg ggcagagtga attttgaaga   300
ttgcaccggt cgacaaagga cagcctattt ttccctcgac acccgattca agtgggcac    360 agatggtgtg attacagtca aaaggcctct acggtttcat aacccacaga tccatttctt   420
ggtctacgcc tgggactcca cctacagaaa gttttccacc aaagtcacgc tgaatacagt   480
ggggcaccac caccgccccc cgccccatca ggcctccgtt tctggaatcc aagcagaatt   540
gctcacattt cccaactcct ctcctggcct cagaagacag aagagagact gggttattcc   600
tcccatcagc tgcccagaaa atgaaaaagg cccatttcct aaaaacctgg ttcagatcaa   660

```
atccaacaaa gacaaagaag gcaaggtttt ctacagcatc actggccaag gagctgacac      720
accccctgtt ggtgtcttta ttattgaaag agaaacagga tggctgaagg tgacagagcc      780
tctggataga gaacgcattg ccacatacac tctcttctct cacgctgtgt catccaacgg      840
gaatgcagtt gaggatccaa tggagatttt gatcacggta accgatcaga atgcaacaa       900 gcccgaattc acccaggagg tctttaaggg gtctgtcatg gaaggtgctc ttccaggaac      960
ctctgtgatg gaggtcacag ccacagacgc ggacgatgat gtgaacacct acaatgccgc     1020
catcgcttac accatcctca gccaagatcc tgagctccct gacaaaaata tgttcaccat     1080
taacaggaac acaggagtca tcagtgtggt caccactggg ctggaccgag agagtttccc     1140
tacgtatacc ctggtggttc aagctgctga ccttcaaggt gaggggttaa gcacaacagc     1200
aacagctgtg atcacagtca ctgacaccaa cgataatcct ccgatcttca atcccaccac     1260
gtacaagggt caggtgcctg agaacgaggc taacgtcgta atcaccacac tgaaagtgac     1320
tgatgctgat gcccccaata cccccagcgtg ggaggctgta tacaccatat tgaatgatga     1380
tggtggacaa tttgtcgtca ccacaaatcc agtgaacaac gatggcattt tgaaaacagc     1440
aaagggcttg gattttgagg ccaagcagca gtacattcta cacgtagcag tgacgaatgt     1500
ggtacctttt gaggtctctc tcaccacctc cacagccacc gtcaccgtgg atgtgctgga     1560
tgtgaatgaa gcccccatct ttgtgcctcc tgaaaagaga gtggaagtgt ccgaggactt     1620
tggcgtgggc caggaaatca catcctacac tgcccaggag ccagacacat ttatggaaca     1680
gaaaataaca tatcggattt ggagagacac tgccaactgg ctggagatta atccggacac     1740
tggtgccatt tccactcggg ctgagctgga caggaggat tttgagcacg tgaagaacag     1800
cacgtacaca gccctaatca tagctacaga caatggttct ccagttgcta ctggaacagg     1860
gacacttctg ctgatcctgt ctgatgtgaa tgacaacgcc cccataccag aacctcgaac     1920
tatattcttc tgtgagagga tccaaagcc tcaggtcata acatcattg atgcagacct      1980 tcctcccaat acatctccct tcacagcaga actaacacac ggggcgagtg ccaactggac     2040
cattcagtac aacgacccaa cccaagaatc tatcattttg aagccaaaga tggccttaga     2100
ggtgggtgac tacaaaatca atctcaagct catggataac cagaataaag accaagtgac     2160
caccttagag gtcagcgtgt gtgactgtga aggggccgct ggcgtctgta ggaaggcaca     2220
gcctgtcgaa gcaggattgc aaattcctgc cattctgggg attcttggag gaattcttgc     2280
tttgctaatt ctgattctgc tgctcttgct gtttcttcgg aggagagcgg tggtcaaaga     2340
gcccttactg cccccagagg atgacacccg ggacaacgtt tattactatg atgaagaagg     2400
aggcggagaa gaggaccagg actttgactt gagccagctg cacaggggcc tggacgctcg     2460
gcctgaagtg actcgtaacg acgttgcacc aaccctcatg agtgtccccc ggtatcttcc     2520
ccgccctgcc aatcccgatg aaattggaaa ttttattgat gaaaatctga agcggctga      2580 tactgacccc acagccccgc cttatgattc tctgctcgtg tttgactatg aaggaagcgg     2640
ttccgaagct gctagtctga gctccctgaa ctcctcagag tcagacaaag accaggacta     2700
tgactacttg aacgaatggg gcaatcgctt caagaagctg gctgacatgt acggaggcgg     2760
cgaggacgac tagggactc gagagaggcg ggccccagac ccatgtgctg ggaaatgcag     2820
aaatcacgtt gctggtggtt tttcagctcc cttcccttga gatgagtttc tggggaaaaa     2880
aaagagactg ttagtgatg cagttagtat agctttatac tctctccact ttatagctct      2940
aataagtttg tgttagaaaa gtttcgactt atttcttaaa gctttttttt ttttcccatc     3000
actctttaca tggtggtgat gtccaaaaga tacccaaatt ttaatattcc agaagaacaa     3060
```

```
ctttagcatc agaaggttca cccagcacct tgcagatttt cttaaggaat tttgtctcac    3120
ttttaaaaag aagggagaa gtcagctact ctagttctgt tgttttgtgt atataatttt    3180
ttaaaaaaaa tttgtgtgct tctgctcatt actacactgg tgtgtccctc tgccttttt    3240 tttttttttaa gacagggtct cattctatcg gccaggctgg agtgcagtgg tgcaatcaca    3300
gctcactgca gccttgtcct cccaggctca agctatcctt gcacctcagc ctcccaagta    3360
gctgggacca caggcatgca ccactacgca tgactaattt tttaaatatt tgagacgggg    3420
tctccctgtg ttacccaggc tggtctcaaa ctcctgggct caagtgatcc tcccatcttg    3480
gcctcccaga gtattgggat tacagacatg agccactgca cctgcccagc tccccaactc    3540
cctgccattt tttaagagac agtttcgctc catcgcccag gcctgggatg cagtgatgtg    3600
atcatagctc actgtaacct caaactctgg ggctcaagca gttctcccac cagcctcctt    3660
tttatttttt tgtacagatg gggtcttgct atgttgccca agctggtctt aaactcctgg    3720
cctcaagcaa tccttctgcc ttggcccccc aaagtgctgg gattgtgggc atgagctgct    3780
gtgcccagcc tccatgtttt aatatcaact ctcactcctg aattcagttg ctttgcccaa    3840
gataggagtt ctctgatgca gaaattattg ggctctttta gggtaagaag tttgtgtctt    3900
tgtctggcca catcttgact aggtattgtc tactctgaag acctttaatg gcttccctct    3960
ttcatctcct gagtatgtaa cttgcaatgg gcagctatcc agtgacttgt tctgagtaag    4020
tgtgttcatt aatgtttatt tagctctgaa gcaagagtga tatactccag gacttagaat    4080
agtgcctaaa gtgctgcagc caaagacaga gcggaactat gaaaagtggg cttggagatg    4140
gcaggagagc ttgtcattga gcctggcaat ttagcaaact gatgctgagg atgattgagg    4200
tgggtctacc tcatctctga aaattctgga aggaatggag gagtctcaac atgtgtttct    4260
gacacaagat ccgtggtttg tactcaaagc ccagaatccc caagtgcctg cttttgatga    4320
tgtctacaga aaatgctggc tgagctgaac acatttgccc aattccaggt gtgcacagaa    4380
aaccgagaat attcaaaatt ccaaattttt ttcttaggag caagaagaaa atgtggccct    4440 aaaggggtt agttgagggg taggggtag tgaggatctt gatttggatc tcttttatt    4500 taaatgtgaa tttcaacttt tgacaatcaa agaaaagact tttgttgaaa tagctttact    4560
gtttctcaag tgttttggag aaaaaaatca accctgcaat cacttttttgg aattgtcttg    4620 attttcggc agttcaagct atatcgaata tagttctgtg tagagaatgt cactgtagtt    4680
ttgagtgtat acatgtgtgg gtgctgataa ttgtgtattt tctttggggg tggaaaagga    4740
aaacaattca agctgagaaa agtattctca aagatgcatt tttataaatt ttattaaaca    4800
attttgttaa accat                                                     4815
```

<210> SEQ ID NO 10
<211> LENGTH: 882
<212> TYPE: PRT
<213> ORGANISM: Homo sapiens

<400> SEQUENCE: 10

Met Gly Pro Trp Ser Arg Ser Leu Ser Ala Leu Leu Leu Leu Leu Gln
1               5                   10                  15

Val Ser Ser Trp Leu Cys Gln Glu Pro Glu Pro Cys His Pro Gly Phe
            20                  25                  30

Asp Ala Glu Ser Tyr Thr Phe Thr Val Pro Arg Arg His Leu Glu Arg
        35                  40                  45

Gly Arg Val Leu Gly Arg Val Asn Phe Glu Asp Cys Thr Gly Arg Gln

-continued

```
                50                  55                  60
Arg Thr Ala Tyr Phe Ser Leu Asp Thr Arg Phe Lys Val Gly Thr Asp
 65                  70                  75                  80

Gly Val Ile Thr Val Lys Arg Pro Leu Arg Phe His Asn Pro Gln Ile
                 85                  90                  95

His Phe Leu Val Tyr Ala Trp Asp Ser Thr Tyr Arg Lys Phe Ser Thr
                100                 105                 110

Lys Val Thr Leu Asn Thr Val Gly His His Arg Pro Pro Pro His
            115                 120                 125

Gln Ala Ser Val Ser Gly Ile Gln Ala Glu Leu Leu Thr Phe Pro Asn
130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
                165                 170                 175

Gln Ile Lys Ser Asn Lys Asp Lys Glu Gly Lys Val Phe Tyr Ser Ile
                180                 185                 190

Thr Gly Gln Gly Ala Asp Thr Pro Pro Val Gly Val Phe Ile Ile Glu
            195                 200                 205

Arg Glu Thr Gly Trp Leu Lys Val Thr Glu Pro Leu Asp Arg Glu Arg
210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
                245                 250                 255

Asp Asn Lys Pro Glu Phe Thr Gln Glu Val Phe Lys Gly Ser Val Met
                260                 265                 270

Glu Gly Ala Leu Pro Gly Thr Ser Val Met Glu Val Thr Ala Thr Asp
            275                 280                 285

Ala Asp Asp Asp Val Asn Thr Tyr Asn Ala Ala Ile Ala Tyr Thr Ile
290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
                325                 330                 335

Ser Phe Pro Thr Tyr Thr Leu Val Val Gln Ala Ala Asp Leu Gln Gly
                340                 345                 350

Glu Gly Leu Ser Thr Thr Ala Thr Ala Val Ile Thr Val Thr Asp Thr
            355                 360                 365

Asn Asp Asn Pro Pro Ile Phe Asn Pro Thr Thr Tyr Lys Gly Gln Val
370                 375                 380

Pro Glu Asn Glu Ala Asn Val Val Ile Thr Leu Lys Val Thr Asp
385                 390                 395                 400

Ala Asp Ala Pro Asn Thr Pro Ala Trp Glu Ala Val Tyr Thr Ile Leu
                405                 410                 415

Asn Asp Asp Gly Gly Gln Phe Val Val Thr Asn Pro Val Asn Asn
                420                 425                 430

Asp Gly Ile Leu Lys Thr Ala Lys Gly Leu Asp Phe Glu Ala Lys Gln
            435                 440                 445

Gln Tyr Ile Leu His Val Ala Val Thr Asn Val Val Pro Phe Glu Val
450                 455                 460

Ser Leu Thr Thr Ser Thr Ala Thr Val Thr Val Asp Val Leu Asp Val
465                 470                 475                 480
```

```
Asn Glu Ala Pro Ile Phe Val Pro Pro Glu Lys Arg Val Glu Val Ser
                485                 490                 495

Glu Asp Phe Gly Val Gly Gln Glu Ile Thr Ser Tyr Thr Ala Gln Glu
            500                 505                 510

Pro Asp Thr Phe Met Glu Gln Lys Ile Thr Tyr Arg Ile Trp Arg Asp
            515                 520                 525

Thr Ala Asn Trp Leu Glu Ile Asn Pro Asp Thr Gly Ala Ile Ser Thr
        530                 535                 540

Arg Ala Glu Leu Asp Arg Glu Asp Phe Glu His Val Lys Asn Ser Thr
545                 550                 555                 560

Tyr Thr Ala Leu Ile Ile Ala Thr Asp Asn Gly Ser Pro Val Ala Thr
                565                 570                 575

Gly Thr Gly Thr Leu Leu Leu Ile Leu Ser Asp Val Asn Asp Asn Ala
            580                 585                 590

Pro Ile Pro Glu Pro Arg Thr Ile Phe Phe Cys Glu Arg Asn Pro Lys
            595                 600                 605

Pro Gln Val Ile Asn Ile Ile Asp Ala Asp Leu Pro Pro Asn Thr Ser
        610                 615                 620

Pro Phe Thr Ala Glu Leu Thr His Gly Ala Ser Ala Asn Trp Thr Ile
625                 630                 635                 640

Gln Tyr Asn Asp Pro Thr Gln Glu Ser Ile Ile Leu Lys Pro Lys Met
                645                 650                 655

Ala Leu Glu Val Gly Asp Tyr Lys Ile Asn Leu Lys Leu Met Asp Asn
            660                 665                 670

Gln Asn Lys Asp Gln Val Thr Thr Leu Glu Val Ser Val Cys Asp Cys
        675                 680                 685

Glu Gly Ala Ala Gly Val Cys Arg Lys Ala Gln Pro Val Glu Ala Gly
690                 695                 700

Leu Gln Ile Pro Ala Ile Leu Gly Ile Leu Gly Gly Ile Leu Ala Leu
705                 710                 715                 720

Leu Ile Leu Ile Leu Leu Leu Leu Phe Leu Arg Arg Arg Ala Val
                725                 730                 735

Val Lys Glu Pro Leu Leu Pro Pro Glu Asp Asp Thr Arg Asp Asn Val
            740                 745                 750

Tyr Tyr Tyr Asp Glu Glu Gly Gly Glu Glu Asp Gln Asp Phe Asp
            755                 760                 765

Leu Ser Gln Leu His Arg Gly Leu Asp Ala Arg Pro Glu Val Thr Arg
    770                 775                 780

Asn Asp Val Ala Pro Thr Leu Met Ser Val Pro Arg Tyr Leu Pro Arg
785                 790                 795                 800

Pro Ala Asn Pro Asp Glu Ile Gly Asn Phe Ile Asp Glu Asn Leu Lys
                805                 810                 815

Ala Ala Asp Thr Asp Pro Thr Ala Pro Pro Tyr Asp Ser Leu Leu Val
            820                 825                 830

Phe Asp Tyr Glu Gly Ser Gly Ser Glu Ala Ala Ser Leu Ser Ser Leu
            835                 840                 845

Asn Ser Ser Glu Ser Asp Lys Asp Gln Asp Tyr Asp Tyr Leu Asn Glu
        850                 855                 860

Trp Gly Asn Arg Phe Lys Lys Leu Ala Asp Met Tyr Gly Gly Gly Glu
865                 870                 875                 880

Asp Asp
```

<210> SEQ ID NO 11
<211> LENGTH: 2235
<212> TYPE: DNA
<213> ORGANISM: Homo sapiens
<220> FEATURE:
<221> NAME/KEY: misc_feature
<222> LOCATION: (1)...(2235)
<223> OTHER INFORMATION: n = A,T,C or G

<400> SEQUENCE: 11

| | | | | | |
|---|---|---|---|---|---|
| cgctgctcct | cccgtcgccg | tccgggcccg | tccgtccgtc | cgtccgtcgt | cctcctcgct | 60 |
| nnnncgggge | gccgggcccg | tcctcacngg | ccccgnnnn | ngtccnggcc | cgtcggggcc | 120 |
| tcgccgcgct | ctaccttacc | tacctggttg | atcctgccag | tagcatatgc | ttgtctcaaa | 180 |
| gattaagcca | tgcatgtcta | agtacgcacg | gccggtacag | tgaaactgcg | aatggctcat | 240 |
| taaatcagtt | atggttcctt | tggtcgctcg | ctcctctcct | acttggataa | ctgtggtaat | 300 |
| tctagagcta | atacatgccg | acgggcgctg | acccccttcg | cggggggat | gcgtgcattt | 360 |
| atcagatcaa | aaccaacccg | gtcagcccct | ctccggcccc | ggccgggggg | cgggcgccgg | 420 |
| cggctttggt | gactctagat | aacctcgggc | cgatcgcacg | ccccccgtgg | cggcgacgac | 480 |
| ccattcgaac | gtctgcccta | tcaactttcg | atggtagtcg | ccgtgcctac | catggtgacc | 540 |
| acgggtgacg | gggaatcagg | gttcgattcc | ggagagggag | cctgagaaac | ggctaccaca | 600 |
| tccaaggaag | gcagcaggcg | cgcaaattac | ccactcccga | cccggggagg | tagtgacgaa | 660 |
| aaataacaat | acaggactct | ttcgaggccc | tgtaattgga | atgagtccac | tttaaatcct | 720 |
| ttaacgagga | tccattggag | ggcaagtctg | gtgccagcag | ccgcggtaat | tccagctcca | 780 |
| atagcgtata | ttaaagttgc | tgcagttaaa | aagctcgtag | ttggatcttg | ggagcgggcg | 840 |
| ggcggtccgc | cgcgaggcga | gccaccgccc | gtccccgccc | cttgcctctc | ggcgccccct | 900 |
| cgatgctctt | agctgagtgt | cccgcgggc | ccgaagcgtt | tactttgaaa | aaattagagt | 960 |
| gttcaaagca | ggcccgagcc | gcctggatac | cgcagctagg | aataatggaa | taggaccgcg | 1020 |
| gttctatttt | gttggttttc | ggaactgagg | ccatgattaa | gagggacggc | cggggggcatt | 1080 |
| cgtattgcgc | cgctagaggt | gaaattcctt | ggaccggcgc | aagacggacc | agagcgaaag | 1140 |
| catttgccaa | gaatgttttc | attaatcaag | aacgaaagtc | ggaggttcga | agacgatcag | 1200 |
| ataccgtcgt | agttccgacc | ataaacgatg | ccgaccggcg | atgcggcggc | gttattccca | 1260 |
| tgacccgccg | ggcagcttcc | gggaaaccaa | agtctttggg | ttccgggggg | agtatggttg | 1320 |
| caaagctgaa | acttaaagga | attgacggaa | gggcaccacc | aggagtggag | cctgcggctt | 1380 |
| aatttgactc | aacacgggaa | acctcacccg | gcccggacac | ggacaggatt | gacagattga | 1440 |
| tagctctttc | tcgattccgt | gggtggtggt | gcatggccgt | tcttagttgg | tggagcgatt | 1500 |
| tgtctggtta | attccgataa | cgaacgagac | tctggcatgc | taactagtta | cgcgacccc | 1560 |
| gagcggtcgg | cgtcccccaa | cttcttagag | ggacaagtgg | cgttcagcca | cccgagattg | 1620 |
| agcaataaca | ggtctgtgat | gcccttagat | gtccggggct | gcacgcgcgc | tacactgact | 1680 |
| ggctcagcgt | gtgcctaccc | tacgccggca | ggcgcgggta | acccgttgaa | ccccattcgt | 1740 |
| gatggggatc | ggggattgca | attattcccc | atgaacgagg | aattcccagt | aagtgcgggt | 1800 |
| cataagcttg | cgttgattaa | gtccctgccc | tttgtacaca | ccgcccgtcg | ctactaccga | 1860 |
| ttggatggtt | tagtgaggcc | ctcggatcgg | ccccgccggg | gtcggcccac | ggccctggcg | 1920 |
| gagcgctgag | aagacggtcg | aacttgacta | tctagaggaa | gtaaaagtcg | taacaaggtt | 1980 |
| tccgtaggtg | aacctgcgga | aggatcatta | acggagcccg | gacggcggcc | gcggcggcg | 2040 |

```
ccgcgccgcg cttccctccg cacacccacc ccccaccgc gacggcgcgt gcgggcgggg    2100
ccgtgcccgt tcgttcgctc gctcgttcgt tcgccgcccg gcccggccgc gagagccgag    2160
aactcgggag ggagacgggg gagagagaga gagagagaga gagagagaga gagagagaga    2220
gaaagaaggg cgtgt                                                      2235
```

<210> SEQ ID NO 12
<211> LENGTH: 22
<212> TYPE: DNA
<213> ORGANISM: Homo sapiens

<400> SEQUENCE: 12

```
tcagagagag gaagccgaaa ac                                              22
```

<210> SEQ ID NO 13
<211> LENGTH: 22
<212> TYPE: DNA
<213> ORGANISM: Homo sapiens

<400> SEQUENCE: 13

```
ccagagacgc attgtcaaca tc                                              22
```

<210> SEQ ID NO 14
<211> LENGTH: 18
<212> TYPE: DNA
<213> ORGANISM: Homo sapiens

<400> SEQUENCE: 14

```
ccctgcaatc tttcagac                                                   18
```

<210> SEQ ID NO 15
<211> LENGTH: 21
<212> TYPE: DNA
<213> ORGANISM: Homo sapiens

<400> SEQUENCE: 15

```
caaatgtcag ccctggagtt c                                               21
```

<210> SEQ ID NO 16
<211> LENGTH: 24
<212> TYPE: DNA
<213> ORGANISM: Homo sapiens

<400> SEQUENCE: 16

```
ctgtaggtct ttaccccgat agct                                            24
```

<210> SEQ ID NO 17
<211> LENGTH: 29
<212> TYPE: DNA
<213> ORGANISM: Homo sapiens

<400> SEQUENCE: 17

```
atgataccac acgaacacag cttttttgcc                                       29
```

<210> SEQ ID NO 18
<211> LENGTH: 21
<212> TYPE: DNA
<213> ORGANISM: Homo sapiens

<400> SEQUENCE: 18

```
tgggacgaca tggaaaagat c                                               21
```

```
<210> SEQ ID NO 19
<211> LENGTH: 20
<212> TYPE: DNA
<213> ORGANISM: Homo sapiens

<400> SEQUENCE: 19
cagggtggga tgctcttcag                                              20

<210> SEQ ID NO 20
<211> LENGTH: 31
<212> TYPE: DNA
<213> ORGANISM: Homo sapiens

<400> SEQUENCE: 20
ccactctttc tacaatgagc ttcgtgttgc c                                 31

<210> SEQ ID NO 21
<211> LENGTH: 26
<212> TYPE: DNA
<213> ORGANISM: Homo sapiens

<400> SEQUENCE: 21
gaaagtacac ctgttgtcat tcaaca                                       26

<210> SEQ ID NO 22
<211> LENGTH: 22
<212> TYPE: DNA
<213> ORGANISM: Homo sapiens

<400> SEQUENCE: 22
accttcacgt ctgtcacttc ca                                           22

<210> SEQ ID NO 23
<211> LENGTH: 20
<212> TYPE: DNA
<213> ORGANISM: Homo sapiens

<400> SEQUENCE: 23
ccactggcac cccacgctca                                              20

<210> SEQ ID NO 24
<211> LENGTH: 21
<212> TYPE: DNA
<213> ORGANISM: Homo sapiens

<400> SEQUENCE: 24
aatcagacgg cagcactgtc t                                            21

<210> SEQ ID NO 25
<211> LENGTH: 23
<212> TYPE: DNA
<213> ORGANISM: Homo sapiens

<400> SEQUENCE: 25
gggcgtggtg aactcagtat agt                                          23

<210> SEQ ID NO 26
<211> LENGTH: 15
<212> TYPE: DNA
<213> ORGANISM: Homo sapiens

<400> SEQUENCE: 26
tgtgcccatg atggc                                                   15
```

-continued

<210> SEQ ID NO 27
<211> LENGTH: 23
<212> TYPE: DNA
<213> ORGANISM: Homo sapiens

<400> SEQUENCE: 27
ggaccagtac agcttcagca ctg                                             23

<210> SEQ ID NO 28
<211> LENGTH: 20
<212> TYPE: DNA
<213> ORGANISM: Homo sapiens

<400> SEQUENCE: 28
gccctcttga agtcagggtg                                                 20

<210> SEQ ID NO 29
<211> LENGTH: 30
<212> TYPE: DNA
<213> ORGANISM: Homo sapiens

<400> SEQUENCE: 29
tgccgcttct acagtttcca tgtggtacac                                      30

<210> SEQ ID NO 30
<211> LENGTH: 20
<212> TYPE: DNA
<213> ORGANISM: Homo sapiens

<400> SEQUENCE: 30
gcgtgctaat ggtggaaacc                                                 20

<210> SEQ ID NO 31
<211> LENGTH: 22
<212> TYPE: DNA
<213> ORGANISM: Homo sapiens

<400> SEQUENCE: 31
cggagctctg atgtgttgaa ga                                              22

<210> SEQ ID NO 32
<211> LENGTH: 37
<212> TYPE: DNA
<213> ORGANISM: Homo sapiens

<400> SEQUENCE: 32
acaacgaaat ctatgacaag ttcaagcaga gtacaca                              37

<210> SEQ ID NO 33
<211> LENGTH: 19
<212> TYPE: DNA
<213> ORGANISM: Homo sapiens

<400> SEQUENCE: 33
gacggccttc tgcaattcc                                                  19

<210> SEQ ID NO 34
<211> LENGTH: 26
<212> TYPE: DNA
<213> ORGANISM: Homo sapiens

<400> SEQUENCE: 34
gtataaggtg gtctggttga cttctg                                          26

<210> SEQ ID NO 35
<211> LENGTH: 16
<212> TYPE: DNA
<213> ORGANISM: Homo sapiens

<400> SEQUENCE: 35
agggccaagt tcgtgg                                                         16

<210> SEQ ID NO 36
<211> LENGTH: 24
<212> TYPE: DNA
<213> ORGANISM: Homo sapiens

<400> SEQUENCE: 36
gcgaatctga cttacgccat tatt                                                24

<210> SEQ ID NO 37
<211> LENGTH: 20
<212> TYPE: DNA
<213> ORGANISM: Homo sapiens

<400> SEQUENCE: 37
caagagggcc tccagagtcc                                                     20

<210> SEQ ID NO 38
<211> LENGTH: 27
<212> TYPE: DNA
<213> ORGANISM: Homo sapiens

<400> SEQUENCE: 38
cccacgcaca actcaatggt actgtcg                                             27

<210> SEQ ID NO 39
<211> LENGTH: 17
<212> TYPE: DNA
<213> ORGANISM: Homo sapiens

<400> SEQUENCE: 39
aggagctgct gacccgg                                                        17

<210> SEQ ID NO 40
<211> LENGTH: 21
<212> TYPE: DNA
<213> ORGANISM: Homo sapiens

<400> SEQUENCE: 40
gcttcatctg tcctttccc c                                                    21

<210> SEQ ID NO 41
<211> LENGTH: 13
<212> TYPE: DNA
<213> ORGANISM: Homo sapiens

<400> SEQUENCE: 41
ctgcccagct tct                                                            13

<210> SEQ ID NO 42
<211> LENGTH: 19
<212> TYPE: DNA
<213> ORGANISM: Homo sapiens

<400> SEQUENCE: 42

```
cgtgctcagc tcccttctg                                                    19

<210> SEQ ID NO 43
<211> LENGTH: 21
<212> TYPE: DNA
<213> ORGANISM: Homo sapiens

<400> SEQUENCE: 43
cctggtgtcc tcttggttct g                                                 21

<210> SEQ ID NO 44
<211> LENGTH: 27
<212> TYPE: DNA
<213> ORGANISM: Homo sapiens

<400> SEQUENCE: 44
accaagaccc cagcaccaac catacct                                           27

<210> SEQ ID NO 45
<211> LENGTH: 24
<212> TYPE: DNA
<213> ORGANISM: Homo sapiens

<400> SEQUENCE: 45
ccagaagaac tggtacatca gcaa                                              24

<210> SEQ ID NO 46
<211> LENGTH: 21
<212> TYPE: DNA
<213> ORGANISM: Homo sapiens

<400> SEQUENCE: 46
cgccatactc gaactggaat c                                                 21

<210> SEQ ID NO 47
<211> LENGTH: 17
<212> TYPE: DNA
<213> ORGANISM: Homo sapiens

<400> SEQUENCE: 47
acaagaggca tgtctgg                                                      17

<210> SEQ ID NO 48
<211> LENGTH: 20
<212> TYPE: DNA
<213> ORGANISM: Homo sapiens

<400> SEQUENCE: 48
gcttcgtcaa cctcgtggaa                                                   20

<210> SEQ ID NO 49
<211> LENGTH: 21
<212> TYPE: DNA
<213> ORGANISM: Homo sapiens

<400> SEQUENCE: 49
caaaccggaa ctctcgatgg t                                                 21

<210> SEQ ID NO 50
<211> LENGTH: 29
<212> TYPE: DNA
<213> ORGANISM: Homo sapiens

<400> SEQUENCE: 50
```
atgacaagga attcttccac ccacgctac            29

<210> SEQ ID NO 51
<211> LENGTH: 21
<212> TYPE: DNA
<213> ORGANISM: Homo sapiens

<400> SEQUENCE: 51
cgccatacta cctgggcata g            21

<210> SEQ ID NO 52
<211> LENGTH: 24
<212> TYPE: DNA
<213> ORGANISM: Homo sapiens

<400> SEQUENCE: 52
gatccagagg aggaagtcag aatc            24

<210> SEQ ID NO 53
<211> LENGTH: 32
<212> TYPE: DNA
<213> ORGANISM: Homo sapiens

<400> SEQUENCE: 53
cagatttatg taattgatcc agaaccgtgc cc            32

<210> SEQ ID NO 54
<211> LENGTH: 19
<212> TYPE: DNA
<213> ORGANISM: Homo sapiens

<400> SEQUENCE: 54
tgtgtgacga gcccaagga            19

<210> SEQ ID NO 55
<211> LENGTH: 20
<212> TYPE: DNA
<213> ORGANISM: Homo sapiens

<400> SEQUENCE: 55
tagttgggtc tgggccaaac            20

<210> SEQ ID NO 56
<211> LENGTH: 20
<212> TYPE: DNA
<213> ORGANISM: Homo sapiens

<400> SEQUENCE: 56
cctgccctcg cggcttaccg            20

<210> SEQ ID NO 57
<211> LENGTH: 17
<212> TYPE: DNA
<213> ORGANISM: Homo sapiens

<400> SEQUENCE: 57
ccgacggccg agttgac            17

<210> SEQ ID NO 58
<211> LENGTH: 24
<212> TYPE: DNA
<213> ORGANISM: Homo sapiens

```
<400> SEQUENCE: 58
taacggttag cacacactcc tttg                                              24

<210> SEQ ID NO 59
<211> LENGTH: 32
<212> TYPE: DNA
<213> ORGANISM: Homo sapiens

<400> SEQUENCE: 59
accctcacat caagctacaa cttcaagcag aa                                     32

<210> SEQ ID NO 60
<211> LENGTH: 22
<212> TYPE: DNA
<213> ORGANISM: Homo sapiens

<400> SEQUENCE: 60
gactgctcac gttcatcatg gt                                                22

<210> SEQ ID NO 61
<211> LENGTH: 20
<212> TYPE: DNA
<213> ORGANISM: Homo sapiens

<400> SEQUENCE: 61
aatgtggcgt gtgggatctc                                                   20

<210> SEQ ID NO 62
<211> LENGTH: 24
<212> TYPE: DNA
<213> ORGANISM: Homo sapiens

<400> SEQUENCE: 62
agagctctgt gacgatgacc cgcc                                              24

<210> SEQ ID NO 63
<211> LENGTH: 20
<212> TYPE: DNA
<213> ORGANISM: Homo sapiens

<400> SEQUENCE: 63
gagaagctga gtgccatgca                                                   20

<210> SEQ ID NO 64
<211> LENGTH: 19
<212> TYPE: DNA
<213> ORGANISM: Homo sapiens

<400> SEQUENCE: 64
ggagcccttg tcggatgat                                                    19

<210> SEQ ID NO 65
<211> LENGTH: 22
<212> TYPE: DNA
<213> ORGANISM: Homo sapiens

<400> SEQUENCE: 65
tgccattttc ccagccaggt gg                                                22

<210> SEQ ID NO 66
<211> LENGTH: 21
<212> TYPE: DNA
<213> ORGANISM: Homo sapiens
```

```
<400> SEQUENCE: 66
tggaggcagg catttcagta a                                      21

<210> SEQ ID NO 67
<211> LENGTH: 17
<212> TYPE: DNA
<213> ORGANISM: Homo sapiens

<400> SEQUENCE: 67
ttcccggcaa cccactt                                           17

<210> SEQ ID NO 68
<211> LENGTH: 25
<212> TYPE: DNA
<213> ORGANISM: Homo sapiens

<400> SEQUENCE: 68
cccgagtgtt ccgatccagt ccagt                                  25

<210> SEQ ID NO 69
<211> LENGTH: 20
<212> TYPE: DNA
<213> ORGANISM: Homo sapiens

<400> SEQUENCE: 69
tcacgagcaa ctcgcaaaga                                        20

<210> SEQ ID NO 70
<211> LENGTH: 21
<212> TYPE: DNA
<213> ORGANISM: Homo sapiens

<400> SEQUENCE: 70
tcccatcacc gttagcaact c                                      21

<210> SEQ ID NO 71
<211> LENGTH: 24
<212> TYPE: DNA
<213> ORGANISM: Homo sapiens

<400> SEQUENCE: 71
tgtggcagtc accccaagtt cagc                                   24

<210> SEQ ID NO 72
<211> LENGTH: 22
<212> TYPE: DNA
<213> ORGANISM: Homo sapiens

<400> SEQUENCE: 72
ggattgaact gctttgcctg tt                                     22

<210> SEQ ID NO 73
<211> LENGTH: 20
<212> TYPE: DNA
<213> ORGANISM: Homo sapiens

<400> SEQUENCE: 73
ggcacagcca ccttgtacgt                                        20

<210> SEQ ID NO 74
<211> LENGTH: 22
<212> TYPE: DNA
```

```
<213> ORGANISM: Homo sapiens

<400> SEQUENCE: 74
tttctatttc taggaaggaa tg                                          22

<210> SEQ ID NO 75
<211> LENGTH: 21
<212> TYPE: DNA
<213> ORGANISM: Homo sapiens

<400> SEQUENCE: 75
tgagtgtccc ccggtatctt c                                           21

<210> SEQ ID NO 76
<211> LENGTH: 21
<212> TYPE: DNA
<213> ORGANISM: Homo sapiens

<400> SEQUENCE: 76
cagccgcttt cagattttca t                                           21

<210> SEQ ID NO 77
<211> LENGTH: 27
<212> TYPE: DNA
<213> ORGANISM: Homo sapiens

<400> SEQUENCE: 77
cctgccaatc ccgatgaaat tggaaat                                     27

<210> SEQ ID NO 78
<211> LENGTH: 20
<212> TYPE: DNA
<213> ORGANISM: Homo sapiens

<400> SEQUENCE: 78
gcccgaagcg tttactttga                                             20

<210> SEQ ID NO 79
<211> LENGTH: 24
<212> TYPE: DNA
<213> ORGANISM: Homo sapiens

<400> SEQUENCE: 79
tccattattc ctagctgcgg tatc                                        24

<210> SEQ ID NO 80
<211> LENGTH: 19
<212> TYPE: DNA
<213> ORGANISM: Homo sapiens

<400> SEQUENCE: 80
aaagcaggcc cgagccgcc                                              19
```

NON-INVASIVE METHOD OF DIAGNOSING RENAL FIBROSIS

RELATED APPLICATIONS

This application is a U.S. National Application filed under 35 U.S.C. § 371 from International Application Serial No. PCT/US2013/041206, which was filed May 15, 2013, and published as WO 2013/173493, on Nov. 21, 2013, which claims benefit of the filing date of U.S. Provisional Patent Application No. 61/647,347, filed May 15, 2012, the contents of which are specifically incorporated herein in their entirety.

This invention was made with Government support under Grant Number 2R37-A1051652 awarded by the National Institute of Allergy and Infectious Disease. The United States Government has certain rights in the invention.

BACKGROUND

Renal allograft fibrosis is currently identified using the invasive allograft biopsy procedure in patients with worsening renal function. However, many challenges exist including early diagnosis of fibrosis (see, e.g., Arias et al., Transplantation 91:4 (2011)) and neither serum creatinine nor estimated glomerular filtration rate appears to be an accurate indicator of fibrosis (Yilmaz et al., Transpl Int 20: 608 (2007)). Moreover, the biopsy procedure is costly, complications still occur, sampling errors may bias the diagnosis, and inter-observer variability in grading of biopsies remains a challenge (Huraib et al., Am J Kidney Dis 14:13 (1989); Beckingham et al., Br J Urol 73: 13 (1994); Benfield et al., Transplantation 67: 544 (1999); Sorof et al., Transplantation 60: 1215 (1995); Colvin et al., J Am Soc Nephrol 8: 1930 (1997); Nicholson et al., Kidney Int 58: 390 (2000); Joh et al. Clin Transplant 20 Suppl 15: 53 (2006)).

SUMMARY

A noninvasive test for the diagnosis of renal (kidney) fibrosis is provided herein. Instead of invasive biopsy extraction, urinary samples can be used to assess the propensity for developing renal fibrosis, to assess the severity of renal fibrosis, and/or to monitor the progression of kidney fibrosis in a subject. For example, about 50% of kidney transplants are currently lost due to patient death with a functioning graft. The potent immunosuppressive regimens used to date increase cardiovascular risk factors such as hypertension and hypercholesterolemia and increase malignancy development (9), which may contribute to transplant patient death rates. Over-immunosuppression may also increase the risk for developing opportunistic infections, which may further complicate transplant management. The invention provides a non-invasive method of detecting a transplant related disease that can be performed repeatedly and analyzed quickly without the increased risk of an invasive procedure. Hence, one of the advantages of the methods and devices described herein their non-invasive, which permit repeated risk-free testing.

One aspect of the invention is a method that includes: (a) measuring quantities of vimentin mRNA, NKCC2 mRNA, and E-cadherin mRNA in a test sample of cells obtained from urine; and (b) determining whether the vimentin mRNA quantity is higher, the NKCC2 mRNA quantity is lower, or the E-cadherin mRNA is higher than in healthy urinary cells; and thereby detecting that the sample is a fibrotic kidney sample. Step (a) can also include measuring the quantity of RNA expressed by a housekeeping gene (e.g., 18S rRNA). The quantities of vimentin mRNA, NKCC2 mRNA, and E-cadherin mRNA can be normalized against the quantity of housekeeping gene RNA. Methods for assigning a composite score regarding the expression values are also described herein, which can facilitate identification of fibrotic test samples and subjects that can benefit from treatment.

DESCRIPTION OF THE FIGURES

FIGS. 1A and 1B1-1B22 show steps involved in generating Discovery and Validation sets based upon differential expression of urinary mRNAs and the differential expression of mRNAs in fibrosis and normal renal biopsies. FIG. 1A is a flow chart illustrating the discovery and validation of urinary mRNA profiles. One hundred fourteen renal allograft recipients (48 with biopsies showing fibrosis and 66 with normal biopsy results) were rank ordered within group (Fibrosis group or Normal Biopsy group) by the copy number of 18S rRNA and partitioned into triplets. Within each triplet, the first and third patients were assigned to the Discovery set and the second patient was assigned to the Validation set, resulting in the two sets being exactly matched on fibrosis status and very closely matched on 18S rRNA copy number. Twice as many patients were assigned to the Discovery set in order to enhance statistical power for the exploratory analyses which included a procedure to protect against the risk of a Type I error. FIG. 1B1-1B22 illustrate that urinary cell mRNAs are differentially expressed in fibrosis tissues versus normal tissues by graphically illustrating the $\log_{10}$ normalized mRNA quantities from fibrotic and normal tissues. FIG. 1B1 shows vimentin expression in normal and fibrosis biopsies. FIG. 1B2 shows S100A4 expression in normal and fibrosis biopsies. FIG. 1B3 shows α-SMA expression in normal and fibrosis biopsies. FIG. 1B4 shows fibronectin1 expression in normal and fibrosis biopsies. FIG. 1B5 shows TIMP1 expression in normal and fibrosis biopsies. FIG. 1B6 shows PAI1 expression in normal and fibrosis biopsies. FIG. 1B7 shows collagen 1A1 expression in normal and fibrosis biopsies. FIG. 1B8 shows NKCC2 expression in normal and fibrosis biopsies. FIG. 1B9 shows E-cadherin expression in normal and fibrosis biopsies. FIG. 1B10 shows USAG1 expression in normal and fibrosis biopsies. FIG. 1B11 shows FGF2 expression in normal and fibrosis biopsies. FIG. 1B12 shows TGFβ1 expression in normal and fibrosis biopsies. FIG. 1B13 shows ITGB6 expression in normal and fibrosis biopsies. FIG. 1B14 shows CTGF expression in normal and fibrosis biopsies. FIG. 1B15 shows BMP7 expression in normal and fibrosis biopsies. FIG. 1B16 shows HGF expression in normal and fibrosis biopsies. FIG. 1B17 shows FOX P3 expression in normal and fibrosis biopsies. FIG. 1B18 shows CTLA4 expression in normal and fibrosis biopsies. FIG. 1B19 shows CD103 expression in normal and fibrosis biopsies. FIG. 1B20 shows perforin expression in normal and fibrosis biopsies. FIG. 1B21 shows CD25 expression in normal and fibrosis biopsies. FIG. 1B22 shows granzyme B expression in normal and fibrosis biopsies.

FIGS. 2A1-2A12 and 2B1-2B10 illustrate that the levels of twelve of twenty-two mRNAs analyzed in urinary cell samples appear to be significantly associated with the diagnosis of fibrosis when using the Holm modified Bonferoni procedure (Holm, Journal of Statistics 6: 65 (1979)) to control the risk of a Type I error. FIG. 2A1-2A12 graphically illustrates that the $\log_{10}$ expression values of 12 genes in urinary cells are predictive of fibrosis (A1=vimentin;

A2=HGF; A3=αSMA; A4=fibronectin; A5=perforin; A6=PAI1; A7=TGFβ1; A8=TIMP1; A9=granzyme B; A10=FSP1; A11=CD103; A12=collagen 1A1). The predicted probability of fibrosis as a function of urinary cell mRNA copy number in the Discovery set, for the locally weighted scatterplot smoothing (LOESS) model and the piece-wise linear logistic regression model, after controlling for 18S rRNA copy number. Urine samples were collected from 32 renal transplant recipients with graft dysfunction and biopsy-confirmed fibrosis and 44 recipients with stable allograft function and normal allograft biopsy, and levels of mRNA in urinary cells were measured with the use of pre-amplification enhanced kinetic quantitative PCR assays. FIG. 2B1-2B10 illustrates the predicted probability of fibrosis (Y-axis), controlling for 18S rRNA, of ten genes as a function of individual $\log_{10}$-transformed mRNA copy numbers (X-axis) (B1=BMP7; B2=CTGF; B3=CTLA4; B4=FGF2; B5=CD25; B6=FOXP3; B7=USAG1; B8=E-cadherin; B9=ITGB6; and B10=NKCC2). Each plot shows the LOESS model's predicted probabilities (dotted line), their 95% confidence interval (shaded area) and the logistic regression model's predicted probabilities (solid line). As indicated by the data in FIG. 2B1-2B10, the ten mRNAs tested and evaluated as described are apparently are not significantly correlated with a fibrosis diagnosis. Thus, according to the logistic models, the levels of twelve of the twenty-two mRNAs (vimentin, HGF, α-SMA, fibronectin 1, perforin, PAI1, TGFβ1, TIMP1, granzyme B, FSP1, CD103, and collagen 1A1) were significantly (P-values <0.05 with modified Bonferroni correction) associated with the diagnosis of fibrosis. Adjusted P-value for each parametric model is shown. The number of stable patients, number of fibrosis patients, and percentage of fibrosis patients within categories of the mRNA measure appear in each plot.

FIG. 3A-3D shows the final model derived from the Discovery Set for the diagnosis of fibrosis. FIG. 3A shows the probability of fibrosis in view of log vimentin expression in urinary cells. FIG. 3B shows the probability of fibrosis in view of log NKCC2 expression in urinary cells. FIG. 3C shows the probability of fibrosis in view of log E-cadherin expression in urinary cells. FIG. 3D shows the parameter estimates for the model, including terms accounting for the relationships, including non-linear relationships, between the RNA expression levels and diagnosis.

FIG. 5 graphically illustrates the mean level (and 95% CI) of the 4-gene composite score by fibrosis grade. Kidney allograft biopsies were classified as normal, mild fibrosis (grade I, <25% of cortical area), moderate (grade II, 26-50% of cortical area), or severe (grade III, >50% of cortical area). The mean (and 95% CI) composite scores derived from urinary cell vimentin, NKCC2 and E-cadherin mRNA levels and 18S rRNA level were significantly different across the four groups (P<0.0001, one-way ANOVA). Pair-wise comparisons revealed that the mean composite score of normal biopsies was significantly different from those of mild fibrosis (P=0.0002, Tukey's honestly significant differences criterion), moderate fibrosis (P<0.0001) and severe fibrosis (P<0.0001). Within the fibrosis group however the mean composite scores were not significantly different (mild vs. moderate [P=0.64], mild vs. severe [P=0.65] and moderate vs. severe [P=0.99]). Values under each biopsy diagnosis show the number of kidney graft recipients from whom urine samples were collected for the measurement of urinary cell mRNA.

DETAILED DESCRIPTION

Figure 1A:
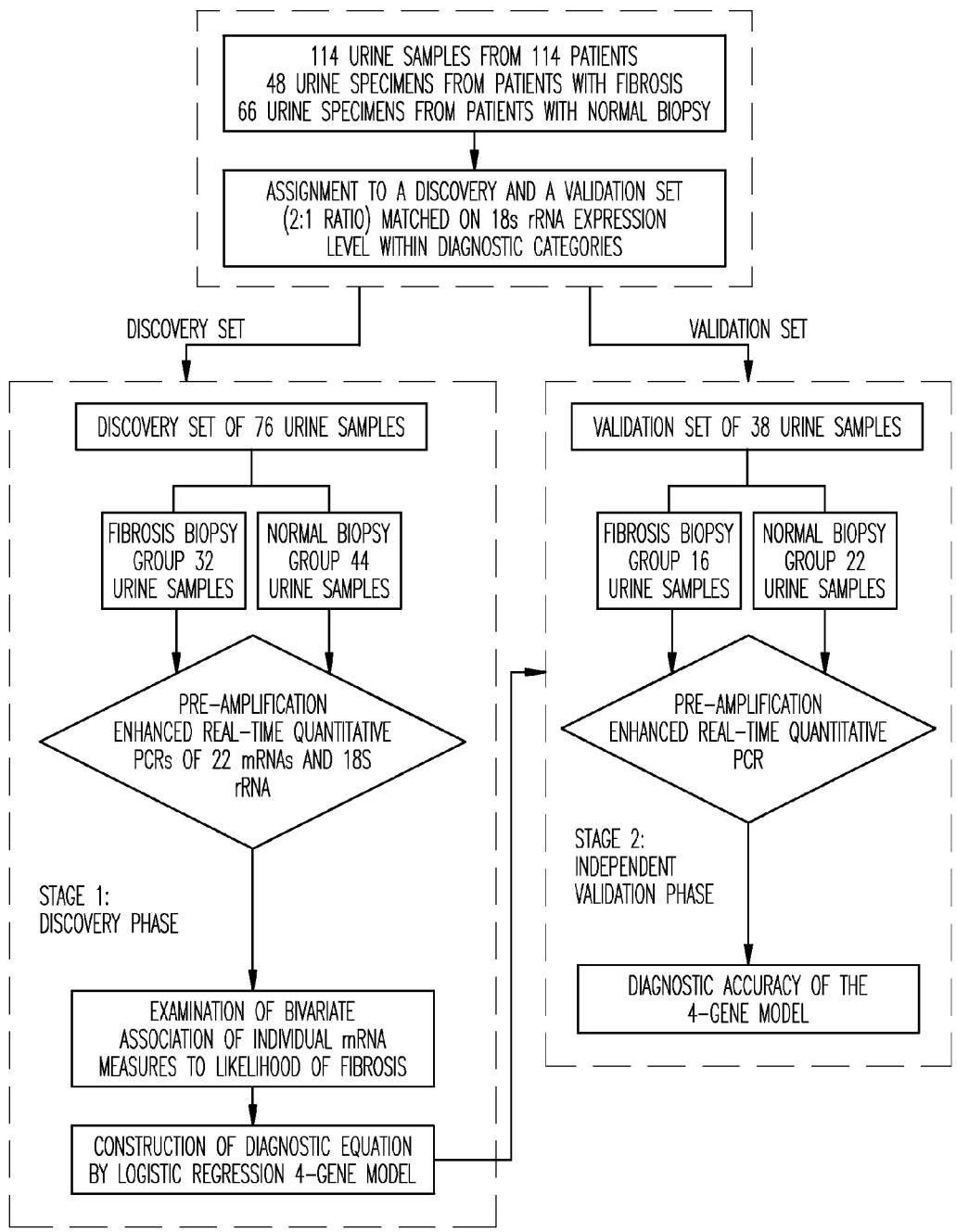

Kidney fibrosis can accurately and less invasively be detected, monitored and evaluated by use of the methods and devices described herein. As demonstrated herein vimentin, NKCC2 and E-cadherin mRNA levels as well as the 18S rRNA level were significantly different in urinary sample cells of subjects with kidney fibrosis than in healthy subjects. Moreover, the severity of kidney fibrosis directly correlates with the degree to which the quantities of these four RNAs in the test sample differ from control RNA quantities. The control RNA quantities are the quantities of the same RNAs from healthy subject(s) who do not have renal fibrosis.

Thus, a four-gene method involving measurement of levels of mRNA for vimentin, NKCC2, and E-cadherin, as well as 18S rRNA, is an accurate, parsimonious, diagnostic model of kidney fibrosis, having 93.8% sensitivity and 84.1% specificity (P<0.0001) in a Discovery set. In an independent validation set, this same model predicted the presence of allograft fibrosis with 77.3% sensitivity and 87.5% specificity (P<0.0001).

Vimentin

Vimentin is a type III intermediate filament protein that is expressed in mesenchymal cells, where it serves as a major cytoskeletal component. Vimentin plays a significant role in supporting and anchoring the position of the organelles in the cytosol.

In the 4-gene diagnostic signature defined herein, vimentin had the strongest association with the allograft fibrosis diagnosis. Ivaska et al. (*Exp Cell Res* 313:2050 (2007)) have reviewed the dynamic nature of vimentin expression and the role of this evolutionarily conserved protein in cell adhesion, migration and signaling. Whereas healthy renal tubular cells do no express vimentin protein, injured ones are decorated by vimentin. Vimentin-expressing regenerating renal tubular cells have been reported by Nakatsuji et al. (*Virchows Arch* 433: 359 (1998); see also, Bielesz et al., *J Clin Invest* 120: 4040 (2010); Hertig et al., *J Am Soc Nephrol* 19: 1584 (2008)).

Nucleic acid and protein sequences for vimentin are available, for example, in the sequence database maintained by the National Center for Biotechnology Information (see website at www.ncbi.nlm.nih.gov/). One example of a human vimentin nucleic acid sequence is available as accession number NM_003380.3 (GI:240849334), provided below as SEQ ID NO:1.

```
  1   GTCCCCGCGC CAGAGACGCA GCCGCGCTCC CACCACCCAC

41   ACCCACCGCG CCCTCGTTCG CCTCTTCTCC GGGAGCCAGT

81   CCGCGCCACC GCCGCCGCCC AGGCCATCGC CACCCTCCGC

121   AGCCATGTCC ACCAGGTCCG TGTCCTCGTC CTCCTACCGC

161   AGGATGTTCG GCGGCCCGGG CACCGCGAGC CGGCCGAGCT

201   CCAGCCGGAG CTACGTGACT ACGTCCACCC GCACCTACAG

241   CCTGGGCAGC GCGCTGCGCC CCAGCACCAG CCGCAGCCTC
```

```
281   TACGCCTCGT CCCCGGGCGG CGTGTATGCC ACGCGCTCCT
321   CTGCCGTGCG CCTGCGGAGC AGCGTGCCCG GGGTGCGGCT
361   CCTGCAGGAC TCGGTGGACT TCTCGCTGGC CGACGCCATC
401   AACACCGAGT TCAAGAACAC CCGCACCAAC GAGAAGGTGG
441   AGCTGCAGGA GCTGAATGAC CGCTTCGCCA ACTACATCGA
481   CAAGGTGCGC TTCCTGGAGC AGCAGAATAA GATCCTGCTG
521   GCCGAGCTCG AGCAGCTCAA GGGCCAAGGC AAGTCGCGCC
561   TGGGGGACCT CTACGAGGAG GAGATGCGGG AGCTGCGCCG
601   GCAGGTGGAC CAGCTAACCA ACGACAAAGC CCGCGTCGAG
641   GTGGAGCGCG ACAACCTGGC CGAGGACATC ATGCGCCTCC
681   GGGAGAAATT GCAGGAGGAG ATGCTTCAGA GAGAGGAAGC
721   CGAAAACACC CTGCAATCTT TCAGACAGGA TGTTGACAAT
761   GCGTCTCTGG CACGTCTTGA CCTTGAACGC AAAGTGGAAT
801   CTTTGCAAGA AGAGATTGCC TTTTTGAAGA AACTCCACGA
841   AGAGGAAATC CAGGAGCTGC AGGCTCAGAT TCAGGAACAG
881   CATGTCCAAA TCGATGTGGA TGTTTCCAAG CCTGACCTCA
921   CGGCTGCCCT GCGTGACGTA CGTCAGCAAT ATGAAAGTGT
961   GGCTGCCAAG AACCTGCAGG AGGCAGAAGA ATGGTACAAA
1001  TCCAAGTTTG CTGACCTCTC TGAGGCTGCC AACCGGAACA
1041  ATGACGCCCT GCGCCAGGCA AAGCAGGAGT CCACTGAGTA
1081  CCGGAGACAG GTGCAGTCCC TCACCTGTGA AGTGGATGCC
1121  CTTAAAGGAA CCAATGAGTC CCTGGAACGC CAGATGCGTG
1161  AAATGGAAGA GAACTTTGCC GTTGAAGCTG CTAACTACCA
1201  AGACACTATT GGCCGCCTGC AGGATGAGAT TCAGAATATG
1241  AAGGAGGAAA TGGCTCGTCA CCTTCGTGAA TACCAAGACC
1281  TGCTCAATGT TAAGATGGCC CTTGACATTG AGATTGCCAC
1321  CTACAGGAAG CTGCTGGAAG GCGAGGAGAG CAGGATTTCT
1361  CTGCCTCTTC CAAACTTTTC CTCCCTGAAC CTGAGGGAAA
1401  CTAATCTGGA TTCACTCCCT CTGGTTGATA CCCACTCAAA
1441  AAGGACACTT CTGATTAAGA CGGTTGAAAC TAGAGATGGA
1481  CAGGTTATCA ACGAAACTTC TCAGCATCAC GATGACCTTG
1521  AATAAAAATT GCACACACTC AGTGCAGCAA TATATTACCA
1561  GCAAGAATAA AAAGAAATC CATATCTTAA AGAAACAGCT
1601  TTCAAGTGCC TTTCTGCAGT TTTTCAGGAG CGCAAGATAG
1641  ATTTGGAATA GGAATAAGCT CTAGTTCTTA ACAACCGACA
1681  CTCCTACAAG ATTTAGAAAA AAGTTTACAA CATAATCTAG
1721  TTTACAGAAA AATCTTGTGC TAGAATACTT TTTAAAAGGT
1781  ATTTTGAATA CCATTAAAAC TGCTTTTTTT TTTCCAGCAA
1801  GTATCCAACC AACTTGGTTC TGCTTCAATA AATCTTTGGA
1841  AAAACTC
```

The human protein encoded by the vimentin nucleic acid shown above as SEQ ID NO:1 has an amino acid sequence with SEQ ID NO:2, shown below.

```
  1  MSTRSVSSSS YRRMFGGPGT ASRPSSSRSY VTTSTRTYSL
 41  GSALRPSTSR SLYASSPGGV YATRSSAVRL RSSVPGVRLL
 81  QDSVDFSLAD AINTEFKNTR TNEKVELQEL NDRFANYIDK
121  VRFLEQQNKI LLAELEQLKG QGKSRLGDLY EEEMRELRRQ
161  VDQLTNDKAR VEVERDNLAE DIMRLREKLQ EEMLQREEAE
201  NTLQSFRQDV DNASLARLDL ERKVESLQEE IAFLKKLHEE
241  EIQELQAQIQ EQHVQIDVDV SKPDLTAALR DVRQQYESVA
281  AKNLQEAEEW YKSKFADLSE AANRNNDALR QAKQESTEYR
321  RQVQSLTCEV DALKGTNESL ERQMREMEEN FAVEAANYQD
361  TIGRLQDEIQ NMKEEMARHL REYQDLLNVK MALDIEIATY
401  RKLLEGEESR ISLPLPNFSS LNLRETNLDS LPLVDTHSKR
411  TLLIKTVETR DGQVINETSQ HHDDLE
```

Another example of a human vimentin nucleic acid sequence is available as accession number NM_003380.3 (GI:240849334), provided below as SEQ ID NO:3.

```
  1  GCCTCTCCAA AGGCTGCAGA AGTTTCTTGC TAACAAAAAG
 41  TCCGCACATT CGAGCAAAGA CAGGCTTTAG CGAGTTATTA
 81  AAAACTTAGG GGCGCTCTTG TCCCCCACAG GGCCCGACCG
121  CACACAGCAA GGCGATGGCC CAGCTGTAAG TTGGTAGCAC
161  TGAGAACTAG CAGCGCGCGC GGAGCCCGCT GAGACTTGAA
201  TCAATCTGGT CTAACGGTTT CCCCTAAACC GCTAGGAGCC
241  CTCAATCGGC GGGACAGCAG GGCGCGTCCT CTGCCACTCT
281  CGCTCCGAGG TCCCCGCGCC AGAGACGCAG CCGCGCTCCC
321  ACCACCCACA CCCACCGCGC CCTCGTTCGC CTCTTCTCCG
361  GGAGCCAGTC CGCGCCACCG CCGCCGCCCA GGCCATCGCC
401  ACCCTCCGCA GCCATGTCCA CCAGGTCCGT GTCCTCGTCC
441  TCCTACCGCA GGATGTTCGG CGGCCCGGGC ACCGCGAGCC
481  GGCCGAGCTC CAGCCGGAGC TACGTGACTA CGTCCACCCG
521  CACCTACAGC CTGGGCAGCG CGCTGCGCCC CAGCACCAGC
561  CGCAGCCTCT ACGCCTCGTC CCCGGGCGGC GTGTATGCCA
601  CGCGCTCCTC TGCCGTGCGC CTGCGGAGCA GCGTGCCCGG
641  GGTGCGGCTC CTGCAGGACT CGGTGGACTT CTCGCTGGCC
681  GACGCCATCA ACACCGAGTT CAAGAACACC CGCACCAACG
721  AGAAGGTGGA GCTGCAGGAG CTGAATGACC GCTTCGCCAA
761  CTACATCGAC AAGGTGCGCT TCCTGGAGCA GCAGAATAAG
801  ATCCTGCTGG CCGAGCTCGA GCAGCTCAAG GGCCAAGGCA
841  AGTCGCGCCT GGGGGACCTC TACGAGGAGG AGATGCGGGA
881  GCTGCGCCGG CAGGTGGACC AGCTAACCAA CGACAAAGCC
```

```
 921    CGCGTCGAGG TGGAGCGCGA CAACCTGGCC GAGGACATCA
 961    TGCGCCTCCG GGAGAAATTG CAGGAGGAGA TGCTTCAGAG
1001    AGAGGAAGCC GAAAACACCC TGCAATCTTT CAGACAGGAT
1041    GTTGACAATG CGTCTCTGGC ACGTCTTGAC CTTGAACGCA
1081    AAGTGGAATC TTTGCAAGAA GAGATTGCCT TTTTGAAGAA
1121    ACTCCACGAA GAGGAAATCC AGGAGCTGCA GGCTCAGATT
1181    CAGGAACAGC ATGTCCAAAT CGATGTGGAT GTTTCCAAGC
1201    CTGACCTCAC GGCTGCCCTG CGTGACGTAC GTCAGCAATA
1241    TGAAAGTGTG GCTGCCAAGA ACCTGCAGGA GGCAGAAGAA
1281    TGGTACAAAT CCAAGTTTGC TGACCTCTCT GAGGCTGCCA
1321    ACCGGAACAA TGACGCCCTG CGCCAGGCAA AGCAGGAGTC
1361    CACTGAGTAC CGGAGACAGG TGCAGTCCCT CACCTGTGAA
1401    GTGGATGCCC TTAAAGGAAC CAATGAGTCC CTGGAACGCC
1441    AGATGCGTGA AATGGAAGAG AACTTTGCCG TTGAAGCTGC
1481    TAACTACCAA GACACTATTG GCCGCCTGCA GGATGAGATT
1521    CAGAATATGA AGGAGGAAAT GGCTCGTCAC CTTCGTGAAT
1561    ACCAAGACCT GCTCAATGTT AAGATGGCCC TTGACATTGA
1601    GATTGCCACC TACAGGAAGC TGCTGGAAGG CGAGGAGAGC
1641    AGGATTTCTC TGCCTCTTCC AAACTTTTCC TCCCTGAACC
1681    TGAGGGAAAC TAATCTGGAT TCACTCCCTC TGGTTGATAC
1721    CCACTCAAAA AGGACACTTC TGATTAAGAC GGTTGAAACT
1761    AGAGATGGAC AGGTTATCAA CGAAACTTCT CAGCATCACG
1801    ATGACCTTGA ATAAAAATTG CACACACTCA GTGCAGCAAT
1841    ATATTACCAG CAAGAATAAA AAGAAATCC ATATCTTAAA
1881    GAAACAGCTT TCAAGTGCCT TTCTGCAGTT TTTCAGGAGC
1921    GCAAGATAGA TTTGGAATAG GAATAAGCTC TAGTTCTTAA
1961    CAACCGACAC TCCTACAAGA TTTAGAAAAA AGTTTACAAC
2001    ATAATCTAGT TTACAGAAAA ATCTTGTGCT AGAATACTTT
2041    TTAAAGGTA TTTTGAATAC CATTAAAACT GCTTTTTTTT
2081    TTCCAGCAAG TATCCAACCA ACTTGGTTCT GCTTCAATAA
2121    ATCTTTGGAA AAACTCAAAA AAAAAAAAA A
```

The human protein encoded by the vimentin nucleic acid shown above as SEQ ID NO:3 has an amino acid sequence with NCBI accession number NP_003371.2 (GI:62414289), shown below as SEQ ID NO:4.

```
  1    MSTRSVSSSS YRRMFGGPGT ASRPSSSRSY VTTSTRTYSL
 41    GSALRPSTSR SLYASSPGGV YATRSSAVRL RSSVPGVRLL
 81    QDSVDFSLAD AINTEFKNTR TNEKVELQEL NDRFANYIDK
121    VRFLEQQNKI LLAELEQLKG QGKSRLGDLY EEEMRELRRQ
161    VDQLTNDKAR VEVERDNLAE DIMRLREKLQ EEMLQREEAE
201    NTLQSFRQDV DNASLARLDL ERKVESLQEE IAFLKKLHEE
241    EIQELQAQIQ EQHVQIDVDV SKPDLTAALR DVRQQYESVA
281    AKNLQEAEEW YKSKFADLSE AANRNNDALR QAKQESTEYR
321    RQVQSLTCEV DALKGTNESL ERQMREMEEN FAVEAANYQD
361    TIGRLQDEIQ NMKEEMARHL REYQDLLNVK MALDIEIATY
401    RKLLEGEESR ISLPLPNFSS LNLRETNLDS LPLVDTHSKR
421    LIKTVETR DGQVINETSQ HHDDLE
```

Urinary cell levels of vimentin mRNA were significantly associated with the presence of kidney fibrosis (P<0.0001, logistic regression model). The predicted probability of fibrosis (Y-axis) as a function of vimentin log 10-transformed mRNA copy numbers (X-axis) is shown in FIG. 2A. The vimentin plot shows the LOESS model's predicted probability (dotted line), its 95% confidence interval (shaded area) and the logistic regression model's predicted probabilities (solid line). The parameter estimates for the 4-gene model including terms accounting for the relationships, including non-linear relationships, between the mRNAs and diagnosis are provided in FIG. 3D.

Any probe or primer that is specific for vimentin can be used in the methods and devices described herein. Examples are provided herein.

NKCC2

The Na—K—Cl cotransporter (NKCC, SLC12A2) is a protein that aids in the active transport of sodium, potassium, and chloride into and out of cells. There are two varieties, or isoforms, of this membrane transport protein, called NKCC1 and NKCC2.

Nucleic acid and protein sequences for NKCC2 are available, for example, in the sequence database maintained by the National Center for Biotechnology Information (see website at www.ncbi.nlm.nih.gov/). One example of a human NKCC2 nucleic acid sequence is available as accession number BC040138.2 (GI:34193025), provided below as SEQ ID NO:5.

```
  1    CTTTGAAGAA CATCCTGAAG ATTATATCGG AGACAATATA
 41    TCAAGAATCT ATTTATTGAA TCATCTAGAA CAAAAGCCAG
 61    GAGCTCCCTA ATGGAAGCAC ATTAGTGTTT ATTTTGATGA
121    AGAAATATAT AGATTTTTTA AAACAACCAC AAAGTAGATA
161    GCTCAGTAAA AAATCAATTT TGGAAGATGT CACTGAACAA
201    CTCTTCCAAT GTATTTCTGG ATTCAGTGCC CAGTAATACC
241    AATCGCTTTC AAGTTAGTGT CATAAATGAG AACCATGAGA
281    GCAGTGCAGC TGCAGATGAC AATACTGACC CACCACATTA
321    TGAAGAAACC TCTTTTGGGG ATGAAGCTCA GAAAAGACTC
361    AGAATCAGCT TTAGGCCTGG GAATCAGGAG TGCTATGACA
401    ATTTCCTCCA AAGTGGAGAA ACTGCTAAAA CAGATGCCAG
441    TTTTCACGCT TATGATTCTC ACACAAACAC ATACTATCTA
481    CAAACTTTTG GCCACAACAC CATGGATGCC GTTCCCAAGA
521    TAGAGTACTA TCGTAACACC GGCAGCATCA GTGGGCCCAA
561    GGTCAACCGA CCCAGCCTGC TTGAGATTCA CGAGCAACTC
601    GCAAAGAATG TGGCAGTCAC CCCAAGTTCA GCTGACAGAG
```

```
 641   TTGCTAACGG TGATGGGATA CCTGGAGATG AACAAGCTGA
 661   AAATAAGGAA GATGATCAAG CTGGTGTTGT GAAGTTTGGA
 721   TGGGTGAAAG GTGTGCTGGT AAGATGCATG CTGAACATCT
 761   GGGGAGTCAT GCTCTTCATT CGCCTCTCCT GGATTGTTGG
 801   AGAAGCTGGA ATTGGTCTTG GAGTTCTCAT AATTCTTCTT
 841   TCCACCATGG TAACTTCTAT TACTGGGTTG TCAACTTCTG
 881   CGATAGCAAC TAACGGGTTT GTTCGTGGAG GTGGGGCCTA
 921   CTATCTTATT TCCAGAAGTT TAGGGCCCGA GTTCGGTGGG
 961   TCAATAGGCC TGATCTTTGC TTTTGCTAAT GCAGTGGCTG
1001   TTGCTATGTA TGTGGTGGGA TTTGCTGAGA CTGTAGTAGA
1041   TCTTCTTAAG GAGAGTGATT CGATGATGGT GGATCCAACC
1081   AATGACATCC GGATTATAGG CTCCATCACA GTGGTGATTC
1121   TTCTAGGAAT TTCAGTAGCT GGAATGGAAT GGGAGGCAAA
1161   GGCCCAAGTC ATTCTTCTGG TCATTCTTCT AATTGCTATT
1201   GCAAACTTCT TCATTGGAAC TGTCATTCCA TCCAACAATG
1241   AGAAAAAGTC CAGAGGTTTC TTTAATTACC AAGCATCAAT
1281   ATTTGCAGAA AACTTTGGGC CACGCTTCAC AAAGGGTGAA
1321   GGCTTCTTCT CTGTCTTTGC CATTTTTTTC CCAGCAGCTA
1361   CTGGGATTCT TGCTGGTGCC AATATCTCAG GAGATTTGGA
1401   GGCACTGAGG AAACAAGGAG CTTCACCTCT CCCTCAAGGA
1441   GCTCAGAGTC GAAGGAGGAG ACAGACTTCC CTTATATGAA
1481   TTAGAACAAG CAAGAGTAGA ATCAAGTGCA AAGGAAAGAG
1521   GAAGCAGAAA TTGCCTGTCC CCTCAAAAAG TAAAGGAAGA
1561   CTTTCAGAAG AGGGGACACT CAATCCAGGT TTTGAGGGAT
1601   GAACAGGAGT TTGCCGACAG GACAAAGAAG AGACGGACAT
1641   TTGAAACAGA AGGAATGGGA TGTAAGAAGG CACCAAGAAA
1681   GATGCTGCTA ATGAGAATTA TTTTATGTGC AGAGTAGTGT
1721   ATGTAATCCT TCATTAATAT ATTAATAAAC ATATTTATAA
1761   ATAAAAAAAA AAAAAAAAAA AAAAAAAAA AAAAA
```

The protein encoded by the NKCC2 nucleic acid with SEQ ID NO:5 has NCBI accession number AAH40138.1 (GI:25304083) and the following human amino acid sequence (SEQ ID NO: 6).

```
  1   MSLNNSSNVF LDSVPSNTNR FQVSVINENH ESSAAADDNT
 41   DPPHYEETSF GDEAQKRLRI SFRPGNQECY DNFLQSGETA
 81   KTDASFHAYD SHTNTYYLQT FGHNTMDAVP KIEYYRNTGS
121   ISGPKVNRPS LLEIHEQLAK NVAVTPSSAD RVANGDGIPG
161   DEQAENKEDD QAGVVKFGWV KGVLVRCMLN IWGVMLFIRL
201   SWIVGEAGIG LGVLIILLST MVTSITGLST SAIATNGFVR
241   GGGAYYLISR SLGPEFGGSI GLIFAFANAV AVAMYVVGFA
281   ETVVDLLKES DSMMVDPTND IRIIGSITVV ILLGISVAGM
321   EWEAKAQVIL LVILLIAIAN FFIGTVIPSN NEKKSRGFFN
361   YQASIFAENF GPRFTKGEGF FSVFAIFFPA ATGILAGANI
401   SGDLEALRKQ GASPLPQGAQ SRRRRQTSLI
```

Even though initial analysis indicated that NKCC2 was not amongst the twelve genes that initially appeared to be more correlated with fibrosis (FIG. 2A), quantification of NKCC2 mRNA levels along with vimentin, E-cadherin and 18S rRNA provided the most accurate, parsimonious, diagnostic model of allograft fibrosis with 93.8% sensitivity and 84.1% specificity ($P<0.0001$).

Additional mRNAs such as HGF ($P<0.0001$), α-SMA ($P<0.0001$), fibronectin 1 ($P<0.0001$), perforin ($P=0.0002$), PAI1 ($P=0.0002$), TGFβ1 ($P=0.0004$), TIMP1 ($P=0.0009$), granzyme B ($P=0.0009$), FSP1 ($P=0.006$), CD103 ($P=0.02$), and collagen 1A1 ($P=0.04$) were also associated with fibrosis. Surprisingly, once vimentin mRNA levels were entered into the four-gene model that included analysis of levels of mRNA for vimentin, NKCC2, and E-cadherin, with 18S rRNA, none of the mRNA levels increased the accuracy of diagnosis of fibrosis. The four gene signature was robustly validated using an independent set of urine samples (the validation set) that were not used in the discovery of the four gene diagnosis model.

The parameter estimates for the four-gene model, including terms accounting for non-linear relationships between the mRNA levels and diagnosis are provided in FIG. 3. As shown, the propensity for development of kidney fibrosis is inversely proportional to NKCC2 expression. In other words, the propensity for development of kidney fibrosis is higher when NKCC2 expression is lower.

Any probe or primer that is specific for NKCC2 can be used in the methods and devices described herein. Examples are provided herein.

E-Cadherin

Cadherins (named for "calcium-dependent adhesion") are a class of type-1 transmembrane proteins. They play important roles in cell adhesion, ensuring that cells within tissues are bound together. They are dependent on calcium (Ca2+) ions to function, hence their name. E-cadherin is found in epithelial tissue.

Nucleic acid and protein sequences for E-cadherin are available, for example, in the sequence database maintained by the National Center for Biotechnology Information (see website at www.ncbi.nlm.nih.gov/). One example of a human E-cadherin nucleic acid sequence is available as accession number XM_007840.5 (GI:15316186), provided below as SEQ ID NO:7.

```
  1   AGTGAATTTT GAAGATTGCA CCGGTCGACA AAGGACAGCC
 41   TATTTTTCCC TCGACACCCG ATTCAAAGTG GGCACAGATG
 81   GTGTGATTAC AGTCAAAAGG CCTCTACGGT TTCATAACCC
121   ACAGATCCAT TTCTTGGTCT ACGCCTGGGA CTCCACCTAC
161   AGAAAGTTTT CCACCAAAGT CACGCTGAAT ACAGTGGGGC
201   ACCACCACCG CCCCCCGCCC CATCAGGCCT CCGTTTCTGG
241   AATCCAAGCA GAATTGCTCA CATTTCCCAA CTCCTCTCCT
281   GGCCTCAGAA GACAGAAGAG AGACTGGGTT ATTCCTCCCA
```

```
321   TCAGCTGCCC AGAAAATGAA AAAGGCCCAT TTCCTAAAAA
361   CCTGGTTCAG ATCAAATCCA ACAAAGACAA AGAAGGCAAG
401   GTTTTCTACA GCATCACTGG CCAAGGAGCT GACACACCCC
441   CTGTTGGTGT CTTTATTATT GAAAGAGAAA CAGGATGGCT
481   GAAGGTGACA GAGCCTCTGG ATAGAGAACG CATTGCCACA
521   TACACTCTCT TCTCTCACGC TGTGTCATCC AACGGGAATG
561   CAGTTGAGGA TCCAATGGAG ATTTTGATCA CGGTAACCGA
601   TCAGAATGAC AACAAGCCCG AATTCACCCA GGAGGTCTTT
641   AAGGGGTCTG TCATGGAAGG TGCTCTTCCA GGAACCTCTG
681   TGATGGAGGT CACAGCCACA GACGCGGACG ATGATGTGAA
721   CACCTACAAT GCCGCCATCG CTTACACCAT CCTCAGCCAA
761   GATCCTGAGC TCCCTGACAA AAATATGTTC ACCATTAACA
801   GGAACACAGG AGTCATCAGT GTGGTCACCA CTGGGCTGGA
841   CCGAGAGAGT TTCCCTACGT ATACCCTGGT GGTTCAAGCT
881   GCTGACCTTC AAGGTGAGGG GTTAAGCACA ACAGCAACAG
921   CTGTGATCAC AGTCACTGAC ACCAACGATA ATCCTCCGAT
961   CTTCAATCCC ACCACGTACA AGGGTCAGGT GCCTGAGAAC
1001  GAGGCTAACG TCGTAATCAC CACACTGAAA GTGACTGATG
1041  CTGATGCCCC CAATACCCCA GCGTGGGAGG CTGTATACAC
1081  CATATTGAAT GATGATGGTG GACAATTTGT CGTCACCACA
1121  AATCCAGTGA ACAACGATGG CATTTTGAAA ACAGCAAAGG
1161  GCTTGGATTT TGAGGCCAAG CAGCAGTACA TTCTACACGT
1201  AGCAGTGACG AATGTGGTAC CTTTTGAGGT CTCTCTCACC
1241  ACCTCCACAG CCACCGTCAC CGTGGATGTG CTGGATGTGA
1281  ATGAAGCCCC CATCTTTGTG CCTCCTGAAA AGAGAGTGGA
1321  AGTGTCCGAG GACTTTGGCG TGGGCCAGGA AATCACATCC
1361  TACACTGCCC AGGAGCCAGA CACATTTATG GAACAGAAAA
1401  TAACATATCG GATTTGGAGA GACACTGCCA ACTGGCTGGA
1441  GATTAATCCG GACACTGGTG CCATTTCCAC TCGGGCTGAG
1481  CTGGACAGGG AGGATTTTGA GCACGTGAAG AACAGCACGT
1521  ACACAGCCCT AATCATAGCT ACAGACAATG GTTCTCCAGT
1561  TGCTACTGGA ACAGGGACAC TTCTGCTGAT CCTGTCTGAT
1601  GTGAATGACA ACGCCCCCAT ACCAGAACCT CGAACTATAT
1641  TCTTCTGTGA GAGGAATCCA AAGCCTCAGG TCATAAACAT
1681  CATTGATGCA GACCTTCCTC CAATACATC TCCCTTCACA
1721  GCAGAACTAA CACACGGGGC GAGTGCCAAC TGGACCATTC
1761  AGTACAACGA CCCAACCCAA GAATCTATCA TTTTGAAGCC
1801  AAAGATGGCC TTAGAGGTGG GTGACTACAA AATCAATCTC
1841  AAGCTCATGG ATAACCAGAA TAAAGACCAA GTGACCACCT
1881  TAGAGGTCAG CGTGTGTGAC TGTGAAGGGG CCGCTGGCGT
1921  CTGTAGGAAG GCACAGCCTG TCGAAGCAGG ATTGCAAATT

1961  CCTGCCATTC TGGGGATTCT TGGAGGAATT CTTGCTTTGC
2001  TAATTCTGAT TCTGCTGCTC TTGCTGTTTC TTCGGAGGAG
2041  AGCGGTGGTC AAAGAGCCCT TACTGCCCCC AGAGGATGAC
2081  ACCCGGGACA ACGTTATTA CTATGATGAA GAAGGAGGCG
2121  GAGAAGAGGA CCAGGACTTT GACTTGAGCC AGCTGCACAG
2161  GGGCCTGGAC GCTCGGCCTG AAGTGACTCG TAACGACGTT
2201  GCACCAACCC TCATGAGTGT CCCCCGGTAT CTTCCCCGCC
2241  CTGCCAATCC CGATGAAATT GGAAATTTTA TTGATGAAAA
2281  TCTGAAAGCG GCTGATACTG ACCCCACAGC CCCGCCTTAT
2321  GATTCTCTGC TCGTGTTTGA CTATGAAGGA AGCGGTTCCG
2361  AAGCTGCTAG TCTGAGCTCC CTGAACTCCT CAGAGTCAGA
2401  CAAAGACCAG GACTATGACT ACTTGAACGA ATGGGGCAAT
2441  CGCTTCAAGA AGCTGGCTGA CATGTACGGA GGCGGCGAGG
2481  ACGACTAGGA GACTCGAGAG AGGCGGGCCC CAGACCCATG
2521  TGCTGGGAAA TGCAGAAATC ACGTTGCTGG TGGTTTT
```

The protein encoded by the E-cadherin nucleic acid with SEQ ID NO:7 has the following human amino acid sequence (SEQ ID NO: 8).

```
1    MEILITVTDQ NDNKPEFTQE VFKGSVMEGA LPGTSVMEVT
41   ATDADDDVNT YNAAIAYTIL SQDPELPDKN MFTINRNTGV
81   ISVVTTGLDR ESFPTYTLVV QAADLQGEGL STTATAVITV
121  TDTNDNPPIF NPTTYKGQVP ENEANVVITT LKVTDADAPN
161  TPAWEAVYTI LNDDGGQFVV TTNPVNNDGI LKTAKGLDFE
201  AKQQYILHVA VTNVVPFEVS LTTSTATVTV DVLDVNEAPI
241  FVPPEKRVEV SEDFGVGQEI TSYTAQEPDT FMEQKITYRI
281  WRDTANWLEI NPDTGAISTR AELDREDFEH VKNSTYTALI
321  IATDNGSPVA TGTGTLLLIL SDVNDNAPIP EPRTIFFCER
361  NPKPQVINII DADLPPNTSP FTAELTHGAS ANWTIQYNDP
401  TQESIILKPK MALEVGDYKI NLKLMDNQNK DQVTTLEVSV
441  CDCEGAAGVC RKAQPVEAGL QIPAILGILG GILALLILIL
481  LLLLFLRRRA VVKEPLLPPE DDTRDNVYYY DEEGGGEEDQ
521  DFDLSQLHRG LDARPEVTRN DVAPTLMSVP RYLPRPANPD
561  EIGNFIDENL KAADTDPTAP PYDSLLVFDY EGSGSEAASL
601  SSLNSSESDK DQDYDYLNEW GNRFKKLADM YGGGEDD
```

Another example of a human E-cadherin nucleic acid sequence is available as accession number NM_004360.3 (GI:169790842), provided below as SEQ ID NO:9.

```
1    AGTGGCGTCG GAACTGCAAA GCACCTGTGA GCTTGCGGAA
41   GTCAGTTCAG ACTCCAGCCC GCTCCAGCCC GGCCCGACCC
81   GACCGCACCC GGCGCCTGCC CTCGCTCGGC GTCCCCGGCC
```

-continued

| | |
|---|---|
| 121 | AGCCATGGGC CCTTGGAGCC GCAGCCTCTC GGCGCTGCTG |
| 161 | CTGCTGCTGC AGGTCTCCTC TTGGCTCTGC CAGGAGCCGG |
| 201 | AGCCCTGCCA CCCTGGCTTT GACGCCGAGA GCTACACGTT |
| 241 | CACGGTGCCC CGGCGCCACC TGGAGAGAGG CCGCGTCCTG |
| 281 | GGCAGAGTGA ATTTTGAAGA TTGCACCGGT CGACAAGGA |
| 321 | CAGCCTATTT TTCCCTCGAC ACCCGATTCA AAGTGGGCAC |
| 361 | AGATGGTGTG ATTACAGTCA AAAGGCCTCT ACGGTTTCAT |
| 401 | AACCCACAGA TCCATTTCTT GGTCTACGCC TGGGACTCCA |
| 441 | CCTACAGAAA GTTTTCCACC AAAGTCACGC TGAATACAGT |
| 481 | GGGGCACCAC CACCGCCCCC CGCCCCATCA GGCCTCCGTT |
| 521 | TCTGGAATCC AAGCAGAATT GCTCACATTT CCCAACTCCT |
| 561 | CTCCTGGCCT CAGAAGACAG AAGAGAGACT GGGTTATTCC |
| 601 | TCCCATCAGC TGCCCAGAAA ATGAAAAAGG CCCATTTCCT |
| 641 | AAAAACCTGG TTCAGATCAA ATCCAACAAA GACAAAGAAG |
| 681 | GCAAGGTTTT CTACAGCATC ACTGGCCAAG GAGCTGACAC |
| 721 | ACCCCCTGTT GGTGTCTTTA TTATTGAAAG AGAAACAGGA |
| 761 | TGGCTGAAGG TGACAGAGCC TCTGGATAGA GAACGCATTG |
| 801 | CCACATACAC TCTCTTCTCT CACGCTGTGT CATCCAACGG |
| 841 | GAATGCAGTT GAGGATCCAA TGGAGATTTT GATCACGGTA |
| 881 | ACCGATCAGA ATGACAACAA GCCCGAATTC ACCCAGGAGG |
| 921 | TCTTTAAGGG TCTGTCATG GAAGGTGCTC TTCCAGGAAC |
| 961 | CTCTGTGATG GAGGTCACAG CCACAGACGC GGACGATGAT |
| 1001 | GTGAACACCT ACAATGCCGC CATCGCTTAC ACCATCCTCA |
| 1041 | GCCAAGATCC TGAGCTCCCT GACAAAAATA TGTTCACCAT |
| 1081 | TAACAGGAAC ACAGGAGTCA TCAGTGTGGT CACCACTGGG |
| 1121 | CTGGACCGAG AGAGTTTCCC TACGTATACC CTGGTGGTTC |
| 1161 | AAGCTGCTGA CCTTCAAGGT GAGGGGTTAA GCACAACAGC |
| 1201 | AACAGCTGTG ATCACAGTCA CTGACACCAA CGATAATCCT |
| 1241 | CCGATCTTCA ATCCCACCAC GTACAAGGGT CAGGTGCCTG |
| 1281 | AGAACGAGGC TAACGTCGTA ATCACCACAC TGAAAGTGAC |
| 1321 | TGATGCTGAT GCCCCCAATA CCCCAGCGTG GGAGGCTGTA |
| 1361 | TACACCATAT TGAATGATGA TGGTGGACAA TTTGTCGTCA |
| 1401 | CCACAAATCC AGTGAACAAC GATGGCATTT TGAAAACAGC |
| 1441 | AAAGGGCTTG GATTTTGAGG CCAAGCAGCA GTACATTCTA |
| 1481 | CACGTAGCAG TGACGAATGT GGTACCTTTT GAGGTCTCTC |
| 1521 | TCACCACCTC CACAGCCACC GTCACCGTGG ATGTGCTGGA |
| 1561 | TGTGAATGAA GCCCCCATCT TTGTGCCTCC TGAAAAGAGA |
| 1601 | GTGGAAGTGT CCGAGGACTT TGGCGTGGGC CAGGAAATCA |
| 1641 | CATCCTACAC TGCCCAGGAG CCAGACACAT TTATGGAACA |
| 1681 | GAAAATAACA TATCGGATTT GGAGAGACAC TGCCAACTGG |
| 1721 | CTGGAGATTA ATCCGGACAC TGGTGCCATT TCCACTCGGG |

-continued

| | |
|---|---|
| 1761 | CTGAGCTGGA CAGGGAGGAT TTTGAGCACG TGAAGAACAG |
| 1801 | CACGTACACA GCCCTAATCA TAGCTACAGA CAATGGTTCT |
| 1841 | CCAGTTGCTA CTGGAACAGG GACACTTCTG CTGATCCTGT |
| 1881 | CTGATGTGAA TGACAACGCC CCCATACCAG AACCTCGAAC |
| 1921 | TATATTCTTC TGTGAGAGGA ATCCAAAGCC TCAGGTCATA |
| 1961 | AACATCATTG ATGCAGACCT TCCTCCCAAT ACATCTCCCT |
| 2001 | TCACAGCAGA ACTAACACAC GGGGCGAGTG CCAACTGGAC |
| 2041 | CATTCAGTAC AACGACCCAA CCCAAGAATC TATCATTTTG |
| 2081 | AAGCCAAAGA TGGCCTTAGA GGTGGGTGAC TACAAAATCA |
| 2121 | ATCTCAAGCT CATGGATAAC CAGAATAAAG ACCAAGTGAC |
| 2161 | CACCTTAGAG GTCAGCGTGT GTGACTGTGA AGGGGCCGCT |
| 2201 | GGCGTCTGTA GGAAGGCACA GCCTGTCGAA GCAGGATTGC |
| 2241 | AAATTCCTGC CATTCTGGGG ATTCTTGGAG GAATTCTTGC |
| 2281 | TTTGCTAATT CTGATTCTGC TGCTCTTGCT GTTTCTTCGG |
| 2321 | AGGAGAGCGG TGGTCAAAGA GCCCTTACTG CCCCCAGAGG |
| 2361 | ATGACACCCG GGACAACGTT TATTACTATG ATGAAGAAGG |
| 2401 | AGGCGGAGAA GAGGACCAGG ACTTTGACTT GAGCCAGCTG |
| 2441 | CACAGGGGCC TGGACGCTCG GCCTGAAGTG ACTCGTAACG |
| 2481 | ACGTTGCACC AACCCTCATG AGTGTCCCCC GGTATCTTCC |
| 2521 | CCGCCCTGCC AATCCCGATG AAATTGGAAA TTTTATTGAT |
| 2561 | GAAAATCTGA AAGCGGCTGA TACTGACCCC ACAGCCCCGC |
| 2601 | CTTATGATTC TCTGCTCGTG TTTGACTATG AAGGAAGCGG |
| 2641 | TTCCGAAGCT GCTAGTCTGA GCTCCCTGAA CTCCTCAGAG |
| 2681 | TCAGACAAAG ACCAGGACTA TGACTACTTG AACGAATGGG |
| 2721 | GCAATCGCTT CAAGAAGCTG GCTGACATGT ACGGAGGCGG |
| 2761 | CGAGGACGAC TAGGGGACTC GAGAGAGGCG GCCCCAGAC |
| 2801 | CCATGTGCTG GGAAATGCAG AAATCACGTT GCTGGTGGTT |
| 2841 | TTTCAGCTCC CTTCCCTTGA GATGAGTTTC TGGGGAAAAA |
| 2881 | AAAGAGACTG GTTAGTGATG CAGTTAGTAT AGCTTTATAC |
| 2921 | TCTCTCCACT TTATAGCTCT AATAAGTTTG TGTTAGAAAA |
| 2961 | GTTTCGACTT ATTTCTTAAA GCTTTTTTTT TTTTCCCATC |
| 3001 | ACTCTTTACA TGGTGGTGAT GTCCAAAAGA TACCCAAATT |
| 3041 | TTAATATTCC AGAAGAACAA CTTTAGCATC AGAAGGTTCA |
| 3081 | CCCAGCACCT TGCAGATTTT CTTAAGGAAT TTTGTCTCAC |
| 3121 | TTTTAAAAAG AAGGGGAGAA GTCAGCTACT CTAGTTCTGT |
| 3161 | TGTTTTGTGT ATATAATTTT TTAAAAAAAA TTTGTGTGCT |
| 3201 | TCTGCTCATT ACTACACTGG TGTGTCCCTC TGCCTTTTTT |
| 3241 | TTTTTTTTAA GACAGGGTCT CATTCTATCG GCCAGGCTGG |
| 3281 | AGTGCAGTGG TGCAATCACA GCTCACTGCA GCCTTGTCCT |
| 3321 | CCCAGGCTCA AGCTATCCTT GCACCTCAGC CTCCCAAGTA |

```
3361  GCTGGGACCA CAGGCATGCA CCACTACGCA TGACTAATTT
3401  TTTAAATATT TGAGACGGGG TCTCCCTGTG TTACCCAGGC
3441  TGGTCTCAAA CTCCTGGGCT CAAGTGATCC TCCCATCTTG
3481  GCCTCCCAGA GTATTGGGAT TACAGACATG AGCCACTGCA
3521  CCTGCCCAGC TCCCCAACTC CCTGCCATTT TTTAAGAGAC
3561  AGTTTCGCTC CATCGCCCAG GCCTGGGATG CAGTGATGTG
3601  ATCATAGCTC ACTGTAACCT CAAACTCTGG GGCTCAAGCA
3641  GTTCTCCCAC CAGCCTCCTT TTTATTTTTT TGTACAGATG
3681  GGGTCTTGCT ATGTTGCCCA AGCTGGTCTT AAACTCCTGG
3721  CCTCAAGCAA TCCTTCTGCC TTGGCCCCCC AAAGAGACTG
3861  GATTGTGGGC ATGAGCTGCT GTGCCCAGCC TCCATGTTTT
3801  AATATCAACT CTCACTCCTG AATTCAGTTG CTTTGCCCAA
3841  GATAGGAGTT CTCTGATGCA GAAATTATTG GGCTCTTTTA
3881  GGGTAAGAAG TTTGTGTCTT TGTCTGGCCA CATCTTGACT
3921  AGGTATTGTC TACTCTGAAG ACCTTTAATG GCTTCCCTCT
3961  TTCATCTCCT GAGTATGTAA CTTGCAATGG GCAGCTATCC
4001  AGTGACTTGT TCTGAGTAAG TGTGTTCATT AATGTTTATT
4041  TAGCTCTGAA GCAAGAGTGA TATACTCCAG GACTTAGAAT
4081  AGTGCCTAAA GTGCTGCAGC CAAAGACAGA GCGGAACTAT
4121  GAAAAGTGGG CTTGGAGATG GCAGGAGAGC TTGTCATTGA
4161  GCCTGGCAAT TTAGCAAACT GATGCTGAGG ATGATTGAGG
4201  TGGGTCTACC TCATCTCTGA AAATTCTGGA AGGAATGGAG
4241  GAGTCTCAAC ATGTGTTTCT GACACAAGAT CCGTGGTTTG
4281  TACTCAAAGC CCAGAATCCC CAAGTGCCTG CTTTTGATGA
4321  TGTCTACAGA AAATGCTGGC TGAGCTGAAC ACATTTGCCC
4361  AATTCCAGGT GTGCACAGAA AACCGAGAAT ATTCAAAATT
4401  CCAAATTTTT TTCTTAGGAG CAAGAAGAAA ATGTGGCCCT
4441  AAAGGGGGTT AGTTGAGGGG TAGGGGGTAG TGAGGATCTT
4481  GATTTGGATC TCTTTTTATT TAAATGTGAA TTTCAACTTT
4521  TGACAATCAA AGAAAAGACT TTTGTTGAAA TAGCTTTACT
4561  GTTTCTCAAG TGTTTTGGAG AAAAAAATCA ACCCTGCAAT
4601  CACTTTTTGG AATTGTCTTG ATTTTTCGGC AGTTCAAGCT
4641  ATATCGAATA TAGTTCTGTG TAGAGAATGT CACTGTAGTT
4681  TTGAGTGTAT ACATGTGTGG GTGCTGATAA TTGTGTATTT
4721  TCTTTGGGGG TGGAAAAGGA AAACAATTCA AGCTGAGAAA
4761  AGTATTCTCA AAGATGCATT TTTATAAATT TTATTAAACA
4801  ATTTTGTTAA ACCAT
```

The protein encoded by the E-cadherin nucleic acid with SEQ ID NO:9 has a human amino acid sequence with NCBI accession number NP_004351.1 (GI:4757960), which is provided below as SEQ ID NO: 10.

```
  1  MGPWSRSLSA LLLLLQVSSW LCQEPEPCHP GFDAESYTFT
 41  VPRRHLERGR VLGRVNFEDC TGRQRTAYFS LDTRFKVGTD
 61  GVITVKRPLR FHNPQIHFLV YAWDSTYRKF STKVTLNTVG
121  HHHRPPPHQA SVSGIQAELL TFPNSSPGLR RQKRDWVIPP
161  ISCPENEKGP FPKNLVQIKS NKDKEGKVFY SITGQGADTP
201  PVGVFIIERE TGWLKVTEPL DRERIATYTL FSHAVSSNGN
241  AVEDPMEILI TVTDQNDNKP EFTQEVFKGS VMEGALPGTS
281  VMEVTATDAD DDVNTYNAAI AYTILSQDPE LPDKNMFTIN
321  RNTGVISVVT TGLDRESFPT YTLVVQAADL QGEGLSTTAT
361  AVITVTDTND NPPIFNPTTY KGQVPENEAN VVITTLKVTD
401  ADAPNTPAWE AVYTILNDDG GQFVVTTNPV NNDGILKTAK
441  GLDFEAKQQY ILHVAVTNVV PFEVSLTTST ATVTVDVLDV
481  NEAPIFVPPE KRVEVSEDFG VGQEITSYTA QEPDTFMEQK
521  ITYRIWRDTA NWLEINPDTG AISTRAELDR EDFEHVKNST
561  YTALIIATDN GSPVATGTGT LLLILSDVND NAPIPEPRTI
601  FFCERNPKPQ VINIIDADLP PNTSPFTAEL THGASANWTI
641  QYNDPTQESI ILKPKMALEV GDYKINLKLM DNQNKDQVTT
681  LEVSVCDCEG AAGVCRKAQP VEAGLQIPAI LGILGGILAL
721  LILILLLLLF LRRRAVVKEP LLPPEDDTRD NVYYYDEEGG
761  GEEDQDFDLS QLHRGLDARP EVTRNDVAPT LMSVPRYLPR
801  PANPDEIGNF IDENLKAADT DPTAPPYDSL LVFDYEGSGS
841  EAASLSSLNS SESDKDQDYD YLNEWGNRFK KLADMYGGGE
881  DD
```

Even though initial analysis indicated that E-cadherin was not amongst the twelve genes that initially appeared to be more correlated with fibrosis (FIG. 2A), quantification of E-cadherin mRNA levels along with vimentin, NKCC2 and 18S rRNA provided the most accurate, parsimonious, diagnostic model of allograft fibrosis with 93.8% sensitivity and 84.1% specificity (P<0.0001).

It is surprising that despite initial correlation of fibrosis with HGF (P<0.0001), α-SMA (P<0.0001), fibronectin 1 (P<0.0001), perforin (P=0.0002), PAI1, (P=0.0002), TGFβ1 (P=0.0004), TIMP1 (P=0.0009), granzyme B (P=0.0009), FSP1 (P=0.006), CD103 (P=0.02), and collagen 1A1 (P=0.04), a four-gene model that included analysis of levels of mRNA for vimentin, NKCC2, E-cadherin and 18S rRNA was more accurate and diagnostic of kidney fibrosis. In the independent validation set, this four-gene model predicted the presence of allograft fibrosis with 77.3% sensitivity and 87.5% specificity (P<0.0001).

The parameter estimates for the four-gene model including terms accounting for the relationships, including non-linear relationships, between the mRNAs and diagnosis are provided in FIG. 3. As shown, the propensity for development of kidney fibrosis is proportional to E-cadherin expression. In other words, the propensity for development of kidney fibrosis is higher when E-cadherin expression increases.

Any probe or primer that is specific for E-cadherin can be used in the methods and devices described herein. Examples are provided herein.

18S rRNA

Expression levels of a housekeeping gene can be measured and used to normalize the quantities of the other mRNAs measured. The 18S ribosomal RNA (abbreviated 18S rRNA) is one convenient gene whose expression can be employed for such normalization. The 18S rRNA is a part of the ribosomal RNA. The S in 18S represents Svedberg units. 18S rRNA is a component of the small eukaryotic ribosomal subunit (40S). 18S rRNA is the structural RNA for the small component of eukaryotic cytoplasmic ribosomes, and thus one of the basic components of all eukaryotic cells.

Nucleic acid sequences for rRNA are available, for example, in the sequence database maintained by the National Center for Biotechnology Information (see website at www.ncbi.nlm.nih.gov/). One example of a human rRNA nucleic acid sequence is available as accession number K03432.1 (GI:337377), provided below as SEQ ID NO:11.

```
   1 CGCTGCTCCT CCCGTCGCCG TCCGGGCCCG TCCGTCCGTC
  41 CGTCCGTCGT CCTCCTCGCT NNNNCGGGGC GCCGGGCCCG
  61 TCCTCACNGG CCCCCGNNNN NGTCCNGGCC CGTCGGGGCC
 121 TCGCCGCGCT CTACCTTACC TACCTGGTTG ATCCTGCCAG
 161 TAGCATATGC TTGTCTCAAA GATTAAGCCA TGCATGTCTA
 201 AGTACGCACG GCCGGTACAG TGAAACTGCG AATGGCTCAT
 241 TAAATCAGTT ATGGTTCCTT TGGTCGCTCG CTCCTCTCCT
 281 ACTTGGATAA CTGTGGTAAT TCTAGAGCTA ATACATGCCG
 301 ACGGGCGCTG ACCCCCTTCG CGGGGGGGAT GCGTGCATTT
 361 ATCAGATCAA AACCAACCCG GTCAGCCCCT CTCCGGCCCC
 401 GGCCGGGGGG CGGGCGCCGG CGGCTTTGGT GACTCTAGAT
 441 AACCTCGGGC CGATCGCACG CCCCCCGTGG CGGCGACGAC
 481 CCATTCGAAC GTCTGCCCTA TCAACTTTCG ATGGTAGTCG
 521 CCGTGCCTAC CATGGTGACC ACGGGTGACG GGGAATCAGG
 561 GTTCGATTCC GGAGAGGGAG CCTGAGAAAC GGCTACCACA
 601 TCCAAGGAAG GCAGCAGGCG CGCAAATTAC CCACTCCCGA
 641 CCCGGGGAGG TAGTGACGAA AAATAACAAT ACAGGACTCT
 681 TTCGAGGCCC TGTAATTGGA ATGAGTCCAC TTTAAATCCT
 721 TTAACGAGGA TCCATTGGAG GGCAAGTCTG GTGCCAGCAG
 761 CCGCGGTAAT TCCAGCTCCA ATAGCGTATA TTAAAGTTGC
 801 TGCAGTTAAA AAGCTCGTAG TTGGATCTTG GGAGCGGGCG
 841 GGCGGTCCGC CGCGAGGCGA GCCACCGCCC GTCCCCGCCC
 881 CTTGCCTCTC GGCGCCCCCT CGATGCTCTT AGCTGAGTGT
 921 CCCGCGGGGC CCGAAGCGTT TACTTTGAAA AAATTAGAGT
 961 GTTCAAAGCA GGCCCGAGCC GCCTGGATAC CGCAGCTAGG
1001 AATAATGGAA TAGGACCGCG GTTCTATTTT GTTGGTTTTC
1041 GGAACTGAGG CCATGATTAA GAGGGACGGC CGGGGGCATT
1081 CGTATTGCGC CGCTAGAGGT GAAATTCCTT GGACCGGCGC
1121 AAGACGGACC AGAGCGAAAG CATTTGCCAA GAATGTTTTC
1161 ATTAATCAAG AACGAAAGTC GGAGGTTCGA AGACGATCAG
1201 ATACCGTCGT AGTTCCGACC ATAAACGATG CCGACCGGCG
1241 ATGCGGCGGC GTTATTCCCA TGACCCGCCG GGCAGCTTCC
1281 GGGAAACCAA AGTCTTTGGG TTCCGGGGGG AGTATGGTTG
1321 CAAAGCTGAA ACTTAAAGGA ATTGACGGAA GGGCACCACC
1361 AGGAGTGGAG CCTGCGGCTT AATTTGACTC AACACGGGAA
1401 ACCTCACCCG GCCCGGACAC GGACAGGATT GACAGATTGA
1441 TAGCTCTTTC TCGATTCCGT GGGTGGTGGT GCATGGCCGT
1481 TCTTAGTTGG TGGAGCGATT TGTCTGGTTA ATTCCGATAA
1521 CGAACGAGAC TCTGGCATGC TAACTAGTTA CGCGACCCCC
1561 GAGCGGTCGG CGTCCCCCAA CTTCTTAGAG GGACAAGTGG
1601 CGTTCAGCCA CCCGAGATTG AGCAATAACA GGTCTGTGAT
1641 GCCCTTAGAT GTCCGGGGCT GCACGCGCGC TACACTGACT
1681 GGCTCAGCGT GTGCCTACCC TACGCCGGCA GGCGCGGGTA
1721 ACCCGTTGAA CCCCATTCGT GATGGGGATC GGGGATTGCA
1761 ATTATTCCCC ATGAACGAGG AATTCCCAGT AAGTGCGGGT
1801 CATAAGCTTG CGTTGATTAA GTCCCTGCCC TTTGTACACA
1841 CCGCCCGTCG CTACTACCGA TTGGATGGTT TAGTGAGGCC
1881 CTCGGATCGG CCCCGCCGGG GTCGGCCCAC GGCCCTGGCG
1921 GAGCGCTGAG AAGACGGTCG AACTTGACTA TCTAGAGGAA
1961 GTAAAGTCA TAACAAGGTT TCCGTAGGTG AACCTGCGGA
2001 AGGATCATTA ACGGAGCCCG GACGGCGGCC CGCGGCGGCG
2041 CCGCGCCGCG CTTCCCTCCG CACACCCACC CCCCACCGC
2081 GACGGCGCGT GCGGGCGGGG CCGTGCCCGT TCGTTCGCTC
2121 GCTCGTTCGT TCGCCGCCCG GCCCGGCCGC GAGAGCCGAG
2161 AACTCGGGAG GGAGACGGGG GAGAGAGAGA GAGAGAGAGA
2201 GAGAGAGAGA GAGAGAGAGA GAAAGAAGGG CGTGT
```

The 18S rRNA expression can be used as a normalizing factor for amount and quality of total RNA isolated from the urinary cells. For example, the quantities of vimentin, NKCC2, and E-cadherin mRNAs can be divided by the quantity of 18S rRNA to remove sample-to-sample variability caused by factors other than those relating to expression levels (e.g., variation in cell numbers in the test sample). Surprisingly, the levels of 18S rRNA also contribute to the accuracy of diagnosis.

Assays for Detecting and Quantifying RNA

Any technique known to one of skill in the art for detecting and measuring RNA expression levels can be used in accordance with the methods described herein. Non-limiting examples of such techniques include reverse transcription, polymerase chain reaction pre-amplification, real-time quantitative polymerase chain reaction, microarray analysis, Northern blotting, nuclease protection assays, RNA fingerprinting, polymerase chain reaction, ligase chain reaction, Qbeta replicase, isothermal amplification method, strand displacement amplification, transcription based amplification systems, quantitative nucleic acid amplification assays (e.g., polymerase chain reaction assays), combined reverse transcription/nucleic acid amplification, nuclease protection (SI nuclease or RNAse protection assays), Serial Analysis Gene Expression (SAGE), next generation sequencing, gene expression microarray, as well as other methods.

Nucleic acids the can hybridize RNAs of vimentin, NKCC2, E-cadherin and one or more housekeeping genes (e.g., 18S rRNA) can be used as probes or primers for quantifying these RNAs. For example, the probes and/or primers can selectively hybridize to a nucleic acid encoding any of the polypeptides with SEQ ID NO:2, 4, 6, 8 and/or 10 sequence. When 18S rRNA levels are quantified the probes and/or primers can selectively hybridize to a nucleic acid that has at least 90% or at least 95% sequence identity or sequence complementarity to any of SEQ ID NO:11. Similarly, probes and/or primers for vimentin, NKCC2, and E-cadherin can have at least 90% or at least 95% sequence identity or sequence complementarity to any of SEQ ID NO:1, 3, 5, 7, and/or 9. Examples of primers and/or probes are provided in Table 2. For example, primers or probes for vimentin can include any of SEQ ID NO:12-14, or a combination thereof. Examples of NKCC2 probes or primers can include any of SEQ ID NO: 69-71, or a combination thereof. Examples of E-cadherin probes or primers can include any of SEQ ID NO: 75-77, or a combination thereof. Examples of 18S rRNA probes or primers can include any of SEQ ID NO: 78-81, or a combination thereof.

A "probe or primer" as used herein refers to one or more nucleic acids that may be used to detect one or more RNA type (e.g. vimentin, NKCC2, E-cadherin and a housekeeping RNA such as 18S rRNA). Detection may be, for example, through amplification as in PCR, RT-PCR, quantitative PCR or through hybridization, or through selective destruction and protection, as in assays based on the selective enzymatic degradation of single or double stranded nucleic acids, or by detecting mRNA. Probes and/or primers can be labeled with one or more fluorescent, radioactive, quenchers, or other detectable moieties (including enzymes). Probes may be any size so long as the probe is sufficiently large to selectively detect the desired gene or be amplified.

Primers can be polynucleotides or oligonucleotides capable of being extended in a primer extension reaction at their 3' end. In order for an oligonucleotide to serve as a primer, it typically is sufficiently complementary in sequence to be capable of forming a double-stranded structure with the template, or target, under the conditions employed. Establishing such conditions typically involves selection of solvent and salt concentration, incubation temperatures, incubation times, assay reagents and stabilization factors known to those in the art. The term primer or primer oligonucleotide refers to an oligonucleotide as defined herein, which is capable of acting as a point of initiation of synthesis when employed under conditions in which synthesis of a primer extension product that is complementary to a nucleic acid strand is induced, as, for example, in a cDNA or DNA replication reaction such as a PCR reaction. Like non-primer oligonucleotides, primer oligonucleotides can be labeled according to any technique known in the art, such as with radioactive atoms, fluorescent labels, enzymatic labels, proteins, haptens, antibodies, sequence tags, mass label or the like. Such labels may be employed by associating them, for example, with the 5' terminus of a primer by a plurality of techniques known in the art. Such labels may also act as capture moieties. A probe or primer may be in solution, as would be typical for multiplex PCR, or a probe or primer may be adhered to a solid surface, as in an array or microarray. Compounds such as peptide nucleic acids (PNAs) can be used instead of nucleic acids to hybridize to the RNAs. In addition, probes may contain rare or unnatural nucleic acids such as inosine.

Such a RNA or DNA (or fragments therefore) may serve as a probe, for example, when it is at least 9, at least 10, at least 11, at least 12, at least 13, at least 14, at least 15, or at least 16 consecutive nucleotides in length. In some embodiments, the probe is about 9, about 10, about 11, about 12, about 13, about 14, about 15, about 16, about 17, about 18, about 19, about 20, about 21 or about 22 consecutive nucleotides in length. In further embodiments, the probe may be at least 20, at least 30, at least 50, or at least 70 consecutive nucleotides in length. The primers and/or probes can be less than about 80, less than about 70, less than about 60, less than about 50, less than about 45, less than about 40, less than about 39, less than about 38, less than about 37, less than about 36, less than about 35, less than about 34, less than about 33, less than about 32, less than about 31, or less than about 30 consecutive nucleotides in length.

During quantification probes and primers can be hybridized to vimentin, NKCC2, E-cadherin and housekeeping (e.g. 18S rRNA) RNAs. Hybridization reactions can be performed under conditions of different "stringency". The stringency of a hybridization reaction includes the difficulty with which any two nucleic acid molecules will hybridize to one another. Under stringent conditions, nucleic acid molecules at least 60%, 65%, 70%, 75% identical (or complementary) to each other remain hybridized to each other, whereas molecules with low percent identity do not remain hybridized. As the hybridization conditions become more stringent, the percent sequence identity or percent sequence complementarity between nucleic acid hybrids increases. Under highly stringent conditions, nucleic acid molecules at least 90%, 92%, 94%, 95%, 96%, 97%, 98%, 99%, or 100% identical (or complementary) to each other remain hybridized to each other, whereas molecules with low percent identity cannot remain hybridized.

A preferred, non-limiting example of stringent hybridization conditions are hybridization in 6× sodium chloride/sodium citrate (SSC) at about 45° C., followed by one or more washes in 0.2×SSC, 0.1% SDS at 50° C. A non-limiting example of highly stringent hybridization conditions is hybridization in 6× sodium chloride/sodium citrate (SSC) at about 45° C., followed by one or more washes in 0.2×SSC, 0.1% SDS at 60° C., or preferably at 65° C.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to hydrogen bond with each other, according to generally accepted base-pairing rules.

The probe can be labeled by any of the many different methods known to those skilled in this art. The labels most commonly employed for these studies are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow. The radioactive label can be detected by any of the currently available counting procedures. Non-limiting examples of isotopes include $^3$H, $^{14}$C, $^{32}$P, $^{35}$S, $^{36}$Ci, $^{51}$Cr, $^{57}$Co, $^{58}$Co, $^{59}$Fe, $^{90}$Y, $^{125}$I, $^{131}$I, and $^{186}$Re.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Any enzymes known to one of skill in the art can be utilized. Examples of such enzymes include, but are not limited to, peroxidase, beta-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

Quantification of RNA levels is typically performed in solution. As described herein such quantification of a plurality of RNAs is informative for identifying whether a sample is diagnostic of fibrosis, determining whether a sample exhibits progression of a fibrotic disease or condition, and, whether a sample is diagnostic of the severity of a fibrotic condition (i.e., are prognosis-informative for a particular patient subset).

Quantitative reverse transcriptase PCR (qRT-PCR) can also be used to determine the expression profiles of RNA genes (see, e.g., U.S. Patent Application Publication No. 2005/0048542A1). The first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MLU-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, commonly employed polymerases include the Taq DNA polymerase, which has a 5'-3' nuclease activity but lacks a 3'-5' proofreading endonuclease activity. TaqMan® PCR typically utilizes the 5'-nuclease activity of Taq or Tth polymerase to hydrolyze a hybridization probe bound to its target amplicon, but any enzyme with similar or equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™. Sequence Detection System™ (Perkin-Elmer-Applied Biosystems, Foster City, Calif., USA), or Lightcycler (Roche Molecular Biochemicals, Mannheim, Germany). In one embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system includes software for running the instrument and for analyzing the data.

In some embodiments, the quantitative RT-PCR assay data are presented as Ct values, also referred to as $\Delta$Ct thresholds. The $\Delta$Ct (cycle threshold) is defined as the number of cycles required for the fluorescent signal to cross a detectable threshold. The $\Delta$Ct is a measure of when the amount of RNA expressed exceeds background levels. Ct threshold levels are inversely proportional to the amount of target nucleic acid in the sample (i.e., the lower the Ct threshold the greater the amount of target nucleic acid in the sample). Fluorescence values are recorded during every cycle and represent the amount of product amplified to that point in the amplification reaction. The point when the fluorescent signal is first recorded as statistically significant is the threshold cycle ($\Delta$Ct).

To minimize errors and the effect of sample-to-sample variation, RT-PCR is often performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and $\beta$-actin.

A more recent variation of the RT-PCR technique is the real time quantitative PCR, which measures PCR product accumulation through a dual-labeled fluorogenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., Genome Research 6:986-994 (1996).

Polynucleotide microarrays generally have probes bound to a solid surface. Microarrays can be used to simultaneously measure whether or not any of several RNAs are expressed. A standard Northern blot assay can be used to ascertain an RNA size, and the relative amounts of RNA in a sample, in accordance with conventional Northern hybridization techniques known to those persons of ordinary skill in the art. In Northern blots, RNA samples are first separated by size via electrophoresis in an agarose gel under denaturing conditions. The RNA is then transferred to a membrane, cross-linked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., a RNA from a different species or genomic DNA fragments that might contain an exon) may be used as probes. The labeled probe can be a labeled cDNA; a full-length, single stranded labeled RNA or DNA, or a labeled fragment of that RNA or DNA sequence.

Nuclease protection assays such as ribonuclease protection assays and S1 nuclease assays can be used to detect and quantify specific RNAs. In nuclease protection assays, an antisense probe (labeled with, e.g., radiolabeled or nonisotopic) hybridizes in solution to an RNA sample. Following hybridization, single-stranded, unhybridized probe and RNA are degraded by nucleases. An acrylamide gel is used to separate the remaining protected fragments. Typically, solution hybridization is more efficient than membrane-based hybridization, and it can accommodate up to 100 μg of sample RNA, compared with the 20-30 μg maximum of blot hybridizations.

A ribonuclease protection assay employs RNA probes. Oligonucleotides and other single-stranded DNA probes can only be used in assays containing S1 nuclease. The single-stranded, antisense probe must typically be completely homologous to target RNA to prevent cleavage of the probe:target hybrid by nuclease.

Serial Analysis Gene Expression (SAGE), which is described in e.g., Velculescu et al., 1995, *Science* 270:484-7; Carulli, et al., 1998, *Journal of Cellular Biochemistry Supplements* 30/31:286-96, can also be used to determine RNA abundances in a cell sample.

Transcript levels can be calculated by a standard curve method, and mRNA copy numbers can be normalized against 18S rRNA copy numbers, by dividing the number of mRNA copies by the number of 18S rRNA copies. For example, the number of mRNA copies in 1 μg of RNA can be divided by the number of 18S rRNA copies in 1 femtogram (fg) of RNA.

As described herein, the distribution of each mRNA, as well as the 18S rRNA, exhibited considerable positive skewness, which can be substantially reduced by use of a log transformation. For example, the number of mRNA copies normalized against rRNA can be converted to the $\log_{10}$ values. These $\log_{10}$ values can be used in the 4-gene model to predict the propensity of a subject to develop kidney fibrosis, to predict the severity of a kidney fibrosis disease, and/or to evaluate the progression of a kidney fibrosis disease.

The process for converting into vimentin, NKCC2 and E-cadherin mRNA quantities and the 18S rRNA quantity into a composite score for the diagnosis of fibrosis involves, dividing the 18S rRNA quantity by $10^5$ (i.e., 100,000). The composite score can be calculated as follows.

Composite Score =

$36.10283 + [-15.84215 * \log_{10}(18s)] + 1.56907 * \log_{10}(18s) * \log_{10}(18s) +$ $5.11698 * \max[0, \log_{10}(\text{Vimentin}) - 5.6] + [$ $-1.44145 * \log_{10}(NKCC2)] + 3.31357 * \min[3.1, \log_{10}(E\text{-cadherin})]$ where, $\max[0, \log_{10}(\text{Vimentin}) - 5.6] =$ 0 whenever $\log_{10}(\text{Vimentin})$ is $\leq 5.6$ and =

$\log_{10}(\text{Vimentin}) - 5.6$ whenever $\log_{10}(\text{Vimentin})$ is $> 5.6$;

$\min[3.1, \log_{10}(E\text{-cadherin})] =$ $\log_{10}(E\text{-cadherin})$ whenever $\log_{10}(E\text{-cadherin}) < 3.1$ and =

3.1 whenever $\log_{10}(E\text{-cadherin}) \geq 3.1$;

and $*$ signifies multiplication

The $\log_{10}$ variables are defined as follows:

$\log_{10}$(18s RNA) is $\log_{10}$ of 18S RNA/100,000 quantity in the test sample;

$\log_{10}$(Vimentin) is $\log_{10}$ of normalized vimentin mRNA quantity in the test sample;

$\log_{10}$(NKCC2)] is $\log_{10}$ of normalized NKCC2 mRNA quantity in the test sample; and $\log_{10}$(E-cadherin) is $\log_{10}$ of normalized E-cadherin mRNA quantity in the test sample.

In calculating the composite score, the vimentin mRNA quantity, the NKCC2 mRNA quantity, and the E-cadherin mRNA quantity can be divided by the 18S RNA quantity multiplied by 100,000 before generating the $\log_{10}$(Vimentin), the $\log_{10}$(NKCC2), and the $\log_{10}$(E-cadherin) values, respectively. This generates normalized values of these mRNA quantities.

Normalized Vimentin *mRNA* quantity $$: \frac{\text{measured vimentin } mRNA \text{ quantity}}{\text{Measured } 18S \text{ } rRNA \text{ quantity}/100,000}$$

Normalized *NKCC2 mRNA* quantity:

$$\frac{\text{measured } NKCC2 \text{ } mRNA \text{ quantity}}{\text{Measured } 18S \text{ } rRNA \text{ quantity}/100,000}$$

Normalized *E*-cadherin *mRNA* quantity:

$$\frac{\text{measured } E\text{-cadherin } mRNA \text{ quantity}}{\text{Measured } 18S \text{ } rRNA \text{ quantity}/100,000}$$

The composite score varies from about 1 to 8, where a normal (healthy) composite score is about 3.5. A test sample with a composite score of 4.7 or more indicates that a subject has fibrosis. For example, a test sample with a composite score from about 4.7 to about 6.5 indicates a subject has mild to moderate fibrosis. A test sample with a composite score from about 6.5 or more indicates a subject has moderate to severe fibrosis.

Therefore, kidney fibrosis can be diagnosed using the methods described herein.

Kidney Fibrosis

Human kidney disease can evolve from various origins including kidney transplantation, glomerular nephritis, nephritis associated with systemic lupus, cancer, physical obstructions, toxins, metabolic disease and immunological diseases, all of which may culminate in kidney fibrosis. Different types of insults can therefore converge on a single genetic program resulting in two hallmarks of fibrosis: the proliferation of fibroblasts and overproduction by them of various protein components of connective tissue. In addition, thickening of the basal membrane in the glomeruli accompanies interstitial fibrosis and culminates in glomerulosclerosis.

The severity of kidney fibrosis disease can be described by the grade of disease. Fibrosis grade I is assigned when less than about 25% of the kidney cortical area is fibrotic (mild fibrosis). Fibrosis grade II is assigned when about 26-50% of the kidney cortical area is fibrotic (moderate fibrosis). Fibrosis grade III is assigned when greater than about 50% of the kidney cortical area is fibrotic (severe fibrosis). Those with substantially no evidence of fibrosis have a normal biopsy and exhibit substantially no fibrosis.

Fibrotic diseases are generally characterized by the excess deposition of a fibrous material within the extracellular matrix, which contributes to abnormal changes in tissue architecture and interferes with normal organ function. Tissues damaged by trauma respond by the initiation of a wound-healing program. Fibrosis, a type of disorder characterized by excessive scarring, occurs when the normal self-limiting process of wound healing response is disturbed, and causes excessive production and deposition of collagen. As a result, normal organ tissue is replaced with scar tissue, which eventually leads to the functional failure of the organ.

Treatment

When kidney fibrosis is detected in a test sample, the subject from which the sample was obtained can be treated. Such treatment can include administration of any therapeutic agent useful for treatment of kidney fibrosis. Such therapeutic agents can include agents that treat the underlying cause(s) of kidney fibrosis, that delay the progression of kidney fibrosis, or ameliorate the symptoms of kidney fibrosis. For example, therapeutic agents that can be employed include anti-inflammatory agents, anti-coagulants, antioxidants, blood pressure medications, angiotensin-converting enzyme inhibitors (ACEIs), angiotensin AT1 receptor blockers, connective tissue growth factor (CTGF) inhibitors, antifibrotic agents (e.g., pirfenidone or tranilast), and the like.

Treatment can also include kidney transplantation.

Kits

The methods described herein may be performed by utilizing pre-packaged diagnostic kits that include devices and reagents for performing any of the methods described herein.

For example, a kit can be made and/or used for detecting kidney fibrotic diseases or disorders in a subject, where the kit includes (i) reagents for conducting a method of the invention and (ii) instructions for its use. The kits may include a device for calculating a composite score. Such a device can be a calculator, computer or minicomputer with software for performing the calculation of composite score.

The kits may be conveniently used, e.g., in clinical settings, to monitor kidney function, to detect kidney dysfunction, and to screen, monitor and diagnose transplant recipients for transplant health or the development of transplant related disease.

A variety of reagents can be included in the kits. For example, the nucleic acids (e.g., primers and/or probes) for quantification RNA levels of vimentin, NKCC2, E-cadherin, and a housekeeping gene (e.g., 18S rRNA) can be provided in separate vials, compartments, or areas of a microarray. The kits can therefore include nucleic acid primers for amplifying and quantifying the RNA levels, as well as enzymes for performing the amplification. Enzymes can also be provided in separate vials, or compartments of a container. Such enzymes can include reverse transcriptases, thermally stable DNA polymerases and the like. The kits can also include nucleotides, stabilizing agents, RNase inhibitors, protease inhibitors, and buffers useful in the method of the invention as well as electrophoretic markers such as a 200 bp ladder. The kit will also include detailed instructions for carrying out the methods of the invention.

Definitions

As used herein, the term "fibrosis" refers to the formation or development of excess fibrous connective tissue in an organ or tissue as a reparative or reactive process, as opposed to a formation of fibrous tissue as a normal constituent of an organ or tissue.

A diagnostic biomarker is described by its sensitivity, specificity and its receiver operating characteristics (ROC) curve. ROC-analysis allows finding the best cut-off value to assign the test result to be 'positive' or 'negative'. For clinical decision-making, it is more important to know the positive (PPV; 'true positives') and negative predictive value (NPV; 'true negatives') than its sensitivity and specificity. This calculation then allows determination of how many 'false positive' and 'false negative' results the test produces. These numbers should be as low as possible, because they represent the patients that are wrongly assigned to have either a 'positive' or a 'negative' test. Besides the given and constant factors that affect sensitivity and the specificity of a diagnostic test, the prevalence of the target disease in the screened population largely influences the PPV, the NPV, the number of 'false positives' and the number of 'false negatives'. Therefore, these values should always be calculated based on the 'true prevalence' of the disease in the screened population rather than from a selected population, which may over- or underestimate the 'true prevalence' and consequently lead to wrongly calculated PPV and NPV (64).

A prognostic biomarker should preferably 'predict' the outcome of a particular condition. Prediction requires the further criterion of showing that changes in the value have consequential changes in the outcome. Many prognostic biomarkers used to date only 'correlate' with an outcome (e.g. C-reactive protein and risk of acute myocardial infarction), fewer 'predict' (e.g. smoking and risk of lung cancer or acute myocardial infarction).

As used herein, "obtaining a test sample" involves removing a sample of tissue or fluid from a patient, receiving a sample of tissue or fluid from a patient, receiving a patient's tissue or fluid sample from a physician, receiving a patient's tissue or fluid sample via mail delivery and/or removing a patient's tissue or fluid sample from a storage apparatus (e.g., a refrigerator or freezer) or a facility. Thus, obtaining a test sample can involve removal or receipt of the test sample directly from the patient, but obtaining a test sample can also include receipt of a test sample indirectly from a medical worker, from a storage apparatus/facility, from a mail delivery service after transportation from a medical facility, and any combination thereof. The test sample can therefore originate in one location, and be transported to another location where it is received and tested. Any of these activities or combinations of activities involves "obtaining a test sample." The test sample can be body fluid or a tissue sample. For example, the test sample can be a urine sample or a kidney biopsy.

As used herein the phrase "determining whether a test dataset of expression levels within a test sample from the patient is significantly within a fibrosis dataset or within a non-fibrosis dataset" can involve actual measurement of test dataset expression levels, i.e., quantifying the expression levels of vimentin, NKCC2, E-cadherin, and/or 18S rRNA in a test sample from the patient and then assessing whether the those test dataset expression levels are significantly (e.g., statistically significantly) within a fibrosis dataset or within a non-fibrosis dataset. In some cases, the phrase "determining whether a test dataset of expression levels within a test sample from the patient is significantly within a fibrosis dataset or within a non-fibrosis dataset" involves obtaining measurements of test dataset expression levels by directing another person or entity to make those measurements, and then assessing whether the those test dataset expression levels are significantly (e.g., statistically significantly) within a fibrosis dataset or within a non-fibrosis dataset. In further embodiments, the phrase "determining whether a test dataset of expression levels within a test sample from the patient is significantly within a fibrosis dataset or within a non-fibrosis dataset" involves obtaining measurements of test dataset expression levels by directing another person or entity to make those measurements, and having that other person or entity assess whether the those test dataset expression levels are significantly (e.g., statistically significantly)

within a fibrosis dataset or within a non-fibrosis dataset. The other (second) person or entity can then report to the person or entity that requested the determination and/or assessment. Thus, the determining step can be performed directly by one person or entity; or alternatively, the determining step can be performed indirectly by a second person or entity who is acting at the request of a first person or entity. The first person or entity can assess whether the test dataset expression levels are significantly (e.g., statistically significantly) within a fibrosis dataset or within a non-fibrosis dataset. Alternatively, the first person or entity can direct the second person or entity to assess whether the test dataset expression levels are significantly (e.g., statistically significantly) within a fibrosis dataset or within a non-fibrosis dataset.

As used herein, the term "acute rejection" (e.g., of a transplant) refers to a rejection of a transplanted organ developing after the first 5-60 post-transplant days. It is generally a manifestation of cell-mediated immune injury. It is believed that both delayed hypersensitivity and cytotoxicity mechanisms are involved. The immune injury is directed against HLA, and possibly other cell-specific antigens expressed by the tubular epithelium and vascular endothelium.

As used herein, the term "chronic rejection" (e.g., of a transplant) represents a consequence of combined immunological injury and non-immunological damage (e.g. from hypertensive nephrosclerosis, or nephrotoxicity of immunosuppressants like cyclosporine A), occurring months or years after transplantation and ultimately leading to fibrosis and sclerosis of the allograft, associated with progressive loss of organ function.

Treatment" refers to both therapeutic treatment, and prophylactic or preventative measures. Those in need of treatment include those already with the disorder as well as those prone to have the disorder, or those in whom the disorder is to be prevented.

"Subject" for purposes of treatment refers to any animal classified as a mammal, including humans, domestic and farm animals, and zoo, sports, or pet animals, such as dogs, horses, cats, cows, etc. Preferably, the subject is human.

The present description is further illustrated by the following examples, which should not be construed as limiting in any way. The contents of all cited references (including literature references, issued patents, published patent applications as cited throughout this application) are hereby expressly incorporated by reference.

Example 1. Renal Allograft Histology and Urine Collection Study Cohort and Renal Allograft Histology The for-cause biopsy group consisted of 48 subjects with graft dysfunction and biopsy-confirmed tubulointerstitial fibrosis (Fibrosis biopsy group, N=48) and the protocol biopsy group included 66 subjects with stable allograft function and normal allograft biopsy (Normal biopsy group, N=66).

The biopsy specimens were fixed in formalin, embedded in paraffin, and stained with hematoxylin and eosin, periodic acid—Schiff, and Masson's trichrome stains. Cryostat or paraffin sections of the for-cause biopsies were examined for C4d deposition with the use of anti-human C4d antibody. In addition to screening for the presence or absence of fibrosis and the grading of fibrosis, the allograft biopsies were also classified using the Banff 07 updated version of Banff 97 diagnostic categories and using the Banff schema 66 allograft biopsies were classified as Normal, and 48 biopsies with fibrosis were classified as IF/TA, no evidence of any specific etiology (N=30), chronic antibody-mediated rejection (N=6), chronic active T-cell mediated rejection (N=6), and the remaining 6 with fibrosis were also classified as having diabetic nephropathy (N=4) or recurrent glomerular disease (N=2).

The allograft fibrosis biopsies were also scored for concurrent inflammation as indicated by cellular infiltration within non-fibrotic areas of cortical interstitium. Among the 48 patients with allograft fibrosis, 32 biopsies from 32 patients showed no inflammation (inflammation score=0) and 16 biopsies from 16 patients displayed both fibrosis and inflammation. Inflammation was graded as 1 when 10-25% of cortical interstitium was involved (N=8 biopsies), 2 when 26-50% of cortical interstitium was involved N=2 biopsies) or 3 when greater than 50% cortical interstitium was involved, N=6 biopsies). All biopsies were classified by a pathologist blinded to the molecular study results.

Urine Collection.

One hundred and four of the 114 urine specimens for the mRNA profiling study were collected within 24 hours of the biopsy procedure, 8 within 7 days and the remaining 2 specimens within 15 days. These time lines refer to the time intervals between the biopsy procedure and urine specimen collection and not to the time interval between the time the urine was collected and when it was centrifuged to obtain the urine pellet prepared for RNA isolation.

Urine was centrifuged at 2,000 g for 30 minutes and the cell pellet was prepared within 4 hours of urine collection. RNAlater (50 μl) was then added to the urine pellet and stored at −80° C. prior to isolation of RNA. RNA was extracted from the pellet using the RNeasy mini kit (Qiagen) and reverse-transcribed to cDNA using TaqMan® Reverse Transcription Reagents (Applied Biosystems).

Example 2. Study Cohorts for the Discovery Set and Validation Set

Urine samples were examined from 114 kidney transplant recipients who had undergone either a diagnostic (for-cause) renal allograft biopsy or a scheduled (protocol) biopsy. The biopsies were examined for the presence or absence of tubulointerstitial fibrosis or inflammation, and classified according to the Banff schema (Solez et al., Am J Transplant 8: 753 (2008)) by a pathologist blinded to the mRNA results.

Prior to data analysis, the 114 urine samples were assigned, at a 2:1 ratio, to a Discovery set of 76 samples (32 samples from 32 recipients with renal allograft biopsies showing fibrosis and 44 samples from 44 recipients with normal biopsy results) and an independent Validation set of 38 samples (16 samples from 16 recipients with biopsies showing fibrosis and 22 samples from 22 recipients with normal biopsy results). FIG. 1A outlines the process employed. Neither the recipients' characteristics nor the transplant or renal allograft related variables differed between those assigned to the Discovery set or the Validation set (Table 1). The risk factors for fibrosis such as acute rejection and deceased donor grafts however were more frequent in the fibrosis biopsy group compared to the normal biopsy group.

TABLE 1

Characteristics of the Renal Allograft Recipients

| Parameter | Discovery Set (N = 76) | | | | Validation Set (N = 38) | | | | $P^a$ |
|---|---|---|---|---|---|---|---|---|---|
| | All Patients (N = 76) | Fibrosis Biopsy Group (N = 32) | Normal Biopsy Group (N = 44) | $P^a$ Fibrosis vs. Normal | All Patients (N = 38) | Fibrosis Biopsy Group (N = 16) | Normal Biopsy Group (N = 22) | $P^a$ Fibrosis vs. Normal | Discovery Set vs. Validation Set |
| Recipient Characteristics | | | | | | | | | |
| Age (mean ± SD, years) | 46 ± 13 | 46 ± 14 | 46 ± 12 | 0.88 | 44 ± 10 | 44 ± 9 | 44 ± 12 | 0.80 | 0.40 |
| Gender (Male/female) | 37/39 | 17/15 | 20/24 | 0.50 | 21/17 | 8/8 | 13/9 | 0.57 | 0.50 |
| Ethnicity (White/Black/Other) | 26/19/31 | 12/7/13 | 14/12/18 | 0.82 | 13/11/14 | 4/9/3 | 9/2/11 | 0.006 | 0.88 |
| Cause of End Stage Renal Disease, N (%) | | | | 0.18 | | | | 0.29 | 0.20 |
| Glomerulonephritis | 18 (24) | 10 (31) | 8 (18) | | 7 (18) | 4 (25) | 3 (14) | | |
| Diabetes | 21 (28) | 9 (28) | 12 (27) | | 6 (16) | 1 (6) | 5 (23) | | |
| Cystic/hereditary/Congenital | 11 (15) | 4 (13) | 7 (16) | | 10 (26) | 4 (25) | 6 (27) | | |
| Secondary Glomerulonephritis | 4 (5) | 1 (3) | 3 (7) | | 4 (11) | 3 (19) | 1 (5) | | |
| Hypertension | 6 (8) | 1 (3) | 5 (11) | | 6 (16) | 3 (19) | 3 (14) | | |
| Interstitial nephritis | 4 (5) | 3 (9) | 1 (2) | | 0 (0) | 0 (0) | 0 (0) | | |
| Miscellaneous Conditions | 2 (3) | 2 (6) | 0 (0) | | 1 (3) | 1 (6) | 0 (0) | | |
| Neoplasm | 0 (0) | 0 (0) | 0 (0) | | 1 (3) | 0 (0) | 1 (5) | | |
| Etiology uncertain | 10 (13) | 2 (6) | 8 (18) | | 3 (8) | 0 (0) | 3 (14) | | |
| Peak pre-transplant HLA class I or II PRA (mean ± SD, %)$^b$ | 17.6 ± 23.7 | 18.8 ± 25.3 | 17.0 ± 23.0 | 0.77 | 26.4 ± 28.3 | 34.8 ± 33.1 | 20.3 ± 23.1 | 0.12 | 0.09 |
| Peak pre-transplant HLA class I or II PRA ≥50%, n (%) | 6 (9) | 2 (9) | 4 (9) | 0.95 | 6 (16) | 4 (25) | 2 (9) | 0.18 | 0.29 |
| Transplant variables | | | | | | | | | |
| Deceased donor, N (%) | 26 (34) | 19 (59) | 7 (16) | <0.0001 | 18 (47) | 12 (75) | 6 (27) | 0.004 | 0.17 |
| Donor age (mean ± SD, years) | 44 ± 11 | 48 ± 11 | 42 ± 10 | 0.03 | 45 ± 14 | 49 ± 13 | 42 ± 14 | 0.12 | 0.65 |
| HLA mismatches (mean ± SD) | 3.5 ± 2.0 | 3.8 ± 2.2 | 3.4 ± 1.8 | 0.41 | 3.3 ± 1.8 | 4.6 ± 1.4 | 2.4 ± 1.5 | <0.0001 | 0.57 |
| Cold ischemia time (deceased donor grafts only, mean ± SD, hours) | 20.8 ± 7.6 | 20.5 ± 8.1 | 21.3 ± 7.1 | 0.83 | 22.2 ± 5.0 | 22.9 ± 5.5 | 20.7 ± 3.6 | 0.39 | 0.51 |
| Delayed graft function$^c$, N (%) | | | | | | | | | |
| Deceased donor grafts | 8/26 (39) | 6/19 (32) | 2/7 (29) | 0.88 | 6/18 (33) | 5/12 (42) | 1/6 (17) | 0.28 | 0.85 |
| History of acute rejection before biopsy, N (%) | 9 (12) | 7 (22) | 2 (5) | 0.02 | 9 (24) | 8 (50) | 1 (5) | 0.001 | 0.10 |
| History of BK virus nephropathy before biopsy, N (%) | 2 (3) | 2 (6) | 0 (0) | 0.09 | 2 (5) | 2 (13) | 0 (0) | 0.09 | 0.47 |
| Graft failure within 12 months after biopsy, N (%) | 13 (17) | 13 (41) | 0 (0) | <0.0001 | 8 (21) | 7 (44) | 1 (5) | 0.003 | 0.61 |
| Renal allograft variables | | | | | | | | | |
| Time of biopsy (mean ± SD, months since transplant) | 25.4 ± 53.1 | 54.4 ± 72.7 | 4.3 ± 4.4 | <0.0001 | 14.1 ± 23.3 | 29.2 ± 29.9 | 3.0 ± 3.8 | 0.0002 | 0.21 |
| Serum creatinine at biopsy (mean ± SD, mg/dL) | 2.1 ± 1.5 | 3.2 ± 1.9 | 1.3 ± 0.4 | <0.0001 | 2.3 ± 1.5 | 3.3 ± 1.8 | 1.5 ± 0.4 | <0.0001 | 0.63 |
| eGFR at biopsy (mean ± SD, mL/min/1.73 m$^2$) | 45.1 ± 20.6 | 26.2 ± 13.2 | 58.5 ± 13.1 | <0.0001 | 42.8 ± 19.5 | 29.1 ± 19.0 | 52.7 ± 12.9 | <0.0001 | 0.56 |
| Urinary protein:creatinine ratio$^d$ at biopsy | 1.4 ± 2.9 | 3.6 ± 4.3 | 0.3 ± 0.3 | <0.0001 | 0.5 ± 0.9 | 1.2 ± 1.4 | 0.2 ± 0.1 | 0.004 | 0.11 |

TABLE 1-continued

Characteristics of the Renal Allograft Recipients

| | Discovery Set (N = 76) | | | Validation Set (N = 38) | | |
|---|---|---|---|---|---|---|
| Allograft fibrosis grade | All patients (n = 76) | Fibrosis biopsy group (n = 32) | Normal biopsy group (n = 44) | All patients (n = 38) | Fibrosis biopsy group (n = 16) | Normal biopsy group (n = 22) |
| No fibrosis, N (%) | 44 (58) | 0 (0) | 44 (100) 0 | 22 (58) | 0 (0) | 22 (100) |
| Grade I (<25% of cortical area), N (%) | 7 (9) | 7 (22) | (0) 0 | 2 (5) | 2 (13) | 0 (0) |
| Grade II (26-50% of cortical area), N (%) | 9 (12) | 9 (28) | (0) 0 (0) | 7 (18) | 7 (44) | 0 (0) |
| Grade III (>50% of cortical area), N (%) | 16 (21) | 16 (50) | | 7 (18) | 7 (44) | 0 (0) |
| Mean ± SD fibrosis grade | 1.0 ± 1.2 | 2.3 ± 0.8 | 0.0 ± 0.0 | 1.0 ± 1.2 | 2.3 ± 0.7 | 0.0 ± 0.0 |
| Banff Classification categories[e] | | | | | | |
| Normal | 39 (51) | 0 (0) | 39 (89) | 19 (50) | 0 (0) | 19 (86) |
| Chronic active antibody-mediated rejection | 4 (5) | 4 (13) | 0 (0) | 2 (5) | 2 (13) | 0 (0) |
| Chronic active T-cell mediated rejection | 3 (4) | 3 (9) | 0 (0) | 3 (8) | 3 (19) | 0 (0) |
| IF/TA, no evidence of any specific etiology | 22 (29) | 22 (69) | 0 (0) | 8 (21) | 8 (50) | 0 (0) |
| Other | 8 (11) | 3 (9)[f] | 5 (11)[g] | 6 (16) | 3 (19)[f] | 3 (19)[g] |

[a]P-values determined by Chi-square or Fisher's exact tests for categorical variables or independent samples T-test for continuous variables.
[b]Panel reactive antibodies (PRA) directed to the HLA class I or II antibodies were identified using the complement dependent cytotoxicity assay, and PRA value was available in 67 of 76 patients in the Discovery set (23 of 32 patients in the fibrosis biopsy group and 44 of 44 patients in the normal biopsy group) and 38 of 38 patients in the Validation set.
[c]Defined by the need for hemodialysis in the first week post-transplantation
[d]Urinary protein:creatinine ratio is the urinary protein concentration (mg/dL) divided by the urinary creatinine concentration (mg/dL) in a random urine specimen.
[e]In addition to screening the allograft biopsies for the presence or absence of tubulointerstitial fibrosis and grading the extent of fibrosis, presence or absence of inflammation, the allograft biopsies were also classified using the Banff 07 updated version of the Banff 97 diagnostic categories (21). All 6 biopsies classified as chronic antibody mediated rejection were positive for C4d deposition; cryostat or paraffin sections of the for-cause biopsies were examined for C4d deposition with the use of anti-human C4d antibody. All other biopsies in the fibrosis group were negative for C4d deposition.
[f]6 biopsies in the Other diagnosis category; 3 in the Discovery set and 3 in the Validation set include diabetic nephropathy (N = 4), and glomerulonephritis recurrence (N = 2).
[g]8 biopsies in the Other diagnosis category; 5 in the Discovery set and 3 in the Validation set includes vascular changes but no interstitial fibrosis.

Example 3. Diagnostic Value of Individual mRNA Levels in the Discovery Set

This study employed the pre-amplification enhanced kinetic quantitative PCR assay for the absolute quantification of mRNAs in the urine of renal allograft recipients reported in (Muthukumar et al., N Engl J Med 353: 2342 (2005)). This method is in frequent use in the inventor's laboratory. This assay enables measurement of a large number of mRNAs using a very small quantity of cDNA.

Urine was centrifuged at 2000 g for 30 min within 4 hr of collection. RNA was extracted from the pellet using the RNeasy mini kit (Qiagen, Valencia, Calif.) and reverse transcribed to complementary DNA using TaqMan Reverse Transcription Reagents (Applied Biosystems). PCR analysis involved a preamplification step, followed by quantification of mRNA with an ABI Prism 7500 Fast detection system (Applied Biosystems). Transcript levels were calculated by a standard curve method (Anglicheau et al., Prov. Natl. Acad. Sci. USA 106: 5330 (2009)). The sequence and location of the gene specific oligonucleotide primers and TaqMan probes designed for quantifying the mRNAs in the PCR assays are listed in Table 2.

TABLE 2

Oligonucleotide primers and probes used in kinetic quantitative polymerase chain reaction assays for the quantification of mRNAs.

| Gene | Accession number | Sequence | Location | SEQ ID NO: |
|---|---|---|---|---|
| Vimentin | NM_003380.2 | Sense: 5' TCAGAGAGAGGAAGCCGAAAAC 3' | 706-727 | 12 |
| | | Antisense: 5' CCAGAGACGCATTGTCAACATC 3' | 770-749 | 13 |
| | | Probe: 5' FAM CCCTGCAATCTTTCGAGAC MGB 3' | 729-746 | 14 |
| HGF | BC063485 | Sense: 5' CAAATGTCAGCCCTGGAGTTC 3' | 526-546 | 15 |
| | | Antisense: 5' CTGTAGGTCTTTACCCCGATAGCT 3' | 604-581 | 16 |
| | | Probe: 5' FAM ATGATACCACACGAACACAGCTTTTTGCC TAMARA 3' | 548-576 | 17 |
| α-SMA | NM_001613 | Sense: 5' TGGGACGACATGGAAAAGATC 3' | 288-308 | 18 |
| | | Antisense: 5' CAGGGTGGGATGCTCTTCAG 3' | 365-346 | 19 |
| | | Probe: 5' FAM CCACTCTTTCTACAATGAGCTTCGTGTTGCC TAMRA 3' | 314-344 | 20 |
| Fibronectin 1 | XM_055254 | Sense: 5' GAAAGTACACCTGTTGTCATTCAACA 3' | 2582-2607 | 21 |
| | | Antisense: 5' ACCTTCACGTCTGTCACTTCCA 3' | 2688-2666 | 22 |
| | | Probe: 5' FAM CCACTGGCACCCCACGCTCA TAMRA 3' | 2613-2632 | 23 |
| PAI1 | NM_000602.1 | Sense: 5' AATCAGACGGCAGCACTGTCT 3' | 716-736 | 24 |
| | | Antisense: 5' GGGCGTGGTGAACTCAGTATAGT 3' | 792-770 | 25 |
| | | Probe: 5' FAM TGTGCCCATGATGGC MGB 3' | 738-752 | 26 |

TABLE 2-continued

Oligonucleotide primers and probes used in
kinetic quantitative polymerase chain reaction
assays for the quantification of mRNAs.

| Gene | Accession number | Sequence | Location | SEQ ID NO: |
|---|---|---|---|---|
| Perforin | M28393 | Sense: 5' GGACCAGTACAGCTTCAGCACTG 3' | 492-514 | 27 |
| | | Antisense: 5' GCCCTCTTGAAGTCAGGGTG 3' | 587-568 | 28 |
| | | Probe: 5' FAM TGCCGCTTCTACAGTTTCCATGTGGTACAC TAMRA 3' | 526-555 | 29 |
| TGFI31 | NM_000660 | Sense: 5' GCGTGCTAATGGTGGAAACC 3' | 1170-1189 | 30 |
| | | Antisense: 5' CGGAGCTCTGATGTGTTGAAGA 3' | 1263-1242 | 31 |
| | | Probe: 5' FAM ACAACGAAATCTATGACAAGTTCAAGCAGAGTACACA TAMRA 3' | 1191-1227 | 32 |
| TIMP1 | NM003254 | Sense: 5' GACGGCCTTCTGCAATTCC 3' | 288-306 | 33 |
| | | Antisense: 5' GTATAAGGTGGTCTGGTTGACTTCTG 3' | 366-341 | 34 |
| | | Probe: 5' FAM AGGGCCAAGTTCGTGG MGB 3' | 319-334 | 35 |
| Granzyme B | J04071 | Sense: 5' GCGAATCTGACTTACGCCATTATT 3' | 534-557 | 36 |
| | | Antisense: 5' CAAGAGGGCCTCCAGAGTCC 3' | 638-619 | 37 |
| | | Probe: 5' FAM CCCACGCACAACTCAATGGTACTGTCG TAMRA 3' | 559-585 | 38 |
| FSP1 | CR450345.1 | Sense: 5' AGGAGCTGCTGACCCGG 3' | 104-120 | 39 |
| | | Antisense: 5' GCTTCATCTGTCCTTTTCCCC 3' | 158-138 | 40 |
| | | Probe: 5' FAM CTGCCCAGCTTCT MGB 3' | 124-136 | 41 |
| CD103 | XM_008508 | Sense: 5' CGTGCTCAGCTCCCTTCTG 3' | 211-229 | 42 |
| | | Antisense: 5' CCTGGTGTCCTCTTGGTTCTG 3' | 297-277 | 43 |
| | | Probe: 5' FAM ACCAAGACCCCAGCACCAACCATACCT TAMRA 3' | 231-257 | 44 |
| Collagen 1A1 | NM_000088.3 | Sense: 5' CCAGAAGAACTGGTACATCAGCAA 3' | 4050-4073 | 45 |
| | | Antisense: 5' CGCCATACTCGAACTGGAATC 3' | 4144-4124 | 46 |
| | | Probe: 5' FAM ACAAGAGGCATGTCTGG MGB 3' | 4085-4101 | 47 |
| BMP7 | NM_001719.1 | Sense: 5' GCTTCGTCAACCTCGTGGAA 3' | 526-545 | 48 |
| | | Antisense: 5' CAAACCGGAACTCTCGATGGT 3' | 597-577 | 49 |
| | | Probe: 5' FAM ATGACAAGGAATTCTTCCACCCACGCTAC TAMRA 3' | 547-575 | 50 |
| CTLA4 | BC074893 | Sense: 5' CGCCATACTACCTGGGCATAG 3' | 441-461 | 51 |
| | | Antisense: 5' GATCCAGAGGAGGAAGTCAGAATC 3' | 529-506 | 52 |
| | | Probe: 5' FAM CAGATTTATGTAATTGATCCAGAACCGTGCCC TAMRA 3' | 473-504 | 53 |
| CTGF | NM_001901 | Sense: 5' TGTGTGACGAGCCCAAGGA 3' | 639-657 | 54 |
| | | Antisense: 5' TAGTTGGGTCTGGGCCAAAC 3' | 725-706 | 55 |
| | | Probe: 5' FAM CCTGCCCTCGCGGCTTACCG TAMRA 3' | 674-693 | 56 |
| FGF2 | NM_002006.3 | Sense: 5' CCGACGGCCGAGTTGAC 3' | 601-617 | 57 |
| | | Antisense: 5' TAACGGTTAGCACACACTCCTTTG 3' | 712-689 | 58 |
| | | Probe: 5' FAM ACCCTCACATCAAGCTACAACTTCAAGCAGAA TAMRA 3' | 637-668 | 59 |
| CD25 | NM_000417 | Sense: 5' GACTGCTCACGTTCATCATGGT 3' | 185-206 | 60 |
| | | Antisense: 5' AATGTGGCGTGTGGGATCTT 3' | 266-247 | 61 |
| | | Probe: 5' FAM AGAGCTCTGTGACGATGACCCGCC TAMRA 3' | 222-245 | 62 |
| FoxP3 | NM_014009 | Sense: 5' GAGAAGCTGAGTGCCATGCA 3' | 939-958 | 63 |
| | | Antisense: 5' GGAGCCCTTGTCGGATGAT 3' | 1025-1007 | 64 |
| | | Probe: 5' FAM TGCCATTTTCCCAGCCAGGTGG TAMRA 3' | 962-983 | 65 |
| USAG1 | NM_015464 | Sense: 5' TGGAGGCAGGCATTTCAGTAA 3' | 364-366 | 66 |
| | | Antisense: 5' TTCCCGGCAACCCACTT 3' | 412-396 | 67 |
| | | Probe: 5' FAM CCCGAGTGTTCCGATCCAGTCCAGT TAMRA 3' | 392-368 | 68 |
| NKCC2 | BC040138.2 | Sense: 5' TCACGAGCAACTCGCAAAGA 3' | 588-607 | 69 |
| | | Antisense: 5' TCCCATCACCGTTAGCAACTC 3' | 658-638 | 70 |
| | | Probe: 5' FAM TGTGGCAGTCACCCCAAGTTCAGC TAMRA 3' | 609-632 | 71 |
| ITGB6 | NM_000888.3 | Sense: 5' GGATTGAACTGCTTTGCCTGTT 3' | 21-42 | 72 |
| | | Antisense: 5' GGCACAGCCACCTTGTACGT 3' | 69-88 | 73 |
| | | Probe: 5' FAM TTTCTATTTCTAGGAAGGAATG MGB 3' | 44-65 | 74 |
| E-cadherin | XM_007840 | Sense: 5' TGAGTGTCCCCCGGTATCTTC 3' | 2469-2489 | 75 |
| | | Antisense: 5' CAGCCGCTTTCAGATTTTCAT 3' | 2549-2529 | 76 |
| | | Probe: 5' FAM CCTGCCAATCCCGATGAAATTGGAAAT TAMRA 3' | 2495-2521 | 77 |
| 18S rRNA | K03432 | Sense: 5' GCCCGAAGCGTTTACTTTGA 3' | 929-948 | 78 |
| | | Antisense: 5' TCCATTATTCCTAGCTGCGGTATC 3' | 1009-986 | 79 |
| | | Probe: 5' FAM AAAGCAGGCCCGAGCCGCC TAMRA 3' | 965-983 | 80 |

Pre-Amplification Enhanced Real-Time Quantitative PCR Assay.

Oligonucleotide primers and fluorogenic probes were designed for the measurement of levels of mRNAs (Table 2). encoding proteins implicated in fibrosis, extracellular matrix accumulation, and/or EMT (TGFβ1, integrin β6 [ITGB6], fibroblast growth factor-2 [FGF2], connective tissue growth factor [CTGF], PAI1, tissue inhibitor of metalloproteinases-1 [TIMP1], fibronectin 1, collagen 1A1, E-cadherin, BMP7 and HGF). Also measured were mRNAs for proteins expressed in renal tubular epithelial cells (NKCC2 found on the apical membrane of the thick ascending limb of loop of Henley, and uterine sensitization associated gene 1 [USAG1] expressed in distal collecting tubules), mesenchymal cells (vimentin, FSP1, α-smooth muscle actin [α-SMA]), and effector and/or regulatory T lymphocytes (perforin, granzyme B, CD25, CD103, FoxP3, CTLA4).

PCR analysis was performed by a two-step process, a preamplification step followed by measurement of mRNA with an ABI Prism 7500 Fast detection system. A pre-amplification protocol that allows quantification of these 22 mRNAs from small amounts of cDNA was developed. The pre-amplification reaction for each sample was set up in a 0.2 ml PCR tube with a final reaction volume of 10 μl containing 3.0 μl cDNA (from reverse transcription of 1 μg total RNA in 100 μl buffer), 1.0 μl 10× buffer, 1.0 μl MgCl2 (25 mM), 0.25 μl 4×dNTP (10 mM each), 0.25 μl Ampli-Taq gold (5 U/μl), 0.15 μl primer mix per gene (50 μM sense and 50 μM antisense primer) and water to final volume of 10 μl. Following vortexing, the PCR was set up using a Veriti thermal cycler (Applied Biosystems) and the 10-cycle PCR reaction profile consisted of an initial hold at 95° C. for 10 min, denaturing at 95° C. for 15 seconds and primer annealing and extension at 60° C. for 1 min. At the end of 10 cycles, 140 μl of TE buffer was added to the PCR reaction and 2.5 μl of diluted PCR amplicons were then used for quantification of mRNA using the real-time quantitative PCR assay.

Transcript levels (copy number/μg total RNA) were calculated by a standard curve method and all analyses of mRNA copy numbers statistically controlled for the copy number of the reference gene 18S ribosomal RNA (rRNA).

The LOESS (locally weighted scatterplot smoothing) method was employed in the discovery phase of the analysis to initially examine the bivariate relationship of each mRNA measure to diagnosis in the Discovery set comprised of 32 renal transplant recipients with biopsy-confirmed fibrosis and 44 recipients with normal allograft biopsy results, controlling for the quadratic relationship of 18S rRNA. Logistic regression analysis was then used to parsimoniously model each relationship as a piece-wise linear model.

Advantage of the LOESS Model.

LOESS (locally weighted scatterplot smoothing) is a powerful tool to elucidate the potentially non-linear relationship between two variables since it has the advantage of fitting segments of data without pre-specifying a specific, usually linear, global function. Importantly, a threshold effect at which the risk for an outcome increases can be ascertained.

Definition of Parsimonious Model.

A parsimonious model is a model that contains the fewest number of predictor variables for a given outcome, without compromising the model's prediction accuracy. In essence, it balances the trade-off between simplicity (simpler is better) and the incremental increase in prediction accuracy that is obtained by including more predictors in a model. The analyses of levels of 22 mRNAs measured in this study showed that the diagnostic accuracy of the 4-gene model (vimentin, 18S, NKCC2 and E-cadherin) is not significantly improved by inclusion of the levels of any or all of the remaining 18 mRNAs that were measured. Thus, the 4-gene model is the parsimonious model in this study.

FIG. 1B shows that up to 22 genes are differentially express in renal fibrosis tissues obtained by biopsy compared to normal renal biopsy tissues.

FIG. 2A illustrates that the levels of twelve of the twenty-two mRNAs measured from urinary cells are significantly associated with the diagnosis of fibrosis after using the Holm modified (Holm, *Scandinavian Journal of Statistics* 6: 65 (1979)) Bonferoni procedure to control the risk of a Type I error. The lack of association between the remaining 10 mRNAs and allograft diagnosis is shown in FIG. 2B.

Receiver-Operating-Characteristic (ROC) Curve Analysis.

Analysis involving ROC curve demonstrated that allograft fibrosis can be predicted accurately using urinary cell levels of mRNA for vimentin (area under the curve [AUC] and 95% confidence intervals=0.90, 0.82-0.97), HGF (0.91, 0.84-0.98), α-SMA (0.88, 0.80-0.95), fibronectin 1 (0.83, 0.73-0.93), perforin (0.83, 0.74-0.93), TGFβ1 (0.82, 0.72-0.92), TIMP1 (0.81, 0.71-0.90), granzyme B (0.82, 0.71-0.92), FSP1 (0.81, 0.71-0.91), PAI1, (0.79, 0.68-0.90), collagen 1A1 (0.77, 0.66-0.88) or CD103 (0.76, 0.65-0.87).

Example 4. Multigene Prediction Model of Fibrosis Diagnosis in the Discovery Set It was determined useful to build a multigene prediction model of fibrosis around vimentin in view of biologic properties of vimentin and data from pre-clinical models that vimentin is over-expressed preceding and/or during fibrosis and the clinical observation that vimentin expression in the 3-month protocol biopsies of renal allografts is associated with fibrosis score at 12 months. Accordingly, a LOESS model was once again estimated and corresponding piecewise linear model for the relationship of each mRNA measure to fibrosis, this time controlling for vimentin mRNA level and the quadratic relationship of 18S rRNA level. These analyses showed that after controlling for vimentin mRNA levels, the levels of other mRNAs (HGF, TGFβ1, fibronectin 1, PAIL FSP1, collagen 1A1, α-SMA, CD103, granzyme B or perforin) that were initially significantly associated with fibrosis were no longer significant (P>0.05), whereas the mRNAs for NKCC2 and E-cadherin became significantly associated with the diagnosis (FIG. 3). Based on these findings, a 4-gene diagnostic model that included vimentin, NKCC2, E-cadherin and 18S rRNA was developed. The parameter estimates for the model, provided in FIG. 3, include terms accounting for the relationships, including non-linear relationships, between the mRNAs and diagnosis.

Figure 4C:
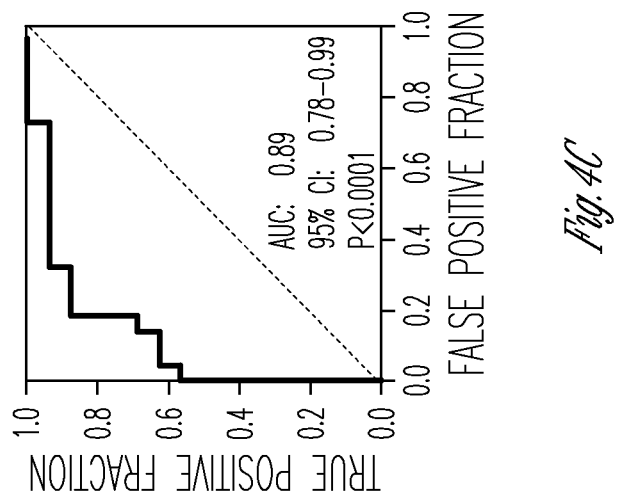
FIG. 4A-4D illustrates the relationship of the composite score to fibrosis in the Discovery set (FIG. 4A), receiver operating characteristics (ROC) curve analysis of the composite score in the Discovery set (FIG. 4B) and the Validation set (FIG. 4C) and the predicted and observed number of transplant recipients with fibrosis for each sextile of the composite score within the Discovery and Validation sets (FIG. 4D).
Figure 4B:
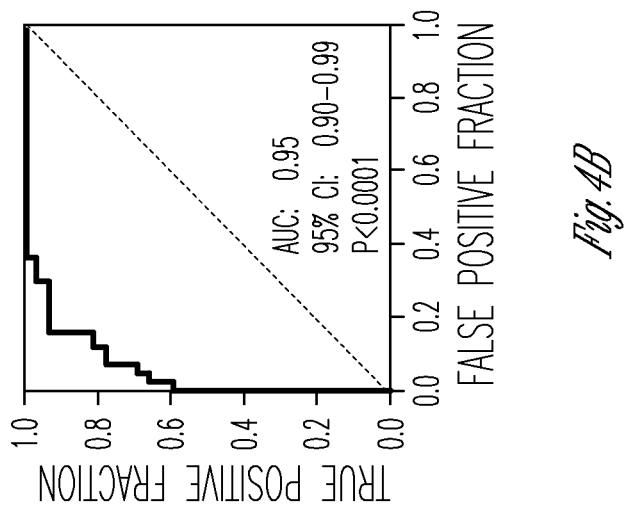
Figure 4A:
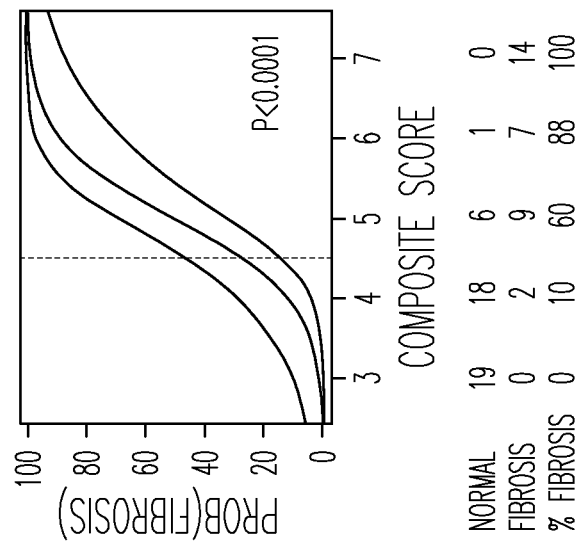

The composite score based on this model was highly associated with the diagnosis of fibrosis (FIG. 4A). The ROC curve (FIG. 4B) shows, for various levels of this composite score, the fraction of true positive results (sensitivity) and false positive results (1-specificity) for distinguishing recipients with allograft fibrosis from recipients with normal biopsy results. The AUC was 0.95 (95% CI: 0.90 to 0.99, P<0.0001), and a significant improvement (P<0.05) over the AUC for vimentin and 18S only. Using the optimal cut-point of 4.5 (the cut-point yielding the highest combined sensitivity and specificity), the composite score predicted fibrosis with a specificity of 84.1% (95% CI: 73.3 to 94.9%) and a sensitivity of 93.8% (95% CI: 85.4.0 to 99.9%) (FIG. 4B).

Example 5. Independent Validation of the Diagnostic Signature

The final diagnostic equation predicting fibrosis in the Discovery set was then validated in an independent Validation set of 38 renal transplant recipients consisting of 16 patients with biopsy-proven fibrosis and 22 recipients with normal allograft biopsy results (Table 1). FIG. 4C shows the ROC curve of this equation based on urinary cell levels of vimentin, NKCC2 and E-cadherin mRNAs and 18S rRNA level for the diagnosis of fibrosis. This 4-gene classifier could diagnose fibrosis in the Validation set with high accuracy and the AUC for the diagnosis of fibrosis in the independent Validation set was 0.89 (95% CI: 0.78 to 0.99, P<0.0001) (FIG. 4C). At the composite score cut-point of 4.5 (the same cut-point used in the Discovery set), fibrosis was diagnosed in the Validation set with a specificity of 77.3% (95% CI: 59.8 to 94.8%) and a sensitivity of 87.5% (95% CI: 71.3 to 99.9%)

Figure 4D:
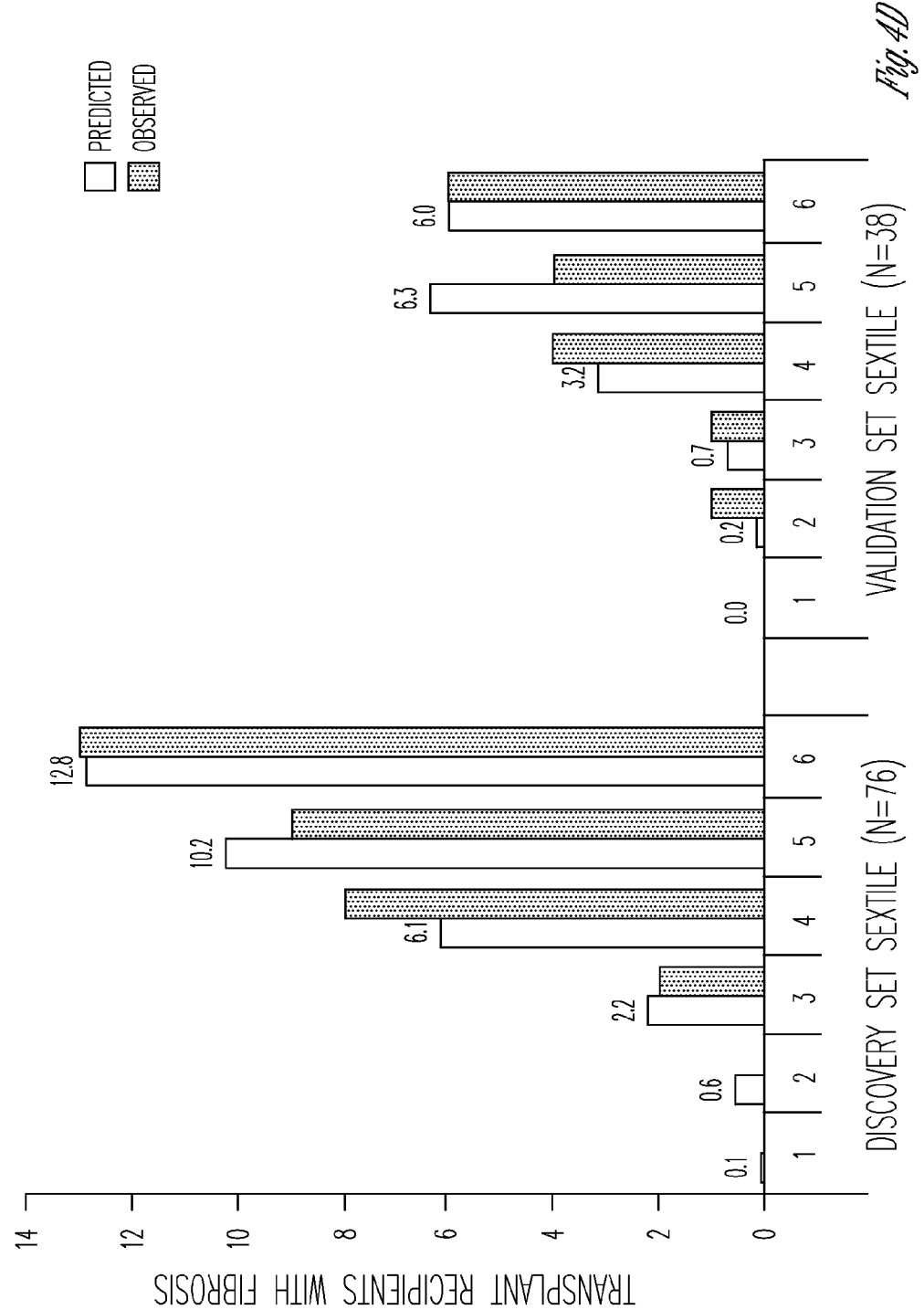

In this study the fit of the predictor model was also examined by dividing the Discovery and Validation sets into sextiles of the composite score and examining the predicted and observed number of transplant recipients with fibrosis, separately for each sets, for each sextile (FIG. 4D). Based on the Hosmer-Lemeshow test, the fit between the observed and the predicted number of subjects with fibrosis in each of the sextiles was excellent (P=0.69) in the Discovery set (left half of FIG. 4D). For the Validation set (right half of FIG. 4D), the P-value was 0.04, suggesting a good fit, given that this set was not involved in the estimation of the model.

Serum creatinine levels were higher in the fibrosis group compared to the normal biopsy group (P<0.0001, Table 1). The study assessed whether the composite score independently differentiates the fibrosis and stable patient groups after controlling for serum creatinine. This analysis showed that the composite score is statistically significant and a slightly stronger predictor of group status (Fibrosis vs. Normal) than serum creatinine (each P<0.0001, controlling for the other).

This study also explored whether graft dysfunction, independent of fibrosis, was associated with the composite score. The log mean composite score of the 4-gene signature was 4.58 (95% CI: 3.52 to 5.64) in the acute tubular necrosis (ATN) group with graft dysfunction (N=9 patients) and 6.49 (95% CI: 5.96 to 7.02) in the fibrosis group with graft dysfunction (N=48 patients) (P=0.01). In addition, the composite score for the ATN group was not significantly different from that of normal biopsy group (N=66) with normal graft function (P=0.12). Whether the time to biopsy was associated with the diagnostic signature (composite score) was also investigated. This analyses showed that there was no significant association between the diagnostic signature and time to biopsy; Pearson correlation coefficient r=0.17, P=0.24 in the fibrosis biopsy group (N=48) and r=0.23, P=0.07 in the normal biopsy group (N=66).

Example 6. Fibrosis Grades and the 4-Gene Composite Score

Figure 5:
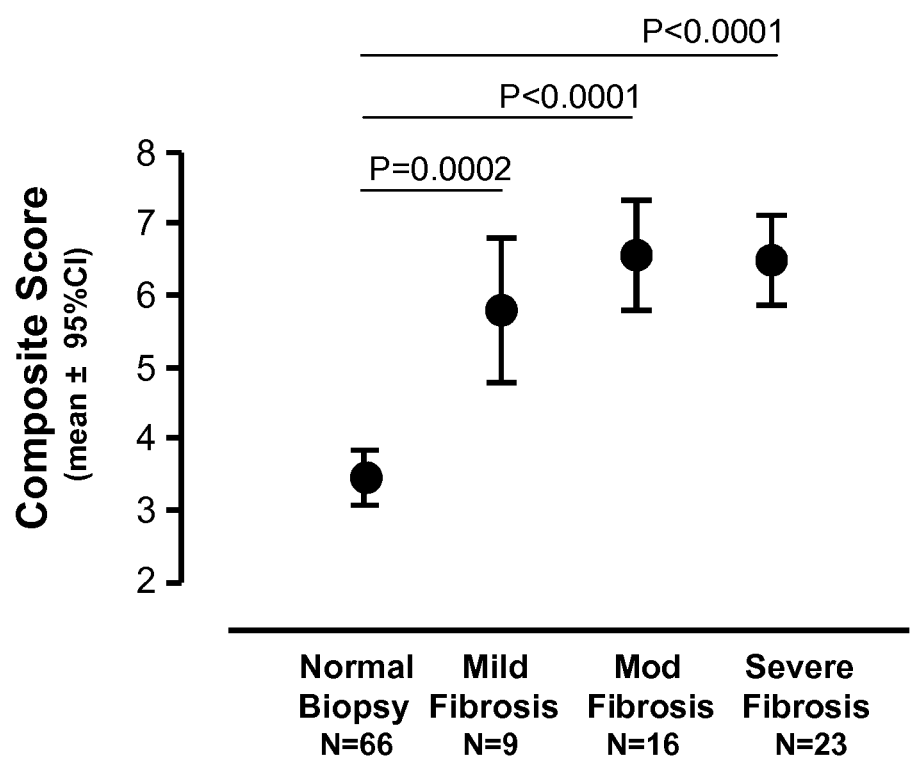

Whether this 4-gene composite score could strongly discriminate patients with differing degrees of fibrosis from patients with no evidence of fibrosis was also investigated. This analysis revealed that the log mean composite score derived from urinary cell vimentin, NKCC2 and E-cadherin mRNA levels and 18S rRNA level was significantly different among the four groups (fibrosis grades I [<25% of cortical area], II [26-50%], and III [>50%] and those with no evidence of fibrosis, P<0.0001, one-way ANOVA) (FIG. 5). Pair-wise comparisons revealed that the mean composite score of normal biopsies were significantly different from that of grade I fibrosis (P=0.0002), grade II fibrosis (P<0.0001) and grade III fibrosis (P<0.0001). The mean composite score however did not differ significantly among the three grades of fibrosis (P=0.58).

Example 7. Allograft Fibrosis with Concurrent Inflammation and the 4-Gene Composite Score Among the 48 patients with allograft fibrosis, 32 biopsies from 32 patients showed no inflammation and 16 biopsies from 16 patients displayed both fibrosis and inflammation. The log mean composite score was 7.5±2.3 in the 16 urine samples from patients with both fibrosis and inflammation and 5.9±1.3 score in the 32 urine samples from patients with fibrosis only and without concurrent inflammation (P=0.003).

Example 8. Statistical Analysis

The 114 patients (48 recipients with allograft fibrosis and 66 recipients with normal biopsies) were rank ordered within group by the copy number of 18S rRNA and partitioned into consecutive triplets. Within each triplet, the first and third patients were assigned to the Discovery set and the second patient was assigned to the Validation set, resulting in the two sets being exactly matched on fibrosis status and very closely matched on 18S. Twice as many patients were assigned to the Discovery set in order to enhance statistical power for the exploratory analyses which included a procedure to protect against the risk of a Type I error.

The distribution of each mRNA, as well as 18S rRNA, exhibited considerable positive skewness, which was substantially reduced by use of a log transformation. LOESS methods were used to examine the relationship of the mRNA measures to diagnosis (Fibrosis vs. Normal). An initial LOESS model revealed a U-shaped relationship of 18S to diagnosis that was well represented by a quadratic function. Then a GAM (generalized additive model) (Hastie & Tibshirani, *Statistical Science* 1: 297 (1986); Hastie & Tibshirani, eds. GENERALIZED ADDITIVE MODELS, New York: Chapman & Hall (1990)) procedure was used to fit an additive LOESS model of the relationship of each individual mRNA measure with diagnosis while statistically controlling for the quadratic effect of 18S. The smoothing parameter for the LOESS model was determined using the generalized cross validation criterion, but restricted to DF<5). After reviewing the smoothed relationship, a piece-wise linear logistic regression spline model was fit that closely approximated the LOESS-smoothed relationship. Plots are presented where the parametric model of the relationship of mRNA level to the probability of being in the Fibrosis group is superimposed on the LOESS model. Also presented are the AUC and its 95% confidence interval for each logistic model. Significance levels of the 22 parametric models were adjusted for the experiment-wise risk of a Type I error using Holm's modified (27) Bonferroni method. Based on the results, one mRNA was chosen to be definitely included in the final model, and then repeated the above process for the remaining 21 mRNA measures to determine which if any could further improve the prediction of fibrosis diagnosis.

This stepwise process was repeated until, after 3 steps, no further mRNA measures significantly improved the prediction model. The ROC curve for the final model and its AUC are presented.

In the Validation phase, the final prediction equation from the Discovery phase was used to calculate composite scores for those in the Validation set. A logistic regression analysis predicting fibrosis diagnosis from this single composite score was estimated to test the significance of the prediction equation. The ROC curve for the prediction equation and its AUC for the Validation set are presented. Finally, the Discovery and Validation sets were each divided into sextiles and an exact test version of the Hosmer-Lemeshow test (Hosmer & Lemeshow, APPLIED LOGISTIC REGRESSION, New York: John Wiley & Sons (1989) was used to assess the fit of the equation in both the Discovery and Validation sets.

All analyses were performed using SAS, version 9.2 (Cary, N.C.).

The process for converting into vimentin, NKCC2 and E-cadherin mRNA quantities and the 18S rRNA quantity into a composite score for the diagnosis of fibrosis involves, dividing the 18S rRNA quantity by $10^5$ (i.e., 100,000). The composite score can be calculated as follows.

$$\text{Composite Score} = $$
$$36.10283 + [-15.84215 * \log_{10}(18s)] + 1.56907 * \log_{10}(18s) * \log_{10}(18s) +$$
$$5.11698 * \max[0, \log_{10}(\text{Vimentin}) - 5.6] + [$$
$$-1.44145 * \log_{10}(NKCC2)] + 3.31357 * \min[3.1, \log_{10}(E\text{-cadherin})]$$

where, $\max[0, \log_{10}(\text{Vimentin}) - 5.6] =$ $\quad 0$ whenever $\log_{10}(\text{Vimentin})$ is $\leq 5.6$ and $=$ $\quad \log_{10}(\text{Vimentin}) - 5.6$ whenever $\log_{10}(\text{Vimentin})$ is $> 5.6$;

$\min[3.1, \log_{10}(E\text{-cadherin})] =$ $\quad \log_{10}(E\text{-cadherin})$ whenever $\log_{10}(E\text{-cadherin}) < 3.1$ and $=$ $\quad 3.1$ whenever $\log_{10}(E\text{-cadherin}) \geq 3.1$;

and $*$ signifies multiplication

The $\log_{10}$ variables are defined as follows:

$\log_{10}(18s \text{ RNA})$ is $\log_{10}$ of 18S RNA/100,000 quantity in the test sample;

$\log_{10}(\text{Vimentin})$ is $\log_{10}$ of normalized vimentin mRNA quantity in the test sample;

$\log_{10}(NKCC2)]$ is $\log_{10}$ of normalized NKCC2 mRNA quantity in the test sample; and $\log_{10}(E\text{-cadherin})$ is $\log_{10}$ of E-cadherin mRNA quantity in the test sample.

In calculating the composite score, the vimentin mRNA quantity, the NKCC2 mRNA quantity, and the E-cadherin mRNA quantity can be divided by the 18S RNA quantity multiplied by 100,000 before generating the $\log_{10}(\text{Vimentin})$, the $\log_{10}(NKCC2)$, and the $\log_{10}(E\text{-cadherin})$ values, respectively. This generates normalized values of these mRNA quantities.

Vimentin mRNA quantity can equal $$\frac{\text{measured vimentin } mRNA \text{ quantity}}{\text{Measured } 18S \text{ } rRNA \text{ quantity/100,000}}$$

NKCC2 mRNA quantity can equal:

$$\frac{\text{measured } NKCC2 \text{ } mRNA \text{ quantity}}{\text{Measured } 18S \text{ } rRNA \text{ quantity/100,000}}$$

E-cadherin mRNA quantity can equal:

$$\frac{\text{measured } E\text{-cadherin } mRNA \text{ quantity}}{\text{Measured } 18S \text{ } rRNA \text{ quantity/100,000}}$$

The composite score varies from about 1 to 8, where a normal (healthy) composite score is about 3.5. A test sample with a composite score of above 4.7 indicates that the subject has fibrosis. For example, a test score from about 4.7 to about 6.5 indicates a subject has mild to moderate fibrosis. A test sample with a composite score from about 6.5 or more indicates a subject has moderate to severe fibrosis.

Therefore, kidney fibrosis can be diagnosed using the methods described herein.

REFERENCES

1. Arias M, Serón D, Moreso F, Bestard O, Praga M. Renal allograft damage: existing challenges. *Transplantation* 2011; 91: 4.
2. Yilmaz S, Isik I, Afrouzian M, et al. Evaluating the accuracy of functional biomarkers for detecting histological changes in chronic allograft nephropathy. *Transpl Int* 2007; 20: 608.
3. Huraib S, Goldberg H, Katz A, et al. Percutaneous needle biopsy of the transplanted kidney: technique and complications. *Am J Kidney Dis* 1989; 14: 13.
4. Beckingham I J, Nicholson M L, Bell P R. Analysis of factors associated with complications following renal transplant needle core biopsy. *Br J Urol* 1994; 73: 13.
5. Benfield M R, Herrin J, Feld L, Rose S, Stablein D, Tejani A. Safety of kidney biopsy in pediatric transplantation: a report of the Controlled Clinical Trials in Pediatric Transplantation Trial of Induction Therapy Study Group. *Transplantation* 1999; 67: 544.
6. Sorof J M, Vartanian R K, Olson J L, Tomlanovich S J, Vincenti F G, Amend W J C. Histopathological concordance of paired renal allograft biopsy cores: effect on the diagnosis and management of acute rejection. *Transplantation* 1995; 60: 1215.
7. Colvin R B, Cohen A H, Saiontz C, et al. Evaluation of pathologic criteria for acute renal allograft rejection: reproducibility, sensitivity, and clinical correlation. *J Am Soc Nephrol* 1997; 8: 1930.
8. Nicholson M L, Wheatley T J, Doughman T M, et al. A prospective randomized trial of three different sizes of core-cutting needle for renal transplant biopsy. *Kidney Int* 2000; 58: 390.
9. Joh K, Morozumi K, Kitamura H. Symposium: evaluating the reproducibility of pathological diagnosis using the 1997 Banff classification update. *Clin Transplant* 2006; 20 Suppl 15: 53.
10. Li B, Hartono C, Ding R, et al. Noninvasive diagnosis of renal-allograft rejection by measurement of messenger RNA for perforin and granzyme B in urine. *N Engl J Med* 2001; 344: 947.
11. Muthukumar T, Dadhania D, Ding R, et al. Messenger RNA for FOXP3 in the urine of renal-allograft recipients. *N Engl J Med* 2005; 353: 2342.
12. Anglicheau D, Suthanthiran M. Noninvasive prediction of organ graft rejection and outcome using gene expression patterns. *Transplantation* 2008; 86: 192.

13. Maluf D G, Mas V R, Archer K J, et al. Molecular pathways involved in loss of kidney graft function with tubular atrophy and interstitial fibrosis. *Mol Med* 2008; 14: 276.
14. Strutz F. Pathogenesis of tubulointerstitial fibrosis in chronic allograft dysfunction. *Clin Transplant* 2009; 23 Suppl 21: 26.
15. Boor P, Ostendorf T, Floege J. Renal fibrosis: novel insights into mechanisms and therapeutic targets. *Nat Rev Nephrol* 2010; 6: 643.
16. Zeisberg M, Neilson E G. Mechanisms of tubulointerstitial fibrosis. *J Am Soc Nephrol* 2010; 21: 1819.
17. Park W, Griffin M, Grande J P, Cosio F, Stegall M D. Molecular evidence of injury and inflammation in normal and fibrotic renal allografts one year posttransplant. *Transplantation* 2007; 83: 1466.
18. Scherer A, Gwinner W, Mengel M, et al. Transcriptome changes in renal allograft protocol biopsies at 3 months precede the onset of interstitial fibrosis/tubular atrophy (IF/TA) at 6 months. *Nephrol Dial Transplant* 2009; 24: 2567.
19. Seron D, Moreso F. Protocol biopsies in renal transplantation: prognostic value of structural monitoring. *Kidney Int* 2007; 72: 690.
20. Park W D, Griffin M D, Cornell L D, Cosio F G, Stegall M D. Fibrosis with inflammation at one year predicts transplant functional decline. *J Am Soc Nephrol* 2010; 21: 1987.
21. Solez K, Colvin R B, Racusen L C, et al. Banff 07 classification of renal allograft pathology: updates and future directions. *Am J Transplant* 2008; 8: 753.
22. Holm S. A simple sequentially rejective multiple test procedure. *Scandinavian Journal of Statistics* 1979; 6: 65.
23. Ivaska J, Pallari H M, Nevo J, Eriksson J E. Novel functions of vimentin in cell adhesion, migration, and signaling. *Exp Cell Res* 2007; 313: 2050.
24. Nakatsuji S, Yamate J, Sakuma S. Relationship between vimentin expressing renal tubules and interstitial fibrosis in chronic progressive nephropathy in aged rats. *Virchows Arch* 1998; 433: 359.
25. Bielesz B, Sirin Y, Si H, et al. Epithelial Notch signaling regulates interstitial fibrosis development in the kidneys of mice and humans. *J Clin Invest* 2010; 120: 4040.
26. Hertig A, Anglicheau D, Verine J, et al. Early epithelial phenotypic changes predict graft fibrosis. *J Am Soc Nephrol* 2008; 19: 1584.
27. Zeisberg M, Soubasakos M A, Kalluri R. Animal models of renal fibrosis. *Methods Mol Med* 2005; 117: 261.
28. Wynn T A. Cellular and molecular mechanisms of fibrosis. *J Pathol* 2008; 214:199.
29. Sharma V K, Bologa R M, Xu G P, et al. Intragraft TGF-beta 1 mRNA: a correlate of interstitial fibrosis and chronic allograft nephropathy. *Kidney Int* 1996; 49: 1297.
30. Hotchkiss H, Chu T T, Hancock W W, et al. Differential expression of profibrotic and growth factors in chronic allograft nephropathy. *Transplantation* 2006; 81: 342.
31. Mas V, Maluf D, Archer K, et al. Establishing the molecular pathways involved in chronic allograft nephropathy for testing new noninvasive diagnostic markers. *Transplantation* 2007; 83: 448.
32. Hinz B, Phan S H, Thannickal V J, Galli A, Bochaton-Piallat M L, Gabbiani G. The myofibroblast: one function, multiple origins. *Am J Pathol* 2007; 170: 1807.
33. Kriz W, Kaissling B, Le Hir M. Epithelial-mesenchymal transition (EMT) in kidney fibrosis: fact or fantasy? *J Clin Invest* 2011; 121: 468.
34. Koesters R, Kaissling B, Lehir M, et al. Tubular overexpression of transforming growth factor-beta1 induces autophagy and fibrosis but not mesenchymal transition of renal epithelial cells. *Am J Pathol* 2010; 177: 632.
35. Yang J, Liu Y. Blockage of tubular epithelial to myofibroblast transition by hepatocyte growth factor prevents renal interstitial fibrosis. *J Am Soc Nephrol* 2002; 13: 96.
36. Yang J, Dai C, Liu Y. Hepatocyte growth factor gene therapy and angiotensin II blockade synergistically attenuate renal interstitial fibrosis in mice. *J Am Soc Nephrol* 2002; 13: 2464.
37. Yang J, Dai C, Liu Y. A novel mechanism by which hepatocyte growth factor blocks tubular epithelial to mesenchymal transition. *J Am Soc Nephrol* 2005; 16: 68.
38. Liu Y, Tolbert E M, Lin L, et al. Up-regulation of hepatocyte growth factor receptor: an amplification and targeting mechanism for hepatocyte growth factor action in acute renal failure. *Kidney Int* 1999; 55: 442.
39. Liu Y. Hepatocyte growth factor and the kidney. *Curr Opin Nephrol Hypertens* 2002; 11:23.
40. Liu Y, Rajur K, Tolbert E, Dworkin L D. Endogenous hepatocyte growth factor ameliorates chronic renal injury by activating matrix degradation pathways. *Kidney Int* 2000; 58: 2028.
41. Mizuno S, Matsumoto K, Kurosawa T, Mizuno-Horikawa Y, Nakamura T. Reciprocal balance of hepatocyte growth factor and transforming growth factor-beta 1 in renal fibrosis in mice. *Kidney Int* 2000; 57: 937.
42. Mizuno S, Matsumoto K, Nakamura T. Hepatocyte growth factor suppresses interstitial fibrosis in a mouse model of obstructive nephropathy. *Kidney Int* 2001; 59: 1304.
43. Lohr J W, Lee T P, Farooqui M, Mookerjee B K. Increased levels of serum hepatocyte growth factor in patients with end-stage renal disease. *J Med* 2000; 31: 131.
44. Mizuno S, Matsumoto K, Nakamura T. HGF as a renotrophic and anti-fibrotic regulator in chronic renal disease. *Front Biosci* 2008; 13: 7072.
45. Xu G P, Sharma V K, Li B, et al. Intragraft expression of IL-10 messenger RNA: A novel correlate of renal allograft rejection. *Kidney Int* 1995; 48: 1504.
46. Suthanthiran M, Ding R, Sharma V, et al. Urinary Cell Messenger RNA Expression Signatures Anticipate Acute Cellular Rejection: A Report from CTOT-04. *Am J Transplant* 2011; 11 Suppl 2: 29.
47. Anglicheau D, Sharma V K, Ding R, et al. MicroRNA expression profiles predictive of human renal allograft status. *Proc Natl Acad Sci USA* 2009; 106: 5330.
48. Hastie T J, Tibshirani R J. Generalized additive models (with discussion). *Statistical Science* 1986; 1: 297.
49. Hastie T J, Tibshirani R J, eds. Generalized Additive Models, New York: Chapman & Hall, 1990.
50. Hosmer D W Jr, Lemeshow S. Applied Logistic Regression, New York: John Wiley & Sons, 1989

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods, devices and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a reactor" or "a mixer" or "a feedstream" includes a plurality of such reactors, mixers or feedstreams (for example, a series of reactors, mixers or feedstreams), and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The following statements describe some of the elements or features of the invention.

Figure 3A:
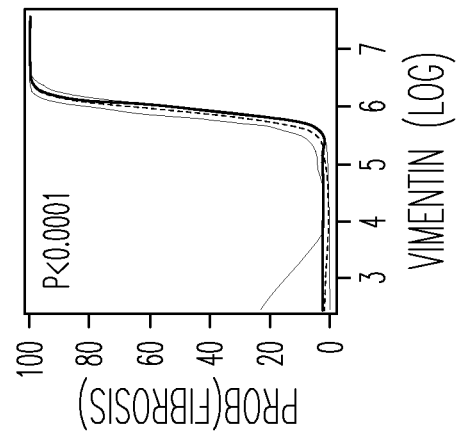
Figure 3B:
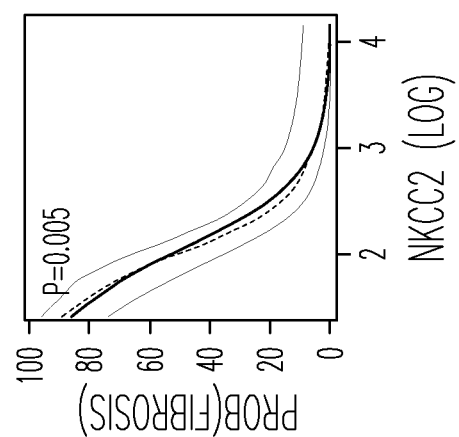
Figure 3C:
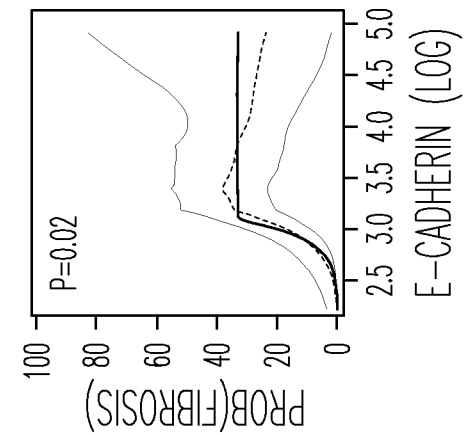

Statements:
1. A method comprising:
   (a) measuring quantities of vimentin mRNA, NKCC2 mRNA, and E-cadherin mRNA in a test sample of cells obtained from urine;
   (b) determining whether the vimentin mRNA quantity is higher, the NKCC2 mRNA quantity is lower or the E-cadherin mRNA is higher than in healthy urinary cells; and thereby detecting that the sample is a fibrotic kidney sample.
2. The method of statement 1, further comprising measuring a housekeeping gene RNA quantity.
3. The method of statement 1 or 2, further comprising measuring a housekeeping gene mRNA quantity, and normalizing the vimentin mRNA quantity, the NKCC2 mRNA quantity, or the E-cadherin mRNA against the housekeeping gene mRNA quantity.
4. The method of statement 1 or 2, further comprising measuring a housekeeping gene mRNA quantity, and dividing the vimentin mRNA quantity, the NKCC2 mRNA quantity, or the E-cadherin mRNA by the housekeeping gene mRNA quantity.
5. The method of any of statements of 2-4, wherein the housekeeping gene is 18S rRNA, actin mRNA, histone mRNA, ribosomal protein mRNA, myosin mRNA, cytochrome c mRNA, $\beta$2-microglobulin mRNA, or major histocompatibility complex mRNA.
6. The method of any of statements of 2-5, wherein the housekeeping gene is 18S rRNA.
7. The method of any of statements 1-6, wherein the vimentin mRNA quantity is divided by the quantity of 18S rRNA/100,000 in the sample to generate a normalized vimentin mRNA value.
8. The method of any of statements 1-7, wherein the vimentin mRNA quantity is divided by the quantity of 18S rRNA/100,000 in the sample to generate a normalized vimentin mRNA value, which is converted into a $\log_{10}$ normalized vimentin mRNA value.
9. The method of any of statements 1-8, wherein detecting that the sample is a fibrotic kidney sample comprises determining that the $\log_{10}$ normalized vimentin mRNA value is at least 5.2, or at least 5.3, or at least 5.4, or at least 5.5, or at least 5.6 (as illustrated in FIG. 3A).
10. The method of any of statements 1-9, wherein the NKCC2 mRNA quantity is divided by the quantity of 18S rRNA/100,000 in the sample to generate a normalized NKCC2 mRNA value.
11. The method of any of statements 1-10, wherein the NKCC2 mRNA quantity is divided by the quantity of 18S rRNA/100,000 in the sample to generate a normalized NKCC2 mRNA value, which is converted into a $\log_{10}$ normalized NKCC2 mRNA value.
12. The method of any of statements 1-11, wherein detecting that the sample is a fibrotic kidney sample comprises determining that the $\log_{10}$ normalized NKCC2 mRNA value is 2.5 or less, or 2.4 or less, or 2.3 or less, or 2.2 or less, or 2.1 or less, or 2.0 or less (as illustrated in FIG. 3B).
13. The method of any of statements 1-12, wherein the E-cadherin mRNA quantity is divided by the quantity of 18S rRNA/100,000 in the sample to generate a normalized E-cadherin mRNA value.
14. The method of any of statements 1-13, wherein the E-cadherin mRNA quantity is divided by the quantity of 18S rRNA/100,000 in the sample to generate a normalized E-cadherin mRNA value, which is converted into a $\log_{10}$ normalized E-cadherin mRNA value.
15. The method of any of statements 1-14, wherein detecting that the sample is a fibrotic kidney sample comprises determining that the $\log_{10}$ normalized E-cadherin mRNA value is at least 2.7, or at least 2.8, or at least 2.9, or at least 3.0, or at least 3.1 (as illustrated in FIG. 3C).

16. The method of any of statements 1-15, wherein measuring quantities of vimentin mRNA, NKCC2 mRNA, and E-cadherin mRNA comprises reverse transcription, polymerase chain reaction preamplification, real-time quantitative polymerase chain reaction, microarray analysis, Northern blotting, nuclease protection assays, RNA fingerprinting, ligase chain reaction, Qbeta replicase, isothermal amplification method, strand displacement amplification, transcription based amplification systems, quantitative nucleic acid amplification, combined reverse transcription/nucleic acid amplification, nuclease protection, Serial Analysis Gene Expression (SAGE), next generation sequencing, gene expression microarray, and combinations thereof.

17. The method of any of statements 1-16, wherein measuring quantities of vimentin mRNA, NKCC2 mRNA, and E-cadherin mRNA comprises reverse transcription, polymerase chain reaction preamplification, real-time quantitative polymerase chain reaction, or a combination thereof.

18. The method of any of statements 1-17, wherein a nucleic acid measuring quantities of vimentin mRNA, NKCC2 mRNA, and E-cadherin mRNA comprises use of a probe or primer that can stringently hybridizes to a nucleic acid encoding an amino acid sequence selected from the group consisting of SEQ ID NO:2, 4, 6, 8, 10 or a combination thereof.

19. The method of any of statements 1-18, wherein a nucleic acid measuring quantities of vimentin mRNA, NKCC2 mRNA, and E-cadherin mRNA comprises use of a probe or primer that can stringently hybridizes to a nucleic acid comprising any of SEQ ID NO:1, 3, 5, 7, 9, 12, 13, 14, 69, 70, 71, 75, 76, 77, or a combination thereof.

20. The method of any of statements 1-19, wherein a nucleic acid measuring quantities of 18S rRNA comprises use of a probe or primer that can stringently hybridize to a nucleic acid comprising any of SEQ ID NO: 11, 78, 79, 81, or a combination thereof.

21. The method of any of statements 1-20, wherein a nucleic acid measuring quantities of vimentin mRNA, NKCC2 mRNA, and E-cadherin mRNA comprises use of a probe or primer that has at least 90% or at least 95% sequence identity or sequence complementarity to any of SEQ ID NO:1, 3, 5, 7, 9, 12, 13, 14, 69, 70, 71, 75, 76, 77, or a combination thereof.

22. The method of any of statements 1-21, wherein a nucleic acid measuring quantities of 18S rRNA comprises use of a probe or primer that has at least 90% or at least 95% sequence identity or sequence complementarity to any of SEQ ID NO: 11, 78, 79, 81, or a combination thereof.

23. The method of any of statements 1-22, further comprising assigning a composite score calculated as follows:

Composite Score =

$36.10283 + [-15.84215 * \log_{10}(18s)] + 1.56907 * \log_{10}(18s) * \log_{10}(18s) +$ $5.11698 * \max[0, \log_{10}(\text{Vimentin}) - 5.6] + [$ $-1.44145 * \log_{10}(NKCC2)] + 3.31357 * \min[3.1, \log_{10}(E\text{-cadherin})]$ where, $\max[0, \log_{10}(\text{Vimentin}) - 5.6] =$ 0 whenever $\log_{10}(\text{Vimentin})$ is $\leq 5.6$ and =

$\log_{10}(\text{Vimentin}) - 5.6$ whenever $\log_{10}(\text{Vimentin})$ is $> 5.6$;

$\min[3.1, \log_{10}(E\text{-cadherin})] =$ $\log_{10}(E\text{-cadherin})$ whenever $\log_{10}(E - \text{cadherin}) < 3.1$ and =

3.1 whenever $\log_{10}(E\text{-cadherin}) \geq 3.1$;

and $*$ signifies multiplication

24. The method of statement 23, wherein:
$\log_{10}(18s \text{ RNA})$ is $\log_{10}$ of 18S RNA quantity/100,000 in the test sample;
$\log_{10}(\text{Vimentin})$ is $\log_{10}$ of the normalized vimentin mRNA quantity in the test sample;
$\log_{10}(NKCC2)]$ is $\log_{10}$ of the normalized NKCC2 mRNA quantity in the test sample; and
$\log_{10}(E\text{-cadherin})$ is $\log_{10}$ of the normalized E-cadherin mRNA quantity in the test sample.

25. The method of statement 23 or 24, wherein the vimentin mRNA quantity, the NKCC2 mRNA quantity, and the E-cadherin mRNA quantity is divided by the 18S rRNA quantity divided by 100,000 (i.e., [18S rRNA]/100,000) before generating the $\log_{10}(\text{Vimentin})$, the $\log_{10}(NKCC2)$, and the $\log_{10}(E\text{-cadherin})$ values, respectively.

26. The method of any of statements 23-25, wherein the composite score varies from about 1 to 8, and a normal (healthy) composite score is about 3.5.

27. The method of any of statements 23-26, wherein a test sample with a composite score of about 4.7 indicates a subject has fibrosis.

28. The method of any of statements 23-27, wherein a test sample with a composite score of about 4.7 to about 6.5 indicates a subject has mild to moderate fibrosis; and/or a test sample with a composite score of about 6.5 or more indicates a subject has moderate to severe fibrosis.

29. The method of any of statements 1-28, further comprising treating a subject from which the fibrotic kidney sample was obtained.

30. The method of any of statements 1-29, further comprising treating a subject from which the fibrotic kidney sample was obtained by administering a therapeutic agent to the subject.

31. The method of any of statements 1-30, further comprising treating a subject from which the fibrotic kidney sample was obtained by administering to the subject a therapeutic agent selected from an agent that treats the underlying cause(s) of kidney fibrosis, an agent that delays the progression of kidney fibrosis, an agent that ameliorates the symptoms of kidney fibrosis, or a combination thereof.

32. The method of any of statements 1-31, further comprising replacing a kidney in a subject from which the fibrotic kidney sample was obtained.

33. A method comprising:
  (a) measuring quantities of vimentin RNA, NKCC2 RNA, E-cadherin RNA and 18S rRNA in a test sample of cells obtained from a subject's urine to generate a vimentin RNA quantity value [vimentin], a NKCC2 RNA quantity value [NKCC2], an E-cadherin RNA quantity value [E-cadherin], and an 18S rRNA quantity value [18S rRNA];

(b) identifying the subject as a patient who would benefit from treatment of kidney fibrosis when:
  (i) the $\log_{10}([\text{vimentin}]/[18\text{S rRNA}/10^5])$ value is greater than about 5.0;
  (ii) the $\log_{10}([\text{NKCC2}]/[18\text{S rRNA}]/10^5)$ value is less than about 3.0; or
  (iii) the $\log_{10}([\text{E-cadherin}]/[18\text{S rRNA}/10^5])$ value is greater than about 3.0.
34. The method of statement 33, further comprising treating the patient who would benefit from treatment of kidney fibrosis.
35. The method of statement 33 or 34, further comprising treating the patient who would benefit from treatment of kidney fibrosis by administering a therapeutic agent to the patient.
36. The method of any of statements 33-35, further comprising treating the patient who would benefit from treatment of kidney fibrosis by administering to the patient a therapeutic agent selected from an agent that treats the underlying cause(s) of kidney fibrosis, an agent that delays the progression of kidney fibrosis, an agent that ameliorates the symptoms of kidney fibrosis, or a combination thereof.
37. The method of any of statements 33-36, further comprising replacing a kidney in the patient who would benefit from treatment of kidney fibrosis.
38. The method of any of statements 33-37, further comprising any of the methods of statements 1-32.
39. A method comprising: treating kidney fibrosis in a subject when a sample of urinary cells from the subject has a vimentin mRNA quantity that is higher, a NKCC2 mRNA quantity that is lower, or an E-cadherin mRNA that is higher than in healthy urinary cells.
40. A method comprising: treating kidney fibrosis in a subject when a sample of urinary cells from the subject has:
  (i) a $\log_{10}([\text{vimentin}]/[18\text{S rRNA}])$ value is greater than about 5.0;
  (ii) a $\log_{10}([\text{NKCC2}]/[18\text{S rRNA}])$ value is less than about 3.0;
  (iii) a $\log_{10}([\text{E-cadherin}]/[18\text{S rRNA}])$ value is greater than about 3.0; or
  (iv) a combination thereof.
41. A method comprising: treating kidney fibrosis in a subject when a sample of urinary cells from the subject has:
  (i) a $\log_{10}([\text{vimentin}]/[18\text{S rRNA}/10^5])$ value greater than about 5.0;
  (ii) a $\log_{10}([\text{NKCC2}]/[18\text{S rRNA}/10^5])$ value less than about 3.0;
  (iii) a $\log_{10}([\text{E-cadherin}]/[18\text{S rRNA}/10^5])$ value greater than about 3.0; or
  (iv) a combination thereof.
42. The method of any of statements 39-41, further comprising any of the methods of statements 1-32.

The claims summarize features of the invention.

---

What is claimed:

1. A method comprising: treating kidney fibrosis in a subject with a kidney transplant having renal fibrosis, wherein the method comprises:

quantitative nucleic acid amplification measurement of sample RNA from urinary cells of the subject using primers specific for vimentin, NKCC2, E-cadherin, and 18S rRNA;

calculating a composite score as follows:

$$\text{Composite Score} = 36.10283 + [-15.84215 * \log_{10}(18s\ RNA)] +$$

$$1.56907 * \log_{10}(18s\ RNA) * \log_{10}(18s\ RNA) +$$

$$5.11698 * \max[0, \log_{10}(\text{Vimentin}) - 5.6] + [$$

$$-1.44145 * \log_{10}(NKCC2)] + 3.31357 * \min[3.1, \log_{10}(E\text{-cadherin})]$$

where, $\log_{10}$(18s RNA) is $\log_{10}$ of 18S RNA quantity/$10^5$ in the test sample;

$\log_{10}$(Vimentin) is $\log_{10}$ of a normalized vimentin mRNA quantity in the test sample;

$\log_{10}$(NKCC2)] is $\log_{10}$ of a normalized NKCC2 mRNA quantity in the test sample;

$\log_{10}$(E-cadherin) is $\log_{10}$ of a normalized E-cadherin mRNA quantity in the test sample;

max[0, $\log_{10}$(Vimentin)−5.6]=0 whenever $\log_{10}$(Vimentin) is ≤5.6 and =$\log_{10}$(Vimentin−5.6 whenever $\log_{10}$(Vimentin) is >5.6;

min[3.1, $\log_{10}$(E-cadherin)]=$\log_{10}$(E-cadherin) whenever $\log_{10}$(Ecadherin)<3.1 and =3.1 whenever $\log_{10}$(E-cadherin)≥3.1; and * signifies multiplication; and removal of the kidney transplant and transplantation of a second kidney transplant, or administering one or more anti-inflammatory agent, anti-coagulant, antioxidant, blood pressure medication, angiotensin-converting enzyme inhibitor, angiotensin AT1 receptor blocker, connective tissue growth factor inhibitor, or antifibrotic agent, when the composite score is 4.7 or more to thereby treat kidney fibrosis in a subject.

2. The method of claim 1, comprising: treating kidney fibrosis in the subject when the sample RNA of a test sample of urinary cells from the subject has:
   (i) a $\log_{10}$([vimentin]/[18S rRNA]/$10^5$) value greater than about 5.0;
   (ii) a $\log_{10}$([NKCC2]/[18S rRNA]/$10^5$) value less than about 3.0; or
   (iii) a $\log_{10}$([E-cadherin]/[18S rRNA]/$10^5$) value greater than about 3.0.

3. The method of claim 1 wherein the composite score varies from about 1 to 8, and a normal composite score is about 3.5.

4. The method of claim 1, wherein a test sample with a composite score of more than about 4.7 indicates a subject has fibrosis.

5. The method of claim 1, wherein performing quantitative nucleic acid amplification comprises use of a probe or primer that can stringently hybridize to a nucleic acid comprising SEQ NO:11.

* * * * *

UNITED STATES PATENT AND TRADEMARK OFFICE
CERTIFICATE OF CORRECTION

PATENT NO. : 10,472,679 B2
APPLICATION NO. : 14/400873
DATED : November 12, 2019
INVENTOR(S) : Suthanthiran et al.

Page 1 of 1

It is certified that error appears in the above-identified patent and that said Letters Patent is hereby corrected as shown below:

On the Title Page

On page 2, in Column 1, under "Other Publications", Line 41, delete "Factor-B1" and insert --Factor-β1-- therefor On page 2, in Column 2, under "Other Publications", Line 24, delete "TGF-B1" and insert --TGF-β1-- therefor On page 2, in Column 2, under "Other Publications", Line 43, delete "rejectiion"," and insert --rejection",-- therefor On page 2, in Column 2, under "Other Publications", Line 46, delete "Transistion" and insert --Transition-- therefor On page 2, in Column 2, under "Other Publications", Line 48, delete "Theraphy" and insert --Therapy-- therefor In the Claims In Column 96, Line 21, in Claim 5, after "SEQ", insert --ID--

Signed and Sealed this
Second Day of June, 2020

Andrei Iancu
*Director of the United States Patent and Trademark Office*